United States Patent
Iwakuma et al.

(10) Patent No.: US 8,080,658 B2
(45) Date of Patent: *Dec. 20, 2011

(54) MATERIAL FOR ORGANIC ELECTROLUMINESCENT ELEMENT AND ORGANIC ELECTROLUMINESCENT ELEMENT EMPLOYING THE SAME

(75) Inventors: Toshihiro Iwakuma, Chiba (JP); Jun Endo, Chiba (JP); Masaki Numata, Chiba (JP); Kenichi Fukuoka, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 205 days.

This patent is subject to a terminal disclaimer.

(21) Appl. No.: 11/775,593

(22) Filed: Jul. 10, 2007

(65) Prior Publication Data

US 2009/0030202 A1    Jan. 29, 2009

(51) Int. Cl.
C07D 491/00 (2006.01)
C07D 307/91 (2006.01)
C07D 327/04 (2006.01)
C07D 471/00 (2006.01)

(52) U.S. Cl. .......... 544/251; 548/440; 549/460; 549/33; 546/82; 546/85

(58) Field of Classification Search .................. 544/251; 548/440; 549/460, 33; 546/82, 85
See application file for complete search history.

(56) References Cited

U.S. PATENT DOCUMENTS

| 7,504,769 B2 * | 3/2009 | Radu et al. ..................... 313/504 |
| 2007/0224446 A1 * | 9/2007 | Nakano et al. ................. 428/690 |

FOREIGN PATENT DOCUMENTS

| JP | 2002-308837 | | 10/2002 |
| JP | 2004-214050 | | 7/2004 |
| JP | 2005-112765 | * | 4/2005 |
| JP | 2006151844 | * | 6/2006 |
| JP | 2007-189001 | | 7/2007 |
| JP | 2007-288035 | | 11/2007 |
| WO | WO 2005113506 | * | 12/2005 |
| WO | WO 2006/128800 A1 | | 12/2006 |
| WO | WO 2006/137210 A1 | | 12/2006 |
| WO | WO 2006128800 | * | 12/2006 |
| WO | WO 2007/111176 A1 | | 10/2007 |
| WO | WO 2007/119816 A1 | | 10/2007 |
| WO | WO 2007111176 | * | 10/2007 |

OTHER PUBLICATIONS

Kratky et al. STN Accession No. 1999:23735 Document No. 130:153463; abstract of. Monatshefte fuer Chemie (1998), 129(12), 1319-1327.*
Eberson et al. STN Document No. 129:236911, Abstract of Journal of the Chemical Society, Perkin Transactions 2: Physical Organic Chemistry (1996), (7), 1289-1295.*
U.S. Appl. No. 11/943,879, filed Nov. 21, 2007, Iwakuma, et al.
U.S. Appl. No. 11/943,934, filed Nov. 21, 2007, Iwakuma, et al.

* cited by examiner

Primary Examiner — Nizal Chandrakumar
(74) Attorney, Agent, or Firm — Oblon, Spivak, McClelland, Maier & Neustadt, L.L.P.

(57) ABSTRACT

A material for organic electroluminescence devices for use as a host material in combination with at least one phosphorescent metal complex contains a compound represented by formula 1:

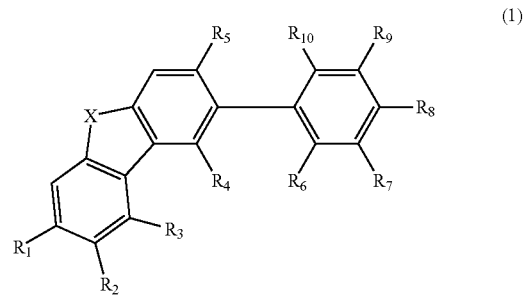

wherein $R_1$ to $R_{10}$ are each independently hydrogen atom, halogen atom, alkyl group having 1 to 40 carbon atoms, cycloalkyl group having 3 to 15 carbon atoms, heterocyclic group having 3 to 20 carbon atoms which is optionally substituted, alkoxy group having 1 to 40 carbon atoms, non-condensed aryl group having 6 to 40 carbon atoms, condensed aryl group having 10 to 18 carbon atoms, aryloxy group having 6 to 20 carbon atoms, aralkyl group having 7 to 20 carbon atoms, arylamino group having 6 to 40 carbon atoms, alkylamino group having 1 to 40 carbon atoms, aralkylamino group having 7 to 60 carbon atoms, arylcarbonyl group having 7 to 40 carbon atoms, alkyl halide group having 1 to 40 carbon atoms, or cyano group, $R_8$ and $R_9$ being optionally bonded to each other to form a ring structure and each of $R_1$ to $R_{10}$ being optionally substituted and having no polymerizable functional group at its terminal end; and X is sulfur atom or oxygen atom.

13 Claims, No Drawings

MATERIAL FOR ORGANIC ELECTROLUMINESCENT ELEMENT AND ORGANIC ELECTROLUMINESCENT ELEMENT EMPLOYING THE SAME

BACKGROUND OF THE INVENTION

1. Field of the Invention

The present invention relates to materials for organic electroluminescence devices and organic electroluminescence devices using the materials and, more particularly to materials for organic electroluminescence devices which realize electroluminescence devices exhibiting a high emitting efficiency, causing little pixel defects, exhibiting a high heat resistance and having a long lifetime.

2. Description of the Prior Art

An organic electroluminescence device (organic EL device) is a spontaneous emission device which utilizes the phenomenon of fluorescence which occurs by the energy of recombination between holes injected from an anode and electrons injected from a cathode by application of electric field. C. W. Tang of Eastman Kodak Company (C. W. Tang and S. A. Vanslyke, Applied Physics Letters, 51, p. 913, 1987) reported a laminated organic EL device which is driven under low electric voltage. Since that time, many studies have been made on organic EL devices using organic materials as the constituting materials. Tang et al. used a light emitting layer of tris(8-quinolinolato) aluminum and a hole transport layer of a triphenyldiamine derivative. Advantages of the laminate structure are that the efficiency of hole injection into the light emitting layer can be increased, that the efficiency of forming excitons by recombination can be increased by blocking electrons injected from the cathode, and that excitons formed can be confined in the light emitting layer. As the structure of organic EL devices, a two-layered structure having a hole transport (injection) layer and an electron transport/light emitting layer and a three-layered structure having a hole transport (injection) layer, a light emitting layer and an electron transport (injection) layer are well known. To increase the efficiency of recombination of injected holes and electrons in laminated devices, the structure of the device and the process for forming the device have been studied.

As the light emitting material of organic EL devices, chelate complexes such as tris(8-quinolinolato) aluminum, coumarine derivatives, tetraphenylbutadiene derivatives, distyrylarylene derivatives and oxadiazole derivatives are known. It is reported that these light emitting materials emit visible light ranging from blue to red and the development of color display devices is expected (for example, Patent Documents 1-3).

It is recently proposed to use a light emitting layer of a phosphorescent material in addition to a light emitting layer of a fluorescent material (for example, Non-Patent Documents 1 and 2). A high efficiency of light emission is achieved by utilizing the excited singlet state and the excited triplet state of the organic phosphorescent material in the light emitting layer. It is considered that the singlet exiton and the triplet exciton are formed in a proportion of 1:3 due to the difference in the spin multiplicity when electrons and holes are recombined in an organic EL device. Therefore, it is expected that an efficiency of light emission 3 to 4 times as great as that of a device utilizing only the fluorescent material can be achieved by utilizing a phosphorescent light emitting material.

To prevent the excited triplet state or the triplet exciton from quenching, the organic EL devices described above are made into a laminate structure having an anode, a hole transport layer, an organic light emitting layer, an electron transport layer (a hole blocking layer), an electron transport layer and a cathode in this order, while using an organic light emitting layer made of a host compound and a phosphorescent compound (for example, Patent Documents 4-9). In these Patent Documents, host materials having a dibenzofuran structure or a dibenzothiophene structure are described. However, there is nothing about their advantage in the device performance as compared with a host material having a carbazole structure.

Patent Documents 10 and 11 disclose compounds prepared by bonding a carbazole structure to dibenzo compounds. The proposed compounds are used in a host material for a blue phosphorescent device in examples thereof. The compounds of the present invention are not taught and the effect is uncertain.

Patent Documents 12 to 14 disclose compounds prepared by bonding an anthracene structure to dibenzo compounds. However, the energy level of the excited triplet state of the proposed compounds is small because of the anthracene structure. Therefore, a blue phosphorescent material does not emit light even if any of the proposed compounds is used as a host material for the light emitting layer.

Patent Document 15 discloses dibenzofuran compounds essentially having at least two polymerizable functional groups. If the host material of a phosphorescent device has in its molecule a polymerizable group such as propenylene group, vinylene group and 4-propyl-2-pentenylene group which is formed by introducing an unsaturated bond such as double bond and triple bond, radicals are propagatedly generated in the device to adversely affect the emitting efficiency and lifetime.

[Patent Document 1] JP 8-239655A
[Patent Document 2] JP 7-138561A
[Patent Document 3] JP 3-200889A
[Patent Document 4] WO 65/101912
[Patent Document 5] JP 5-109485A
[Patent Document 6] JP 2004-002351A
[Patent Document 7] WO 04/096945
[Patent Document 8] JP 2002-308837A
[Patent Document 9] WO 2005-113531
[Patent Document 10] JP 2005-112765A
[Patent Document 11] WO 2006-114966
[Patent Document 12] JP 2005-314239A
[Patent Document 13] JP 2007-77094A
[Patent Document 14] JP 2007-63501A
[Patent Document 15] JP 2007-110097A
[Non-Patent Document 1] D. F. O'Brien and M. A. Baldo et al. "Improved energy transferring electrophosphorescent devices" Applied Physics letters Vol. 74 No. 3, pp 442-444, Jan. 18, 1999
[Non-Patent Document 2] M. A. Baldo et al. "Very high-efficiency green organic light-emitting devices based on electrophosphorescence" Applied Physics letters Vol. 75 No. 1, pp-4-6, Jul. 5, 1999

SUMMARY OF THE INVENTION

The present invention has been made to overcome the above problems and has an object of providing a material for organic EL devices which realizes an EL device exhibiting a high efficiency of light emission, causing little pixel defects, exhibiting a high heat resistance and having a long lifetime.

As a result of extensive reasech in view of achieving the above object, the inventors have found that a compound represented by the following formula 1, which has a dibenzothiophene or dibenzofuran structure having at its 2-position substituted with an aromatic hydrocarbon group, creates a excited triplet state having a sufficient energy level enough to prevent the emitting efficiency of a blue phosphorescent complex from being reduced. It has been further found that the compound realizes a highly efficient and highly heat-resistant organic EL device causing little pixel defects and having a long lifetime. The present invention is based on these findings.

Thus, the preset invention provides a material for organic electroluminescence devices for use as a host material in combination with at least one phosphorescent metal complex, comprising a compound represented by the following formula 1:

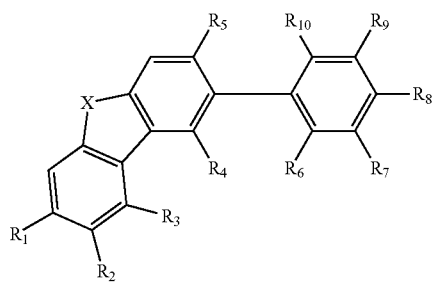

(1)

wherein $R_1$ to $R_{10}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group, $R_8$ and $R_9$ being optionally bonded to each other to form a ring structure and each of $R_1$ to $R_{10}$ having no polymerizable functional group at its terminal end; and X is sulfur atom or oxygen atom.

The present invention further provides an organic electroluminescence device which includes a cathode, an anode and an organic thin film layer having one or more layers, the organic thin film layer being interposed between the cathode and the anode and having a light emitting layer containing a host material in combination with at least one phosphorescent metal complex, and at least one layer of the organic thin film layer containing the material for organic electroluminescence devices mentioned above.

The organic EL device made using the material for organic EL devices of the present invention is free from pixel defects, highly efficient, highly heat resistant and durable for a long period of time.

DETAILED DESCRIPTION OF THE INVENTION

The material for organic EL devices of the invention includes the compound represented by the following formula 1:

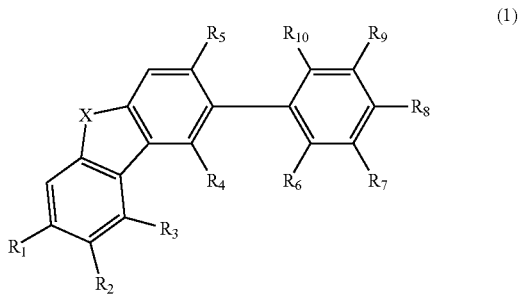

(1)

wherein $R_1$ to $R_{10}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group. $R_8$ and $R_9$ may be bonded to each other to form a ring structure. Each of $R_1$ to $R_{10}$ (also inclusive of substituted $R_1$ to $R_{10}$) has no polymerizable functional group, such as vinyl group, 1-methylvinyl group, 1-halovinyl group, and 1-trihalomethylvinyl group, at its terminal end.

The halogen atom includes, for example, fluorine, chlorine, bromine and iodine.

Examples of the alkyl group having 1 to 40 carbon atoms which is optionally substituted include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 1,2-dinitroethyl group, 2,3-dinitro-t-butyl group, and 1,2,3-trinitropropyl group. Preferred are methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 1-pentylhexyl group, 1-butylpentyl group, and 1-heptyloctyl group. The carbon number of the alkyl group (exclusive of substituent) is preferably from 1 to 10.

Examples of the cycloalkyl group having 3 to 15 carbon atoms which is optionally substituted include cyclopentyl group, cyclohexyl group, cyclooctyl group, and 3,3,5,5-tetramethylcyclohexyl group, with cyclohexyl group, cyclooctyl group and 3,5-tetramethylcyclohexyl group being preferred. The carbon number of the cycloalkyl group (exclusive of substituent) is preferably from 8 to 12.

Examples of the heterocyclic group having 3 to 20 carbon atoms which is optionally substituted include 1-pyrrolyl group, 2-pyrrolyl group, 3-pyrrolyl group, pyrazinyl group, 2-pyridinyl group, 1-imidazolyl group, 2-imidazolyl group, 1-pyrazolyl group, 1-indolizinyl group, 2-indolizinyl group, 3-indolizinyl group, 5-indolizinyl group, 6-indolizinyl group, 7-indolizinyl group, 8-indolizinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 6-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, β-carboline-1-yl, β-carboline-3-yl, β-carboline-4-yl, β-carboline 5-yl, β-carboline-6-yl, β-carboline-7-yl, β-carboline-6-yl, β-carboline-9-yl, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group, and 4-germafluorenyl group.

Of the above, preferred are 2-pyridinyl group, 1-indolizinyl group, 2-indolizinyl group, 3-indolizinyl group, 5-indolizinyl group, 6-indolizinyl group, 7-indolizinyl group, 8-indolizinyl group, 2-imidazopyridinyl group, 3-imidazopyridinyl group, 5-imidazopyridinyl group, 6-imidazopyridinyl group, 7-imidazopyridinyl group, 8-imidazopyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 1-carbazolyl group, 2-carbazolyl group, 3-carbazolyl group, 4-carbazolyl group, 9-carbazolyl group, 1-dibenzofuranyl group, 2-dibenzofuranyl group, 8-dibenzofuranyl group, 4-dibenzofuranyl group, 1-dibenzothiophenyl group, 2-dibenzothiophenyl group, 3-dibenzothiophenyl group, 4-dibenzothiophenyl group, 1-silafluorenyl group, 2-silafluorenyl group, 3-silafluorenyl group, 4-silafluorenyl group, 1-germafluorenyl group, 2-germafluorenyl group, 3-germafluorenyl group, and 4-germafluorenyl group. The carbon number of the heterocyclic group (exclusive of substituent) is preferably from 3 to 14.

The alkoxy group having 1 to 40 carbon atoms which is optionally substituted is represented by —OY wherein Y and its preferred examples are the same as the alkyl groups mentioned above.

Examples of the non-condensed aryl group having 6 to 40 carbon atoms which is optionally substituted include phenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4''-t-butyl-p-terphenyl-4-yl group, o-cumenyl group, m-cumenyl group, p-cumenyl group, 2,3-xylyl group, 3,4-xylyl group, 2,5-xylyl group, mesityl group, and m-quaterphenyl group, with phenyl group, 2-biphenylyl group, 3-biphenylyl group, 4-biphenylyl group, m-terphenyl-4-yl group, m-terphenyl-3-yl group, m-terphenyl-2-yl group, p-tolyl group, 3,4-xylyl group, and m-quaterphenyl-2-yl group being preferred. The carbon number of the non-condensed aryl group (exclusive of substituent) is preferably from 6 to 24.

Examples of the condensed aryl group having 10 to 18 carbon atoms which is optionally substituted include 1-naphthyl group, 2-naphthyl group, 1-phenanthrenyl group, 2-phenanthrenyl group, 3-phenanthrenyl group, 4-phenanthrenyl group, 9-phenanthrenyl group, 1-triphenylenyl group, 2-triphenylenyl group, 3-triphenylenyl group, and 4-triphenylenyl group.

The aryloxy group having 6 to 20 carbon atoms which is optionally substituted is represented by —OAr wherein Ar and its preferred examples are the same as the non-condensed aryl groups mentioned above.

Examples of the aralkyl group having 7 to 20 carbon atoms which is optionally substituted include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group, with benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group being preferred. The alkyl moiety of the aralkyl group has preferably from 1 to 8 carbon atoms, and the aryl moiety (inclusive of heteroaryl) has preferably from 6 to 18 carbon atoms.

Each of the arylamino group having 6 to 40 carbon atoms which is optionally substituted, the alkylamino group having 1 to 40 carbon atoms which is optionally substituted and the aralkylamino group having 7 to 60 carbon atoms which is optionally substituted is represented by —NQ$_1$Q$_2$, wherein Q$_1$ and Q$_2$ are each independently selected from the alkyl groups, aryl groups and aralkyl groups described above. Similarly, preferred examples of Q$_1$ and Q$_2$ are the same as those described above.

The arylcarbonyl group having 7 to 40 carbon atoms which is optionally substituted is represented by —COAr$_2$, wherein Ar$_2$ and its preferred examples are the same as the aryl groups mentioned above.

The alkyl halide group having 1 to 40 carbon atoms which is optionally substituted is, for example, derived from the alkyl group mentioned above by substituting halogen atom for at least one hydrogen atom. Preferred alkyl halide groups are derived from the preferred alkyl groups in the same manner.

The compound of the formula 1 is preferably represented by any of the following formulae 2 to 5:

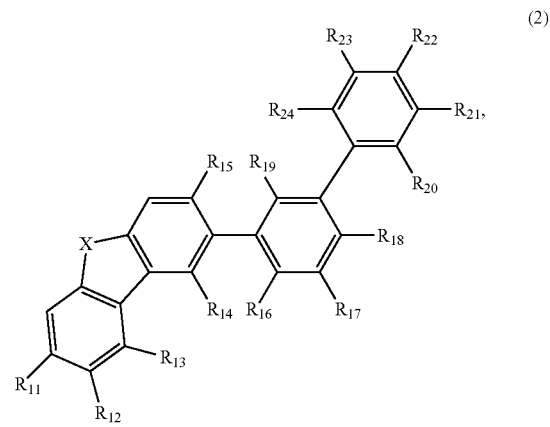

(2)

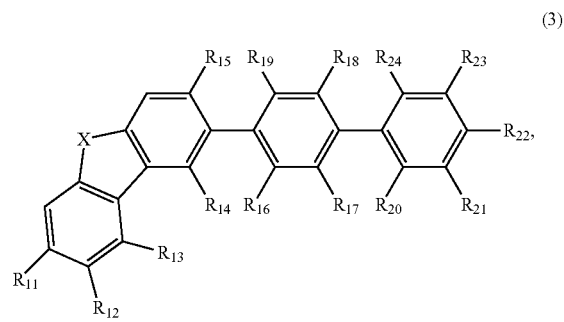

(3)

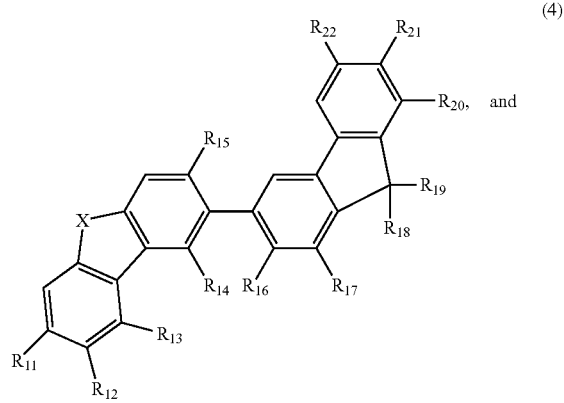

(4)

-continued

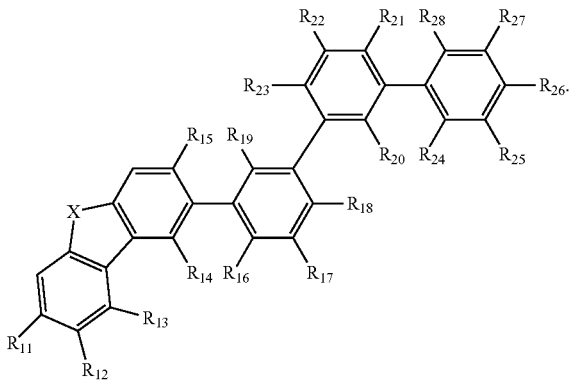

(5)

The definitions of $R_{11}$ to $R_{24}$ and X of the formulae 2 and 3, the definitions of $R_{11}$ to $R_{22}$ and X of the formula 4, and the definitions of $R_{11}$ to $R_{28}$ and X of the formula 5 are the same as those of $R_1$ to $R_{10}$ and X of the formula 1.

The compound of the formula 2 is preferably represented by the following formula 6 or 9:

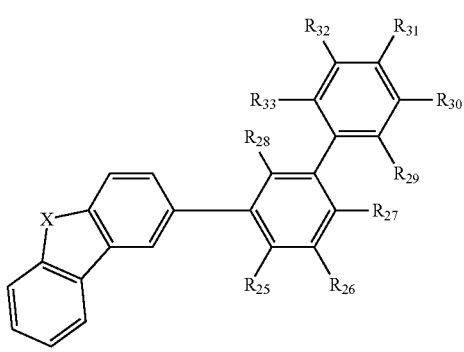

(6)

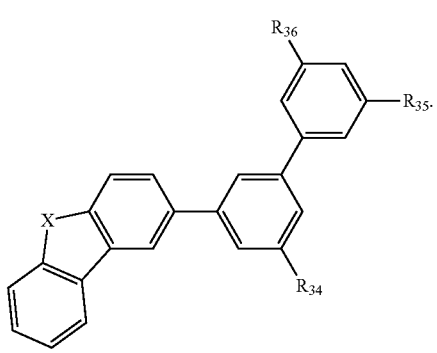

(9)

The definitions of $R_{25}$ to $R_{33}$ and X of the formula 6 and the definitions of $R_{34}$ to $R_{36}$ and X of the formula 9 are the same as those of $R_1$ to $R_{10}$ and X of the formula 1.

The compound of the formula 3 is preferably represented by the following formula 7:

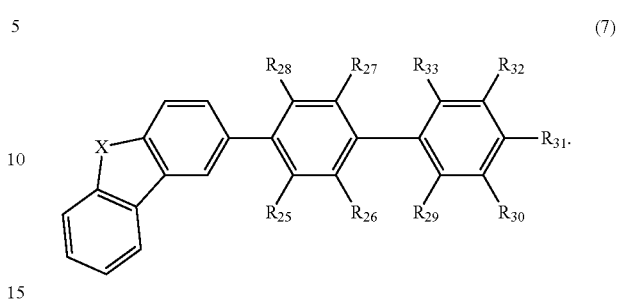

(7)

The definitions of $R_{25}$ to $R_{33}$ and X of the formula 7 are the same as those of $R_1$ to $R_{10}$ and X of the formula 1.

The compound of the formula 4 is preferably represented by the following formula 8:

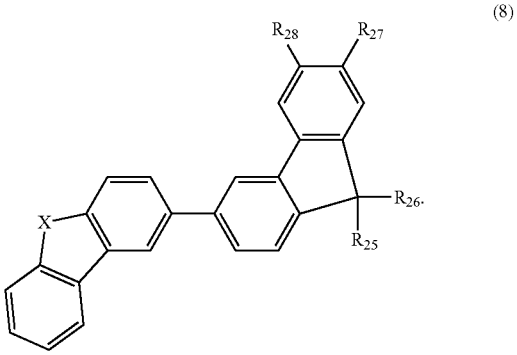

(8)

The definitions of $R_{25}$ to $R_{28}$ and X of the formula 8 are the same as those of $R_1$ to $R_{10}$ and X of the formula 1.

Examples of the substituent groups for $R_1$ to $R_{36}$ of the formulae 1 to 9 include alkyl group having 1 to 8 carbon atoms (methyl group, ethyl group, propyl group, isopropyl group, n-butyl group, s-butyl group, isobutyl group, t-butyl group, n-pentyl group, n-hexyl group, n-heptyl group, n-octyl group); hydroxyalkyl group having 1 to 5 carbon atoms (hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group); haloalkyl group having 1 to 4 carbon atoms (chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group); aminoalkyl group having 1 to 4 carbon atoms (aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group); cyanoalkyl group having 1 to 4 carbon atoms (cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group); nitroalkyl group having 1 to 5 carbon atoms (nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group); (alkyl)cycloalkyl group having 3 to 10 carbon atoms (cyclopropyl group, cyclobutyl group, cyclopentyl group, cyclohexyl group, 4-methylcyclohexyl group, 1-adamantyl group, 2-adamantyl group, 1-norbornyl group, 2-norbornyl group); having 1 to 60 carbon atoms alkoxy group (ethoxy group, methoxy group, isopropoxy group, n-propoxy group, s-butoxy group, t-butoxy group, pentoxy group, hexyloxy group); cycloalkoxy group having 3 to 6 carbon atoms (cyclopentoxy group, cyclohexyloxy group); aryl group having 5 to 40 ring atoms; amino group substituted with aryl group having 5 to 40 ring atoms; ester group having aryl group with 5 to 40 ring atoms; ester group having alkyl group with 1 to 60 carbon atoms; cyano group; nitro group; halogen atom; hydroxyl group; amino group; substituted or non-substituted carbazolyl group (1-carbazolyl group, 2-carbazolyl group, 3-carbazolyl group, 4-carbazolyl group, 9-carbazolyl group); substituted or non-substituted dibenzofuranyl group (1-dibenzofuranyl group, 2-dibenzofuranyl group, 3-dibenzofuranyl group, 4-dibenzofuranyl group); and substituted or non-substituted dibenzothiophenyl group (1-dibenzothiophenyl group, 2-dibenzothiophenyl group, 3-dibenzothiophenyl group, 4-dibenzothiophenyl group). The substituent groups for carbazolyl group, dibenzofuranyl group, and dibenzothiophenyl group are selected from the groups recited above.

At least one of $R_{16}$ to $R_{24}$ of the formulae 2 and 3, at least one of $R_{16}$ to $R_{17}$ and $R_{20}$ to $R_{22}$ of the formula 4, at least one of $R_{16}$ to $R_{28}$ of the formula 5, at least one of $R_{25}$ to $R_{33}$ of the formulae 6 and 7, at least one of $R_{27}$ to $R_{28}$ of the formula 8, and at least one of $R_{34}$ to $R_{36}$ of the formula 9 are preferably selected from the substituted or non-substituted carbazolyl group, substituted or non-substituted dibenzofuranyl group, substituted or non-substituted azacarbazolyl group and substituted or non-substituted dibenzothiophenyl group, each being recited above.

Examples of the compounds of the formulae 1 to 9 are shown below, although not limited thereto.

No. 1

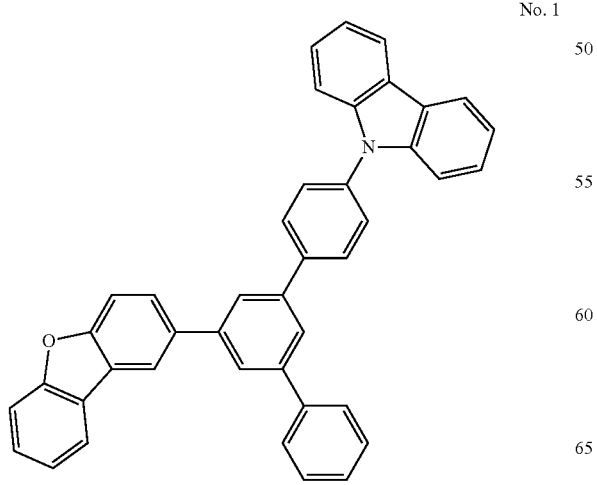

No. 2

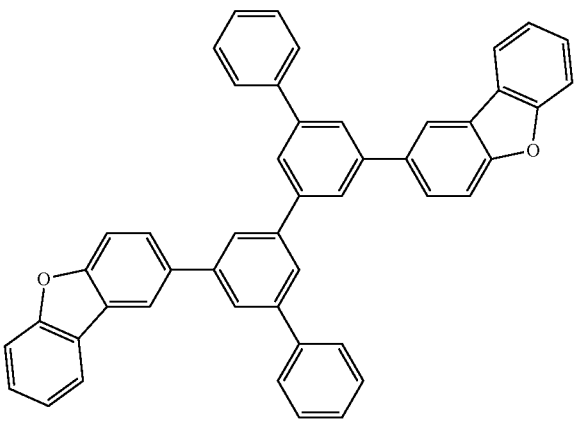

No. 3

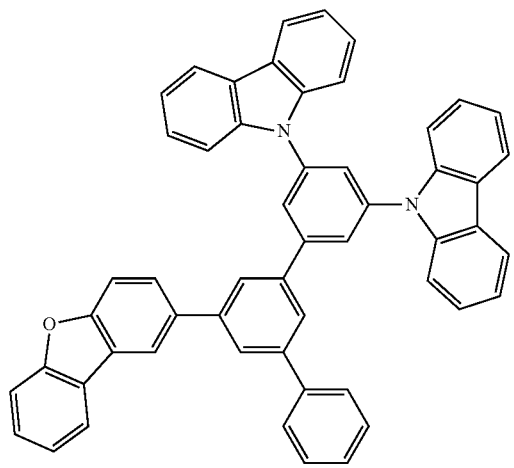

No. 4

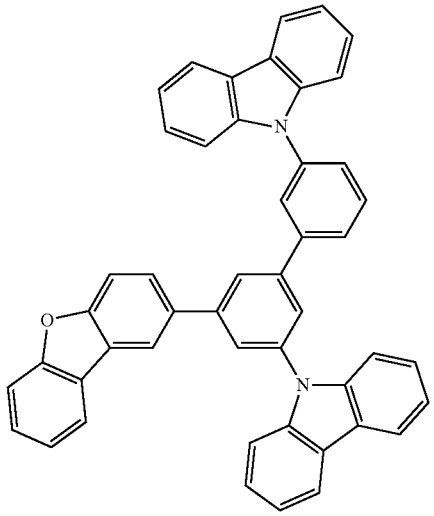

No. 5
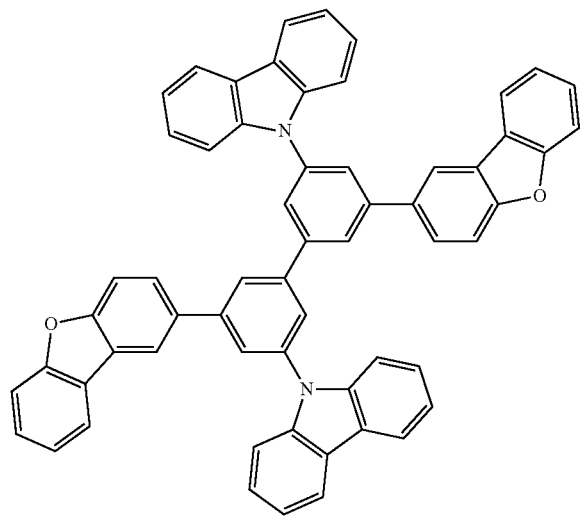
No. 8
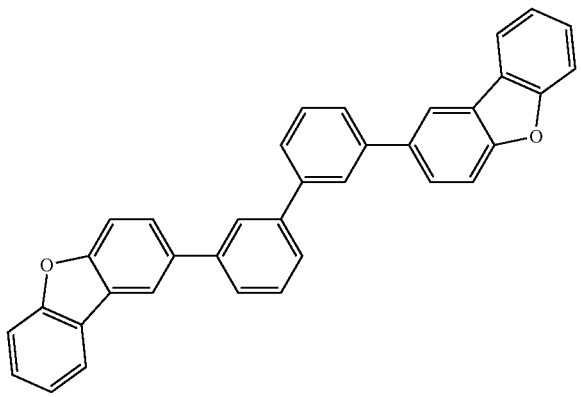
No. 6
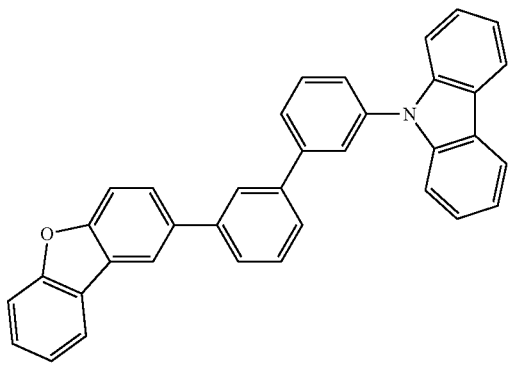
No. 9
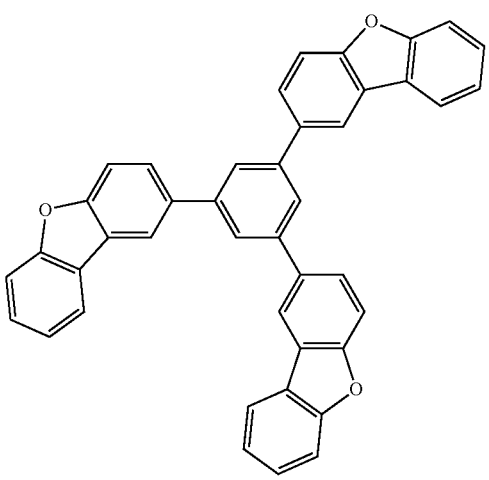
No. 7
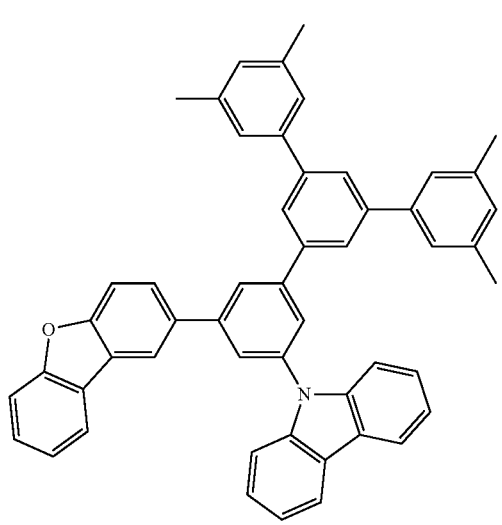
No. 10
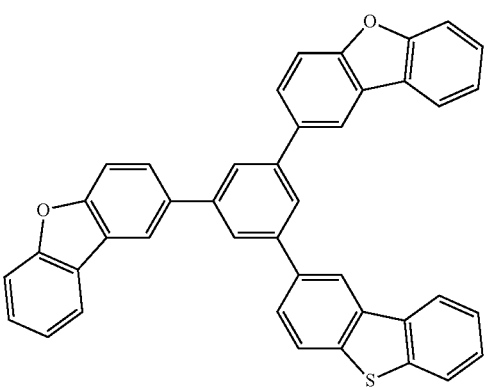

No. 11
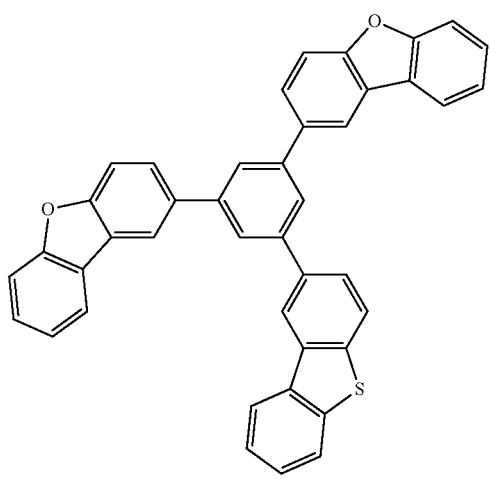
No. 12
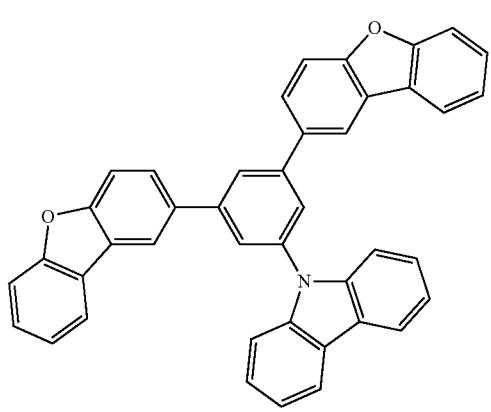
No. 13
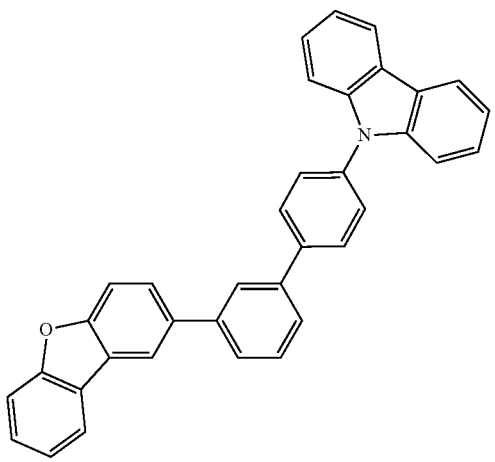
No. 14
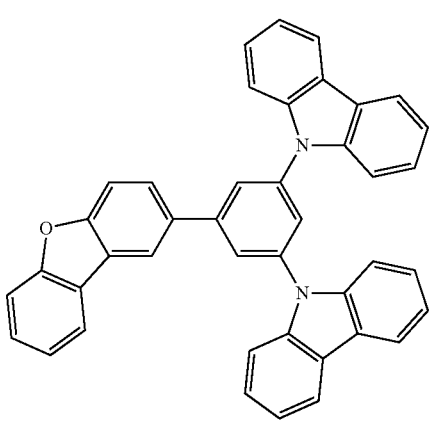
No. 15
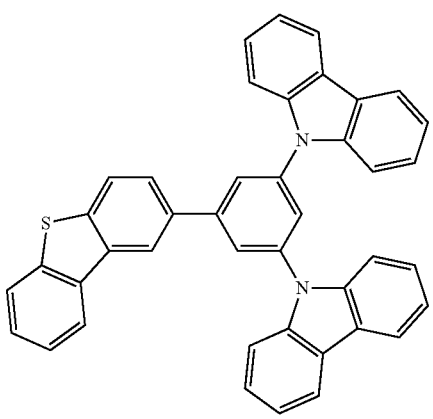
No. 16
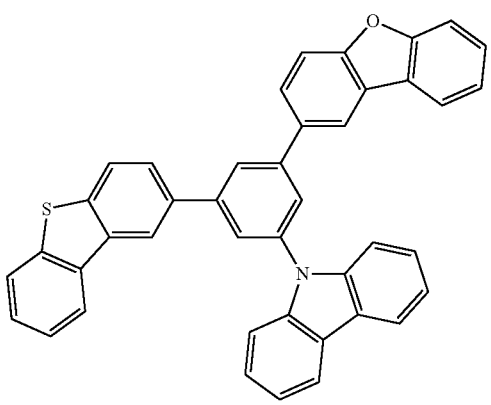

No. 17
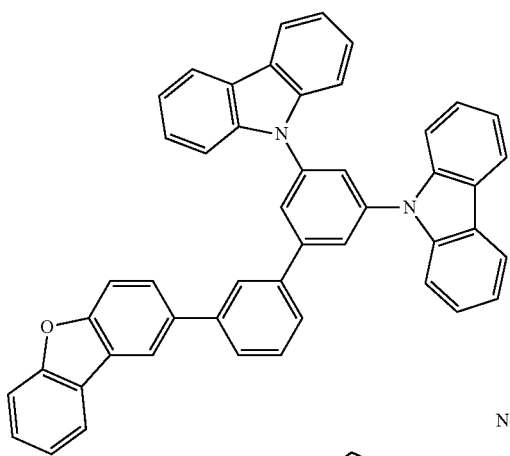
No. 18
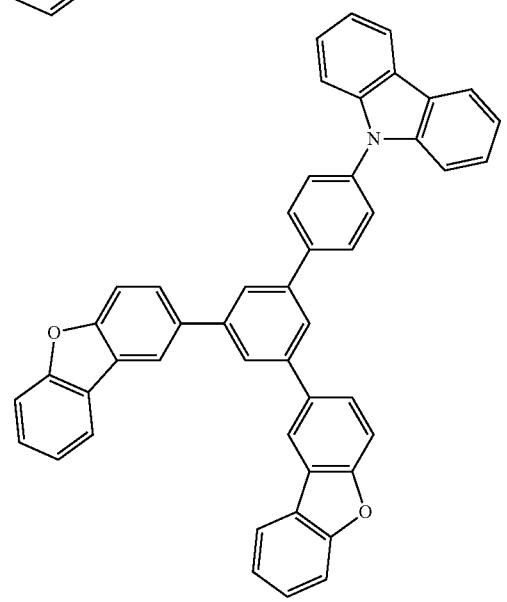
No. 19
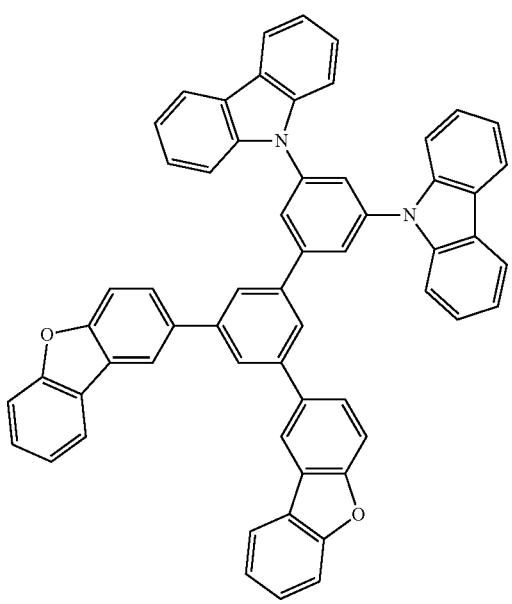
No. 20
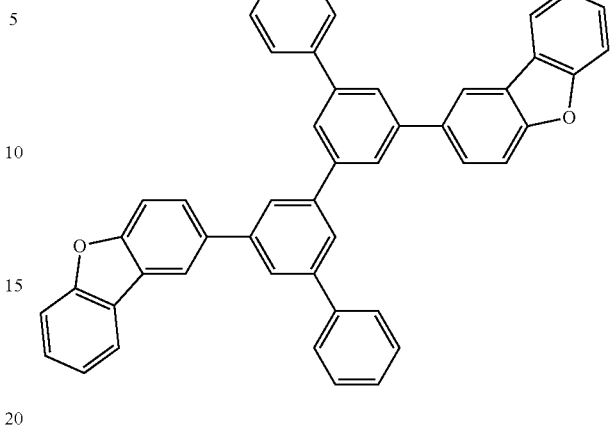
No. 21
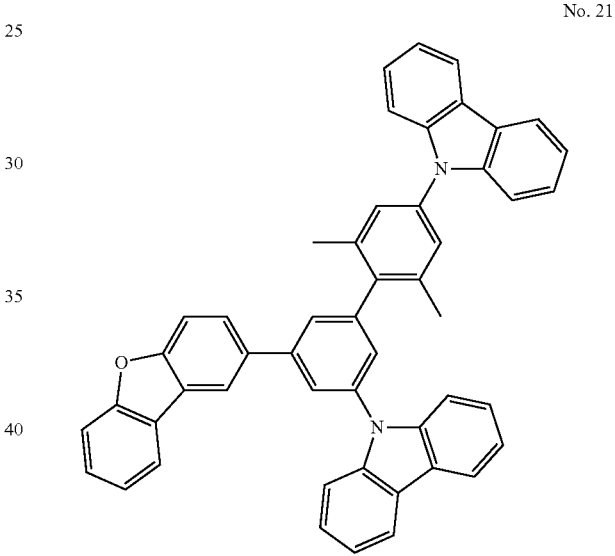
No. 22
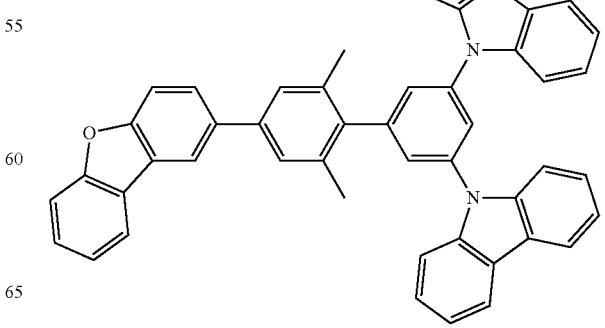

No. 23
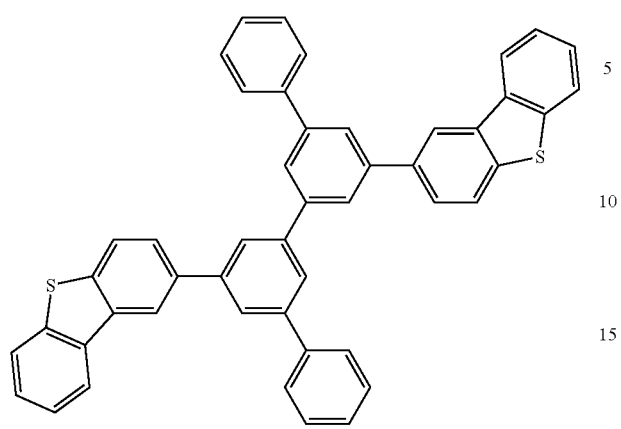
No. 24
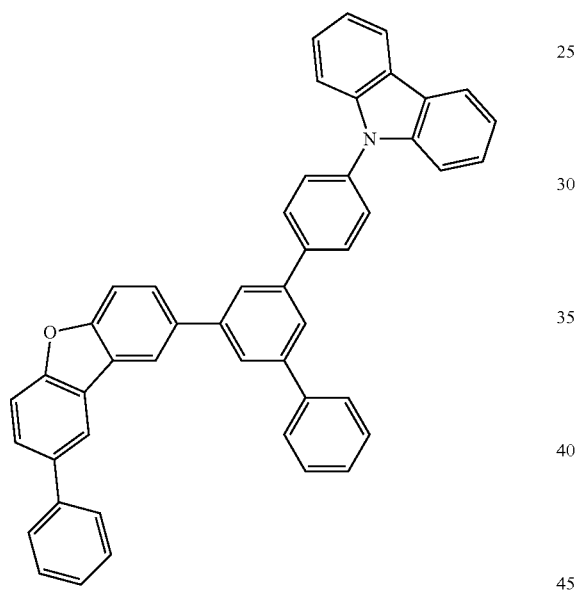
No. 25
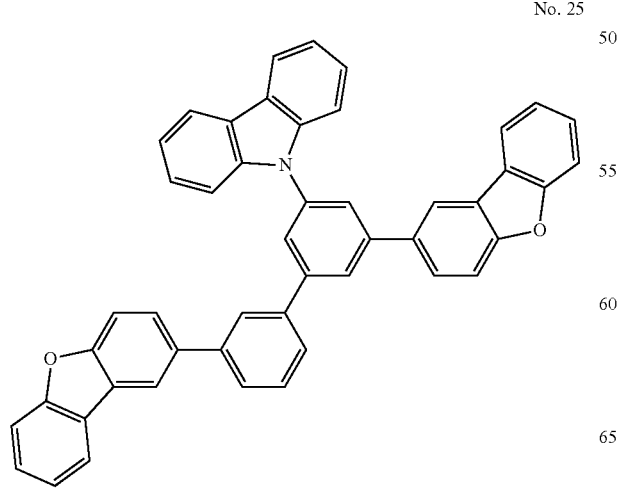
No. 26
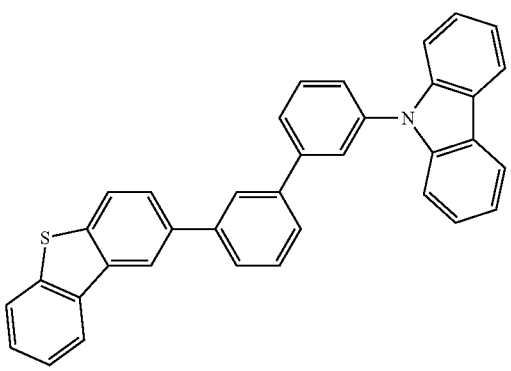
No. 27
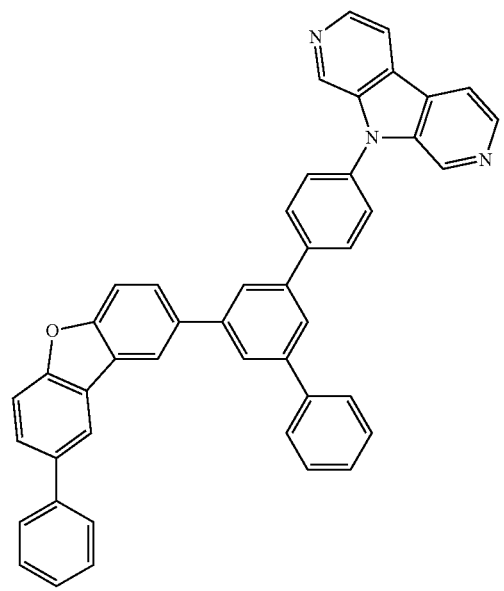
No. 28
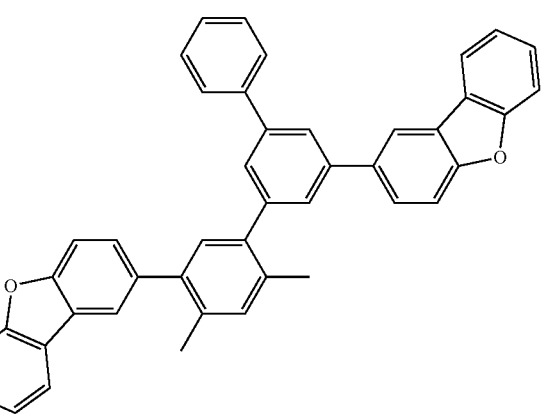

No. 29
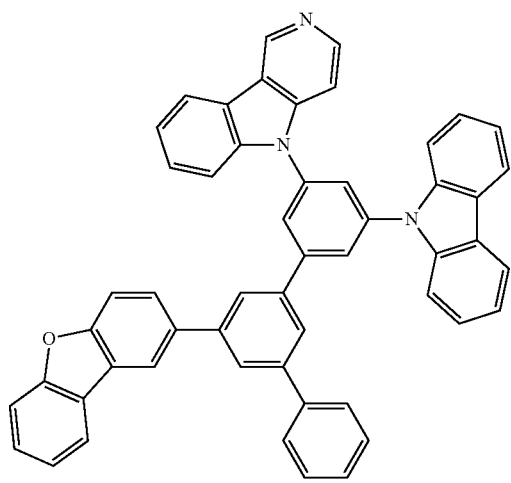
No. 30
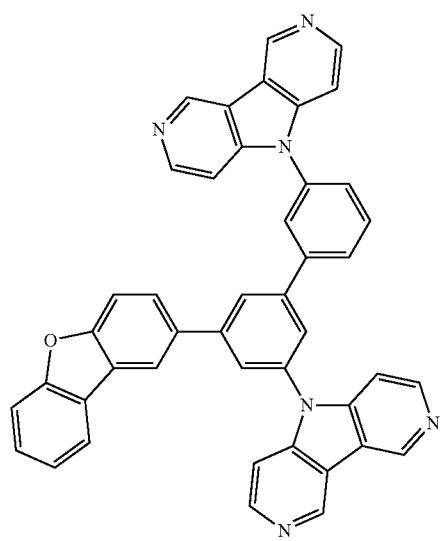
No. 31
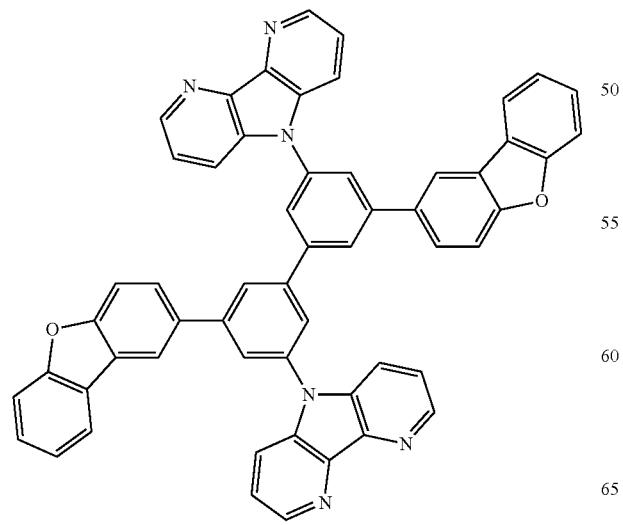
No. 32
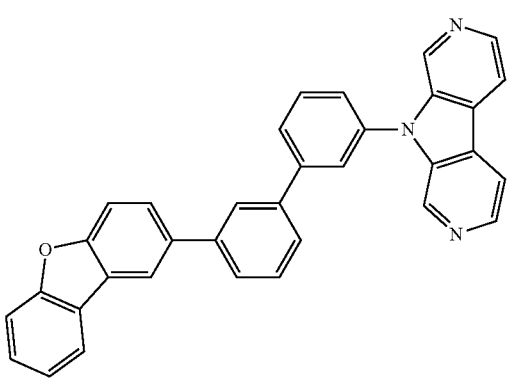
No. 33
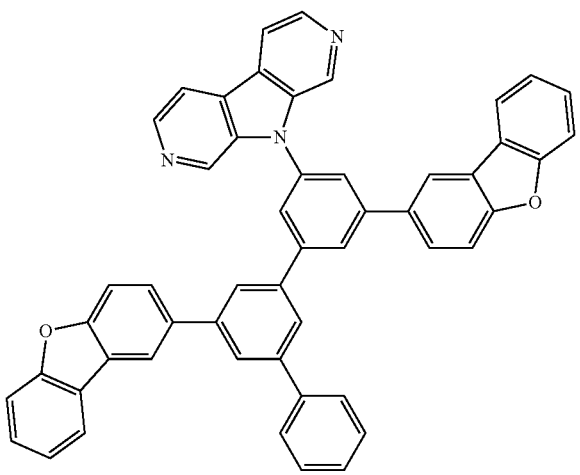
No. 34
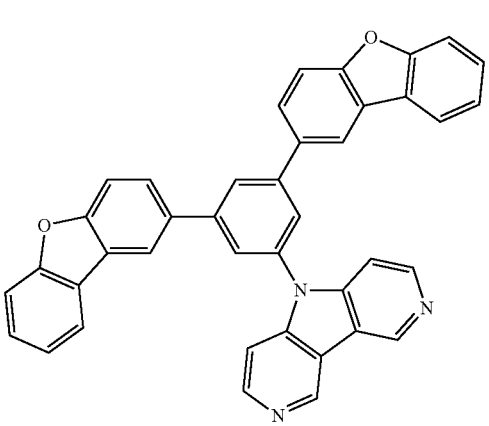

No. 35
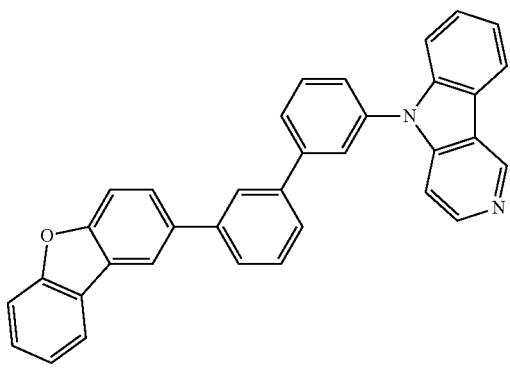
No. 36
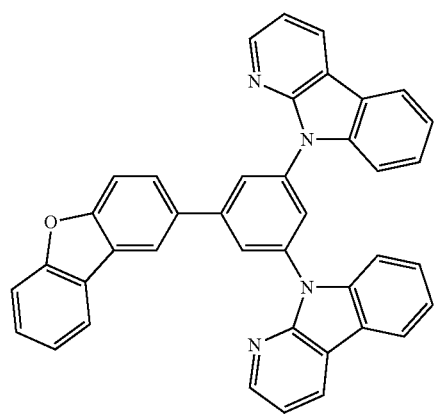
No. 37
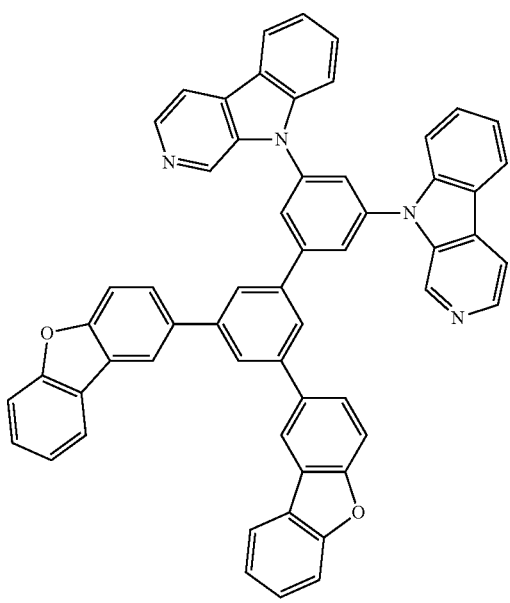
No. 38
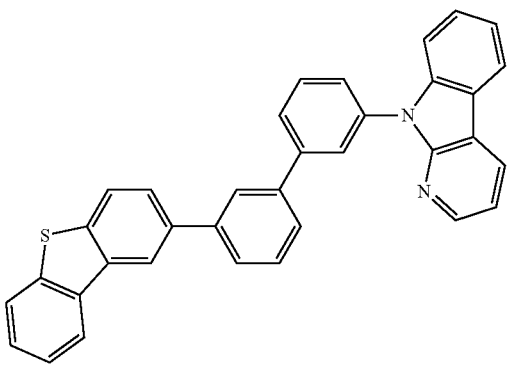
No. 39
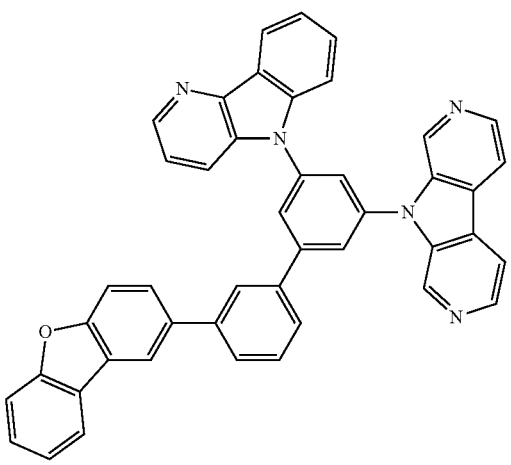
No. 40
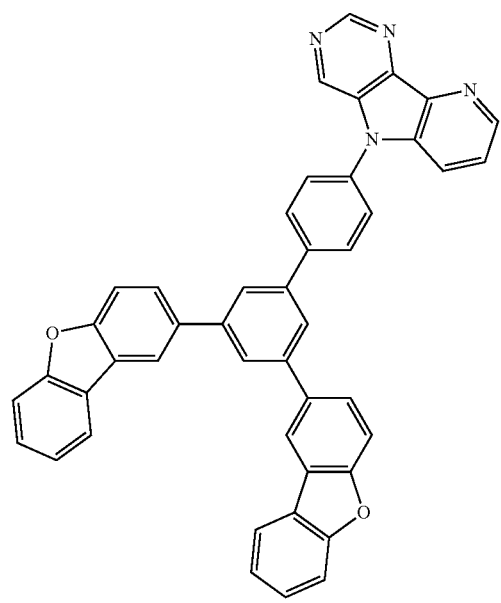

No. 41
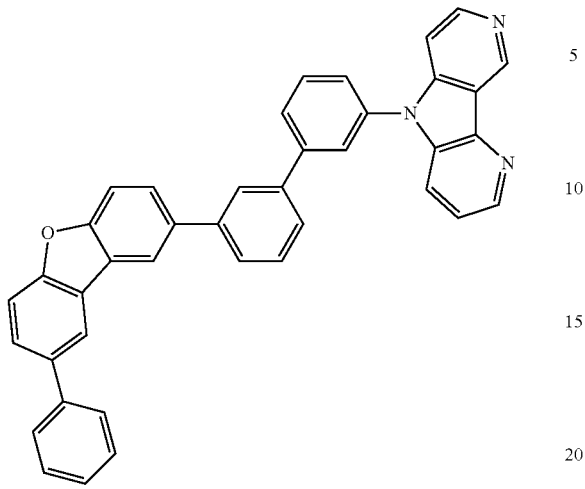
No. 42
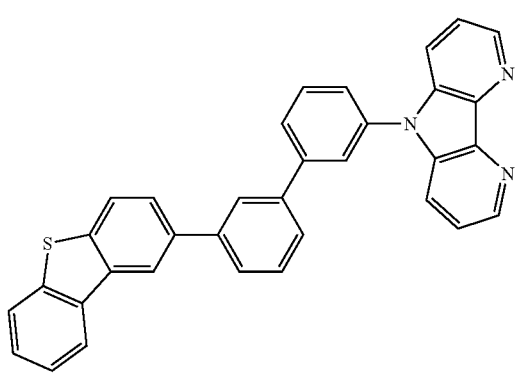
No. 43
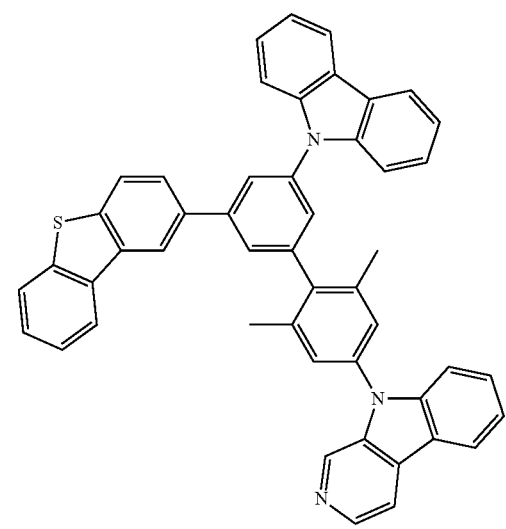
No. 44
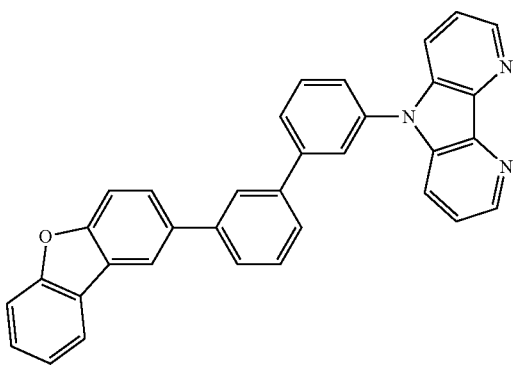
No. 45
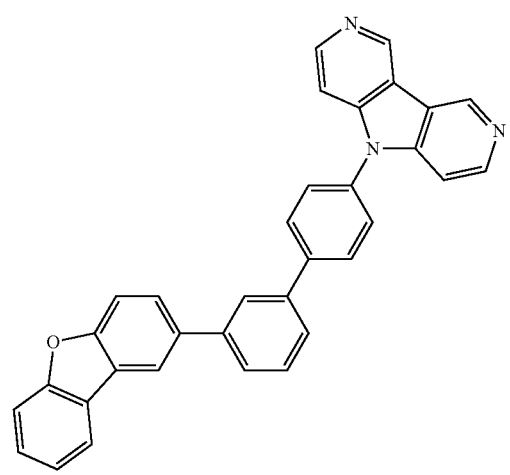
No. 46
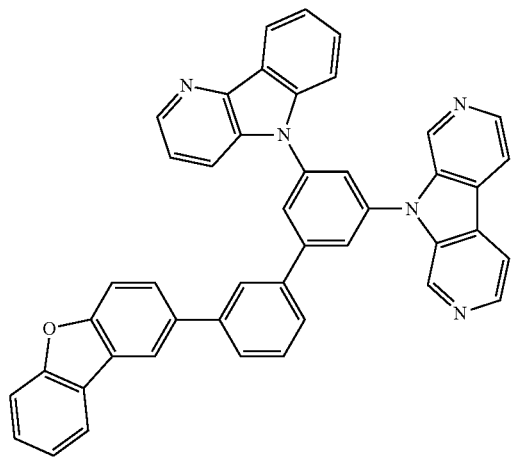

No. 47
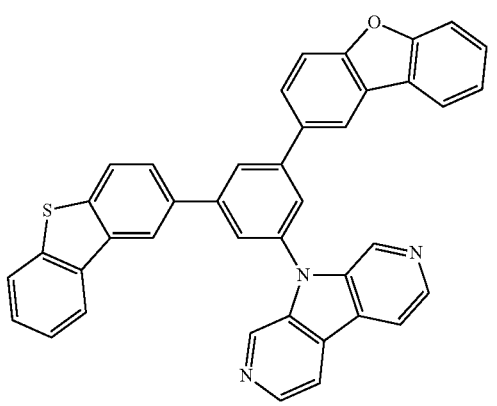
No. 48
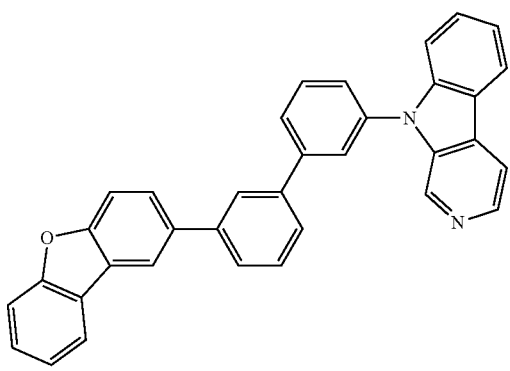
No. 49
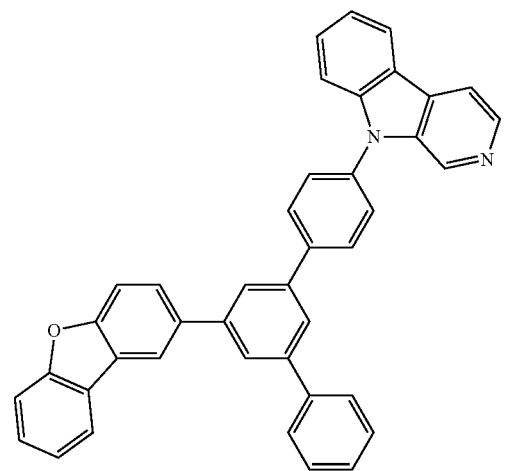
No. 50
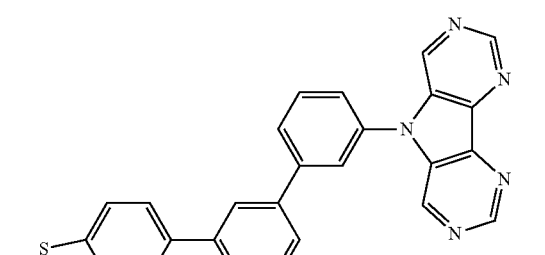
No. 51
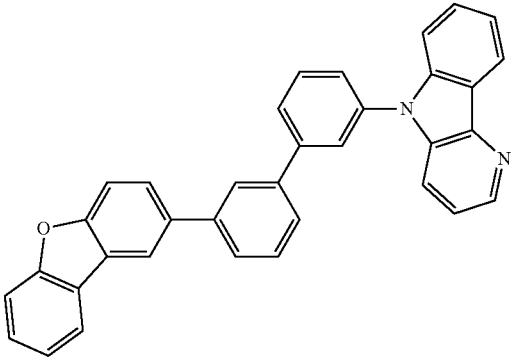
No. 52
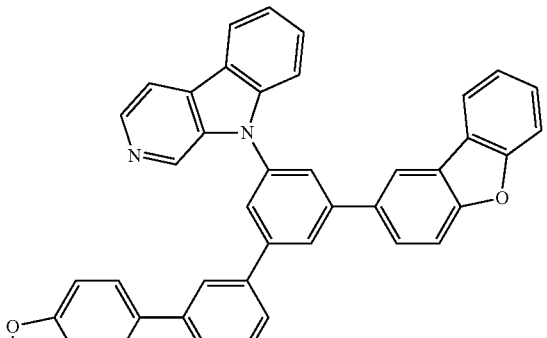
No. 53
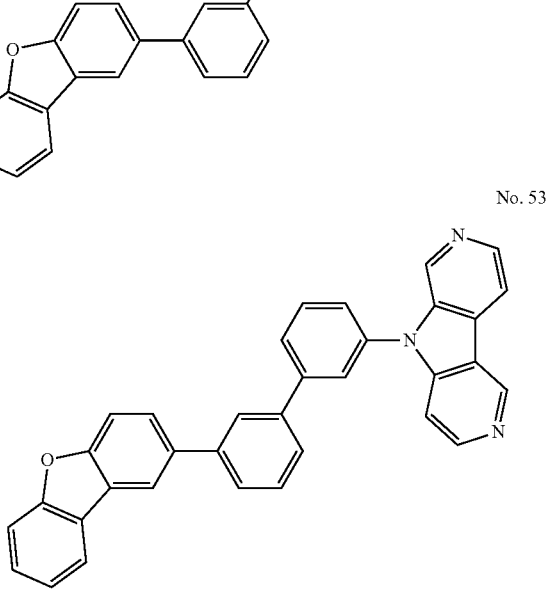

No. 54
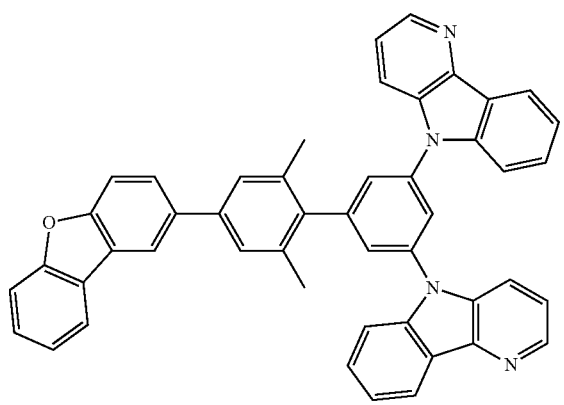
No. 55
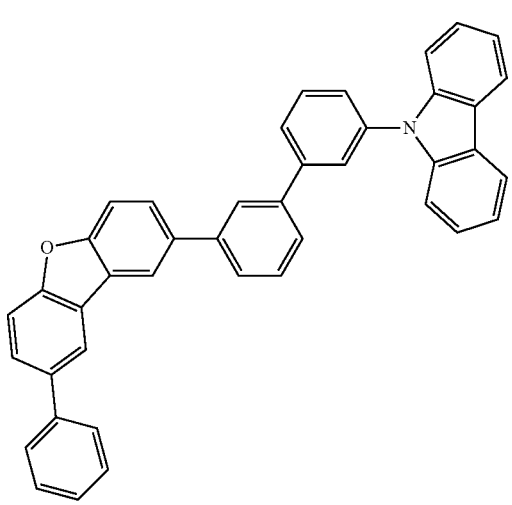
No. 56
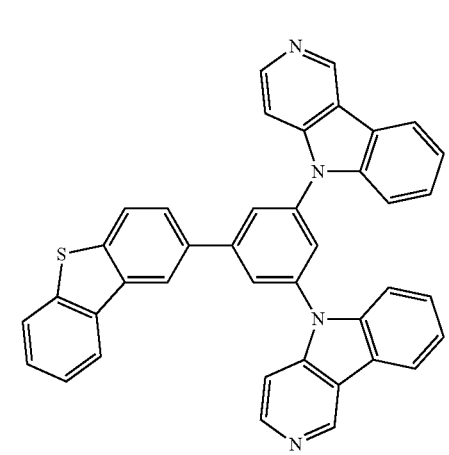
No. 57
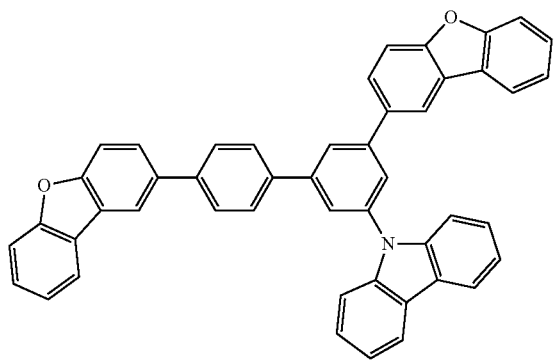
No. 58
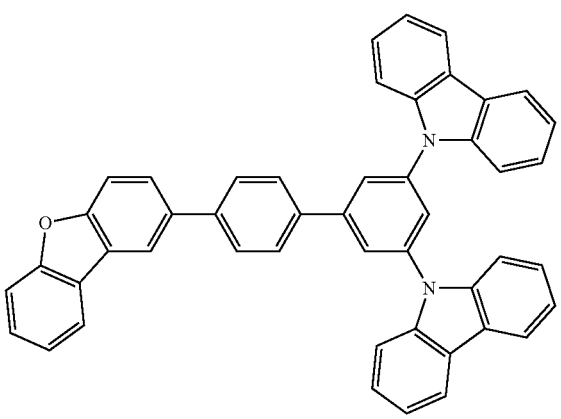
No. 59
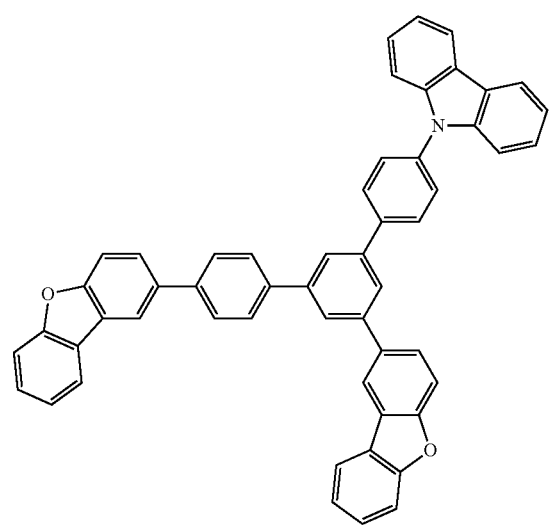
No. 60
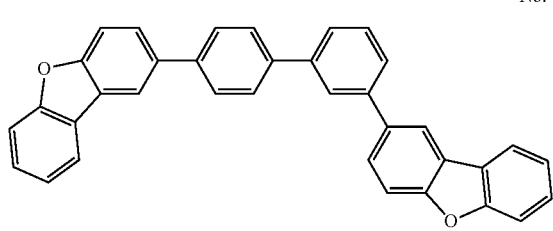

No. 61
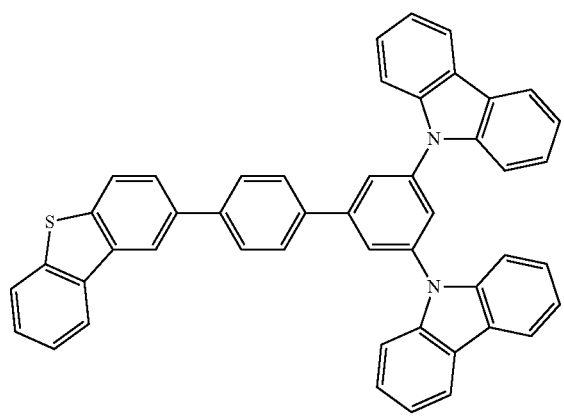
No. 62
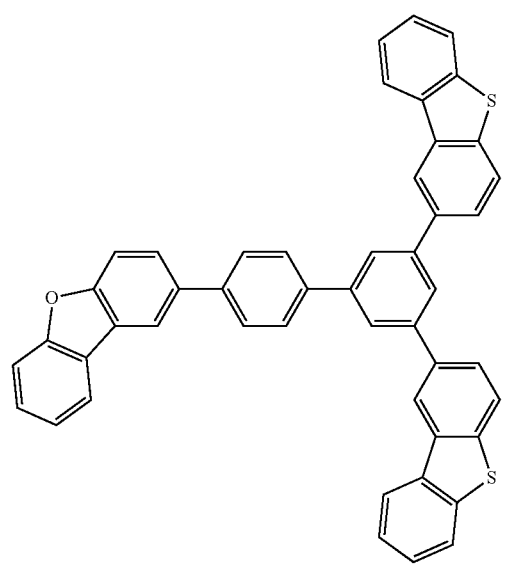
No. 63
No. 64
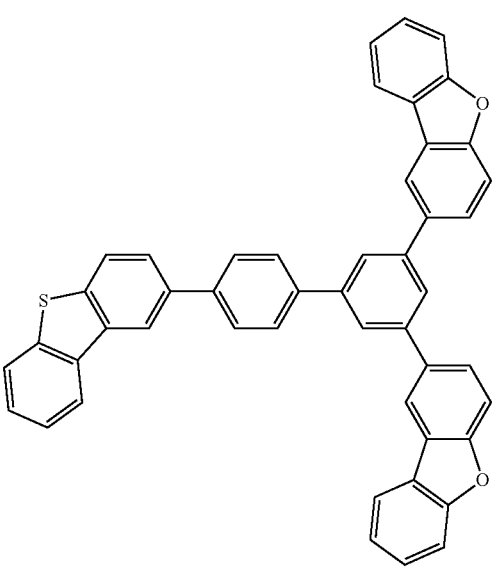
No. 65
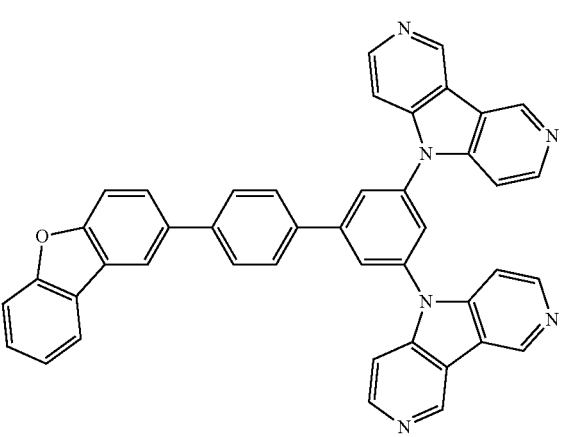
No. 66
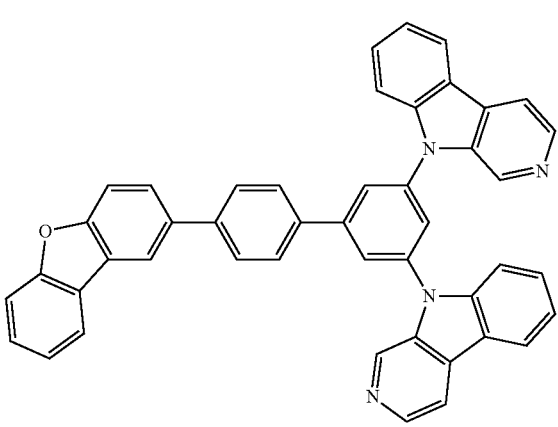

No. 67
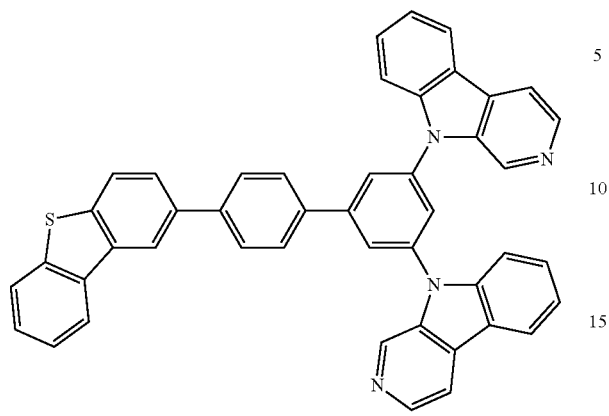
No. 68
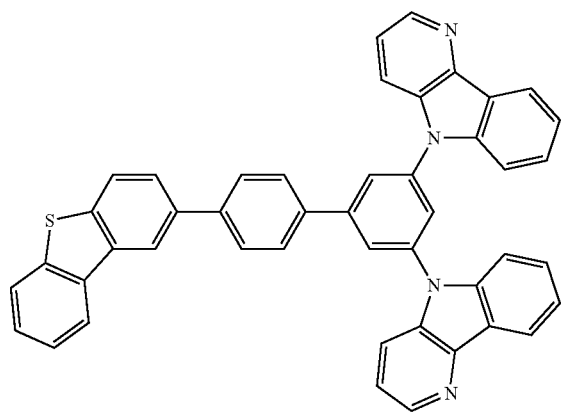
No. 69
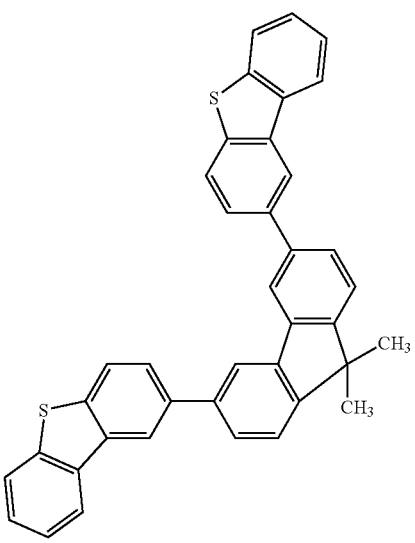
No. 70
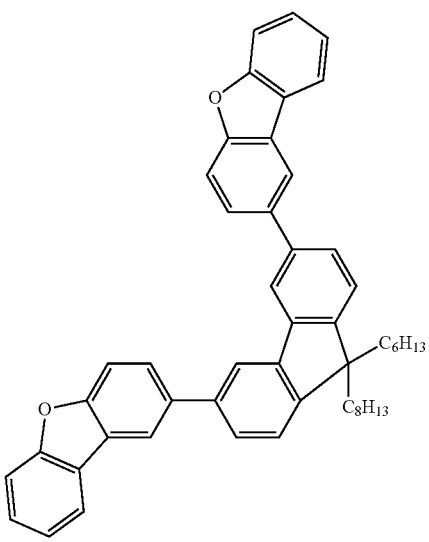
No. 71
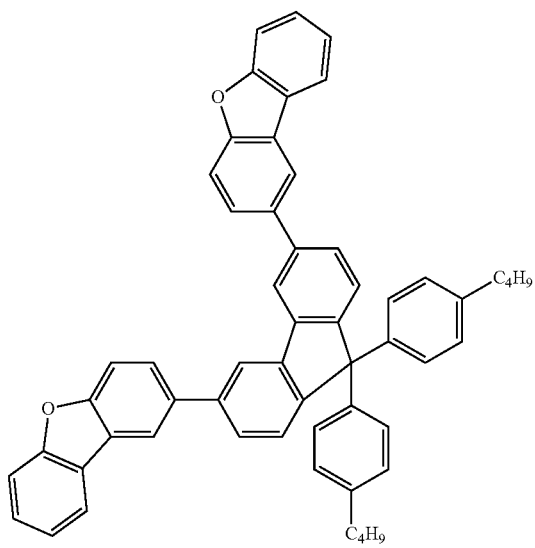
No. 72
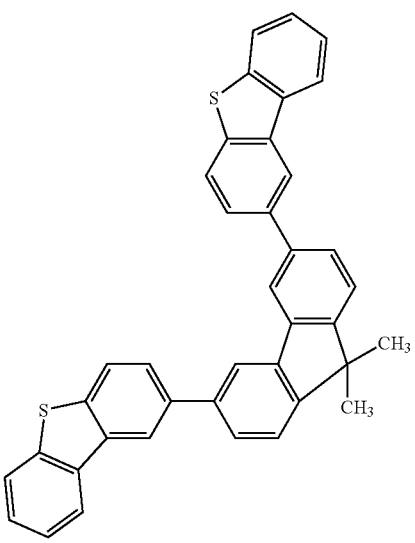

No. 73
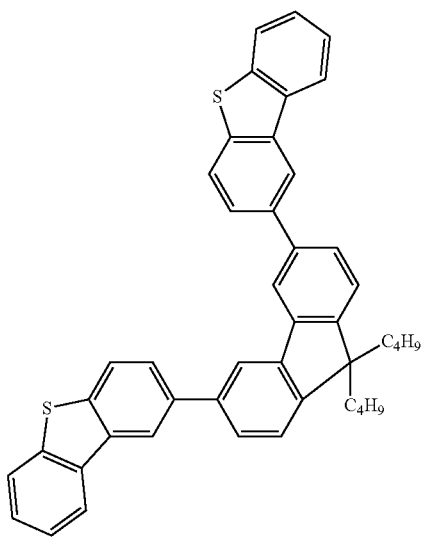
No. 74
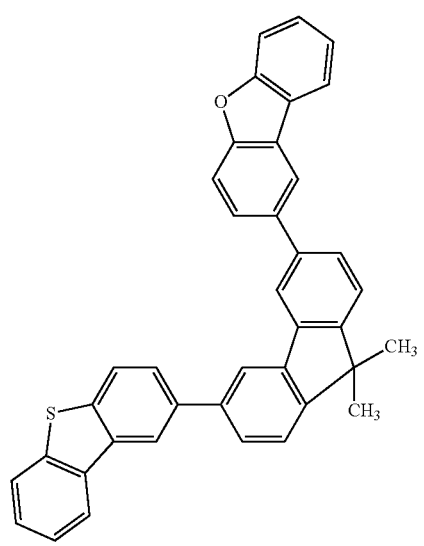
No. 75
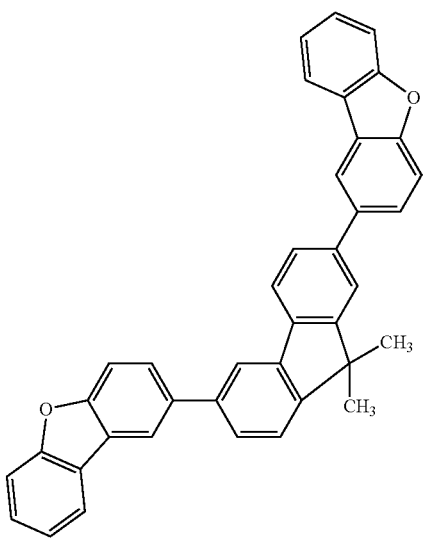
No. 76
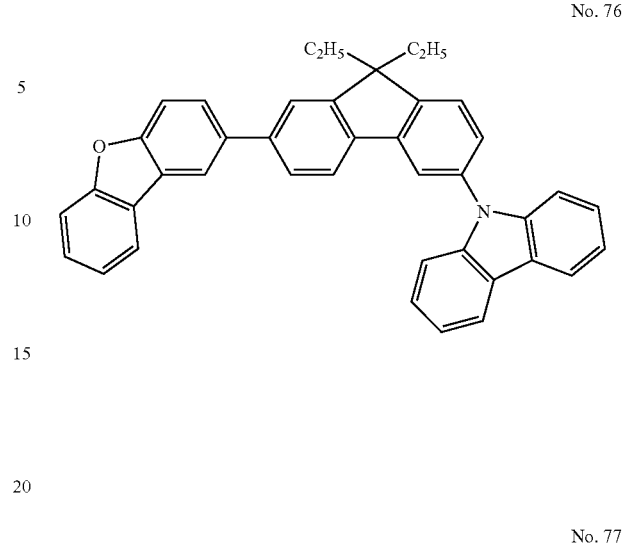
No. 77
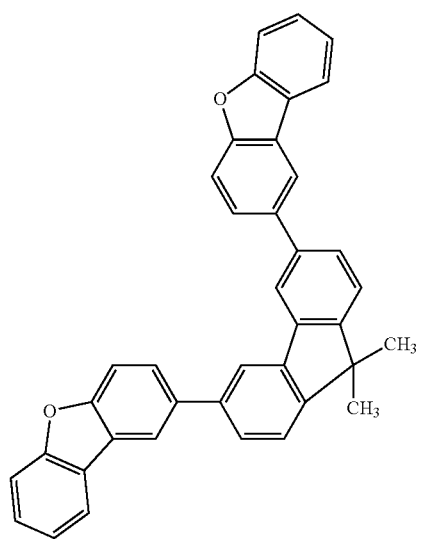
No. 78
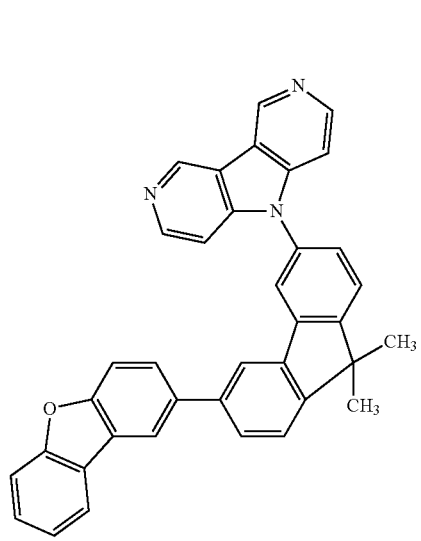

No. 79
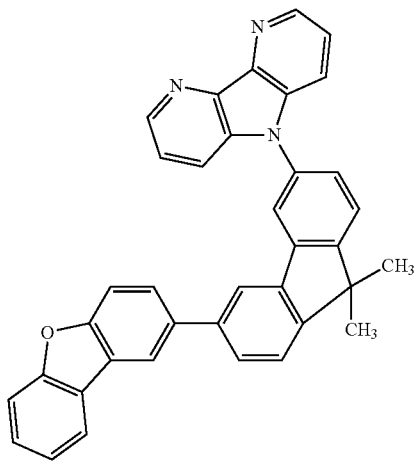
No. 82
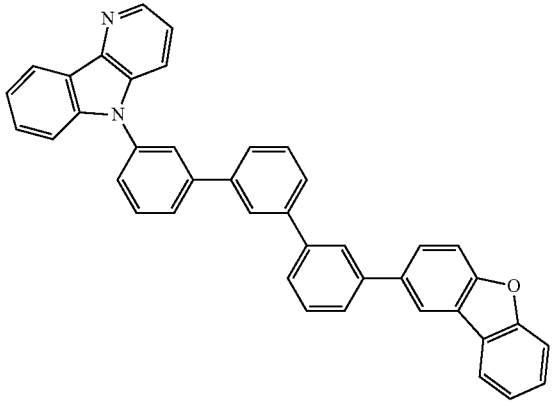
No. 80
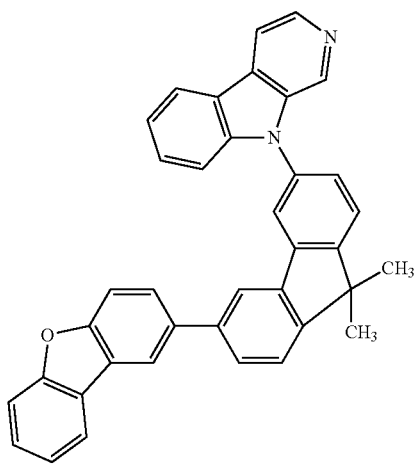
No. 83
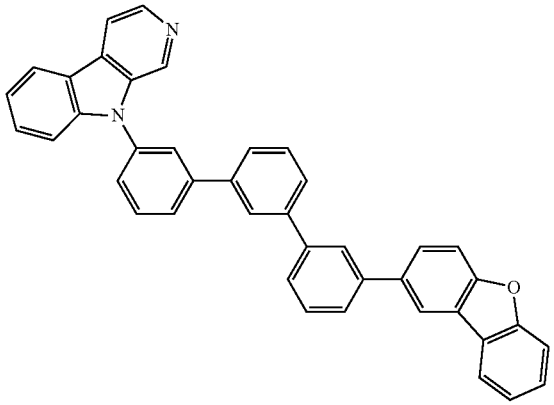
No. 81
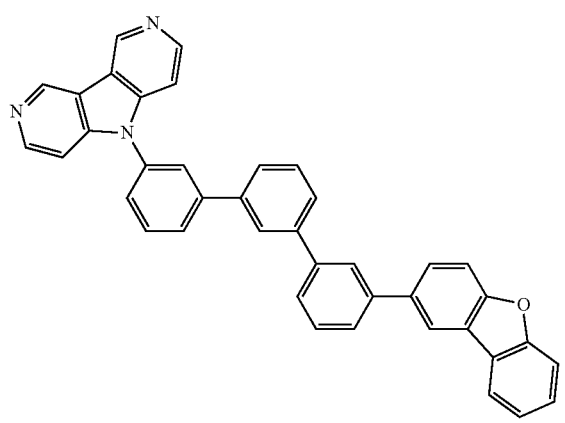
No. 84
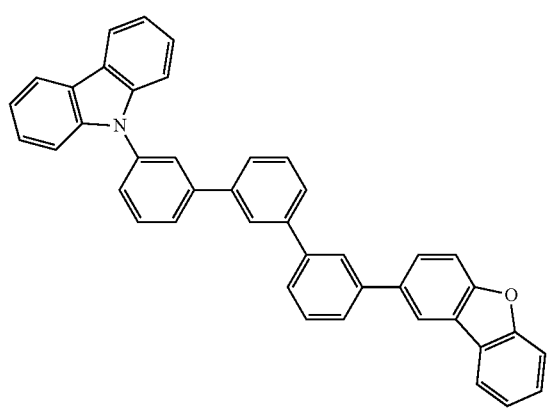

No. 85
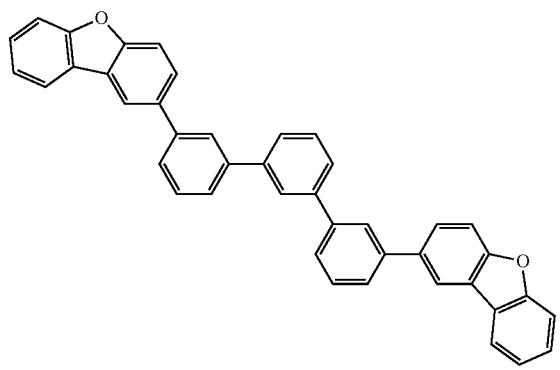
No. 86
No. 87
No. 88
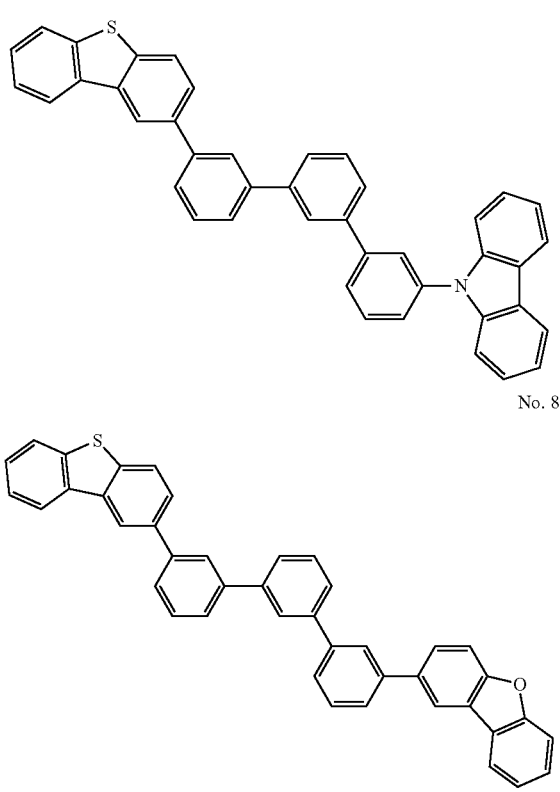
No. 89
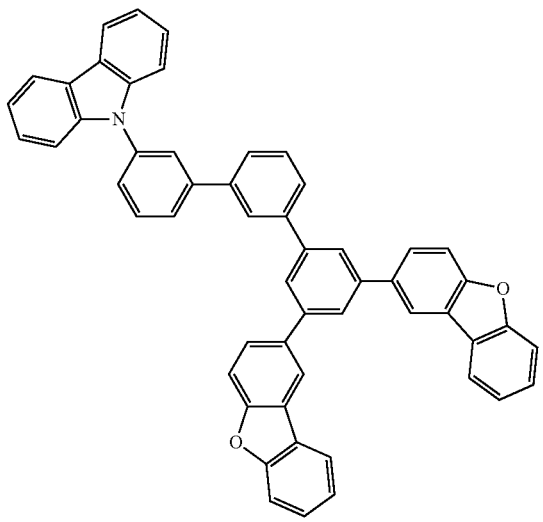
No. 90
No. 91
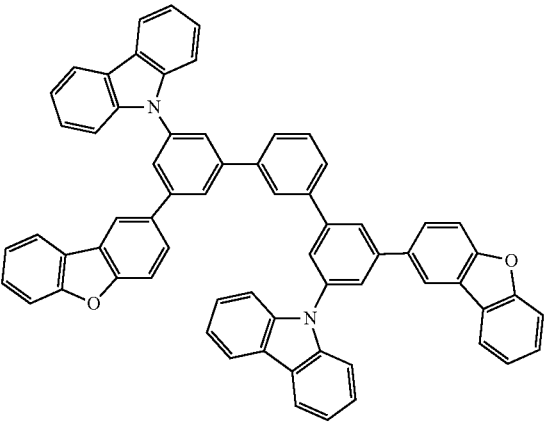

No. 92
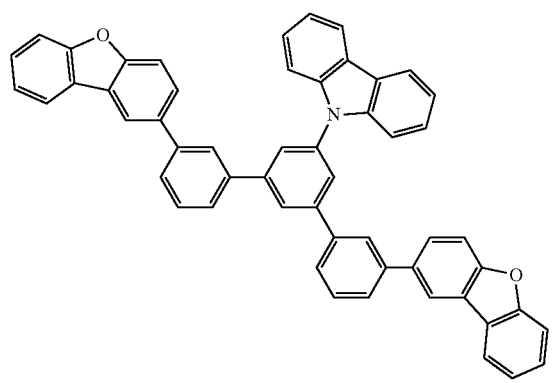
No. 93
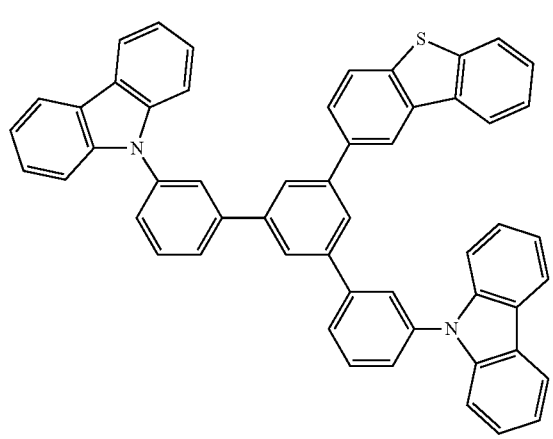
No. 94
No. 95
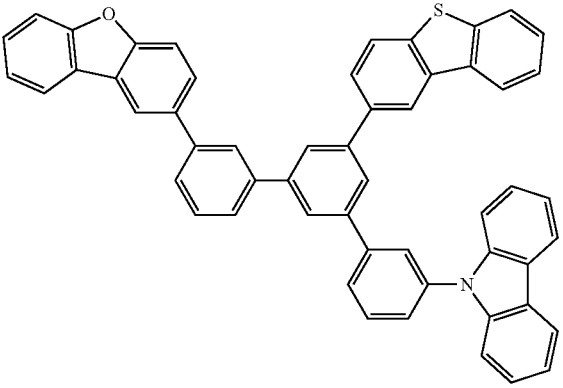
No. 96
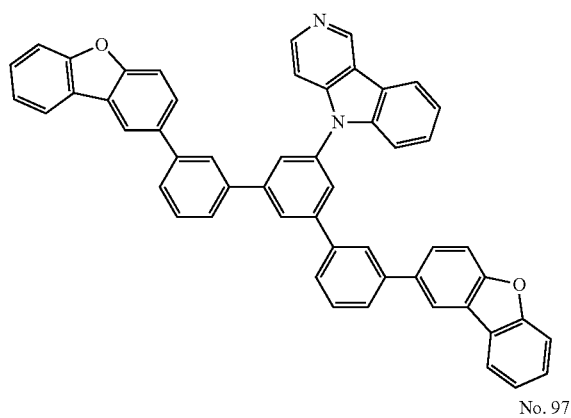
No. 97
No. 98
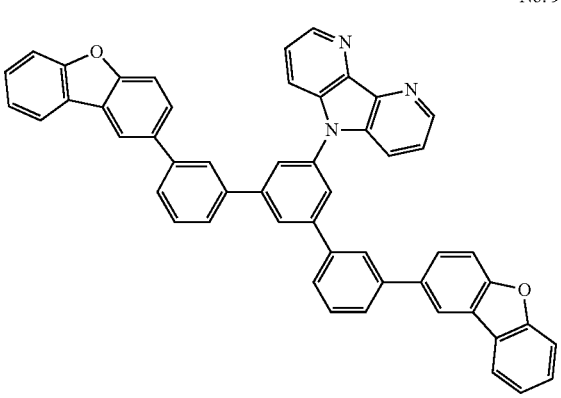

No. 99

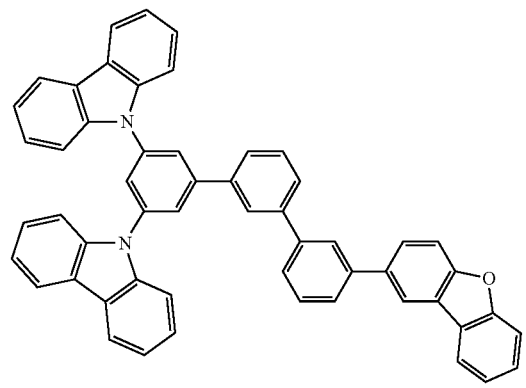

No. 100

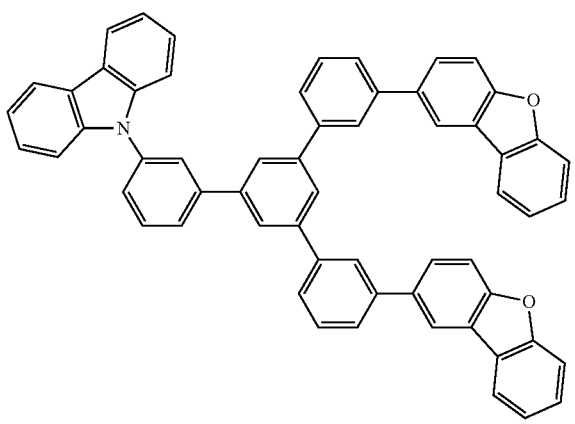

No. 101

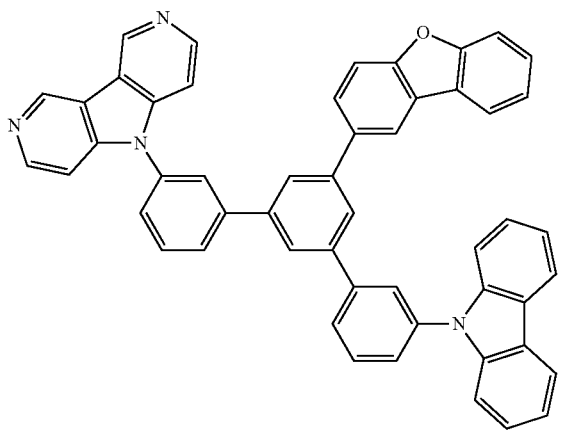

The compounds of the formula 1 may be easily synthesized by Suzuki-Miyaura reaction between an organic boronic acid and an aryl halide according to the following reaction scheme.

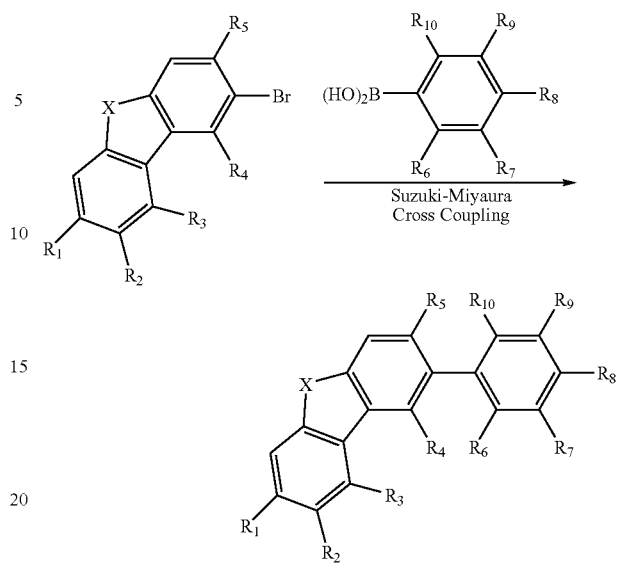

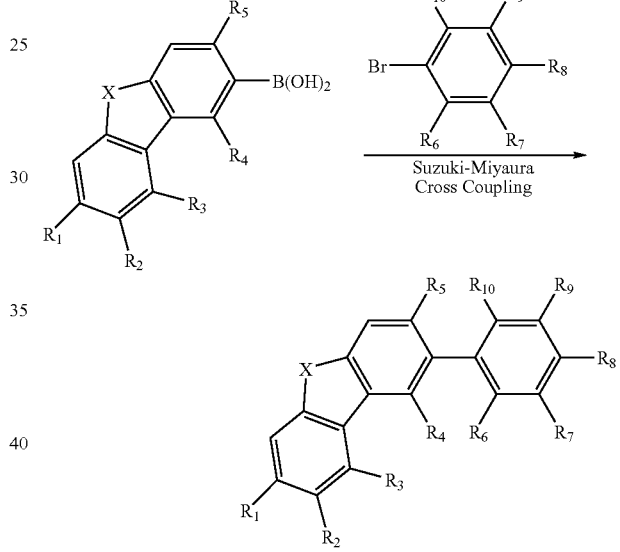

The material for organic EL devices of the present invention are preferably used as the host material for the light emitting layer of organic EL devices.

The organic EL devices of the present invention will be described below. The organic EL devices have an organic thin film having one or more layers between the cathode and the anode. At least one of the layers of the organic thin film is a light emitting layer. At least one layer of the organic thin film contains the material for organic EL devices of the present invention.

The multi-layered organic EL devices have a multi-layered laminate structure such as anode/hole transport layer (hole injection layer)/light emitting layer/cathode, anode/light emitting layer/electron transport layer (electron injection layer)/cathode, anode/hole transport layer (hole injection layer)/light emitting layer/electron transport layer (electron injection layer)/cathode, and anode/hole transport layer (hole injection layer)/light emitting layer/hole barrier layer/electron transport layer (electron injection layer)/cathode.

The light emitting layer of the organic EL devices preferably contains the material for organic EL devices as the host material. Further, the light emitting layer comprises a host material, preferably the material for organic EL devices, and a phosphorescent light emitting material. Preferred examples of the phosphorescent light emitting material are compounds containing iridium (Ir), osmium (Os) or platinum (Pt) because of their high quantum yield of phosphorescence and their capability of enhancing the external quantum efficiency of light emitting devices, with metal complexes such as iridium complexes, osmium complexes and platinum complexes being more preferred, iridium complexes and platinum complexes being still more preferred, and ortho-metallated iridium complexes being most preferred. Preferred examples of the ortho-metallated iridium complexes are shown below.

(K-1)
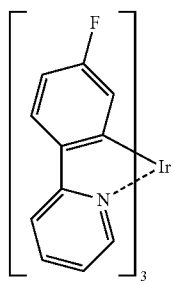

(K-2)
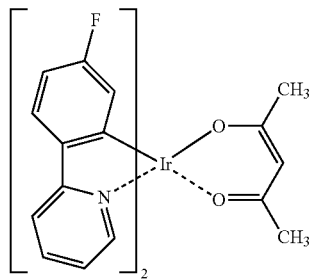

(K-3)
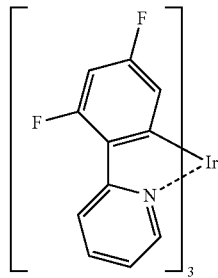

(K-4)
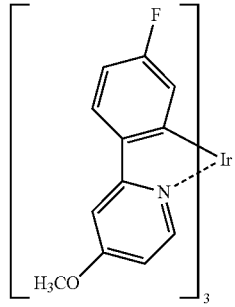

(K-5)
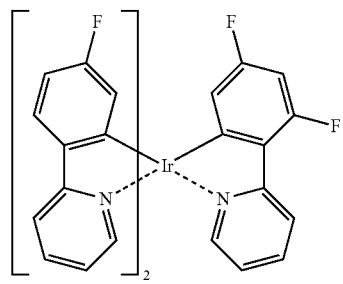

(K-6)
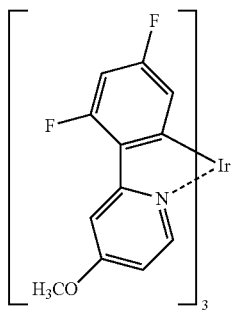

(K-7)
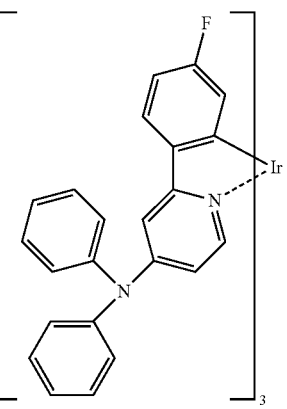

(K-8)
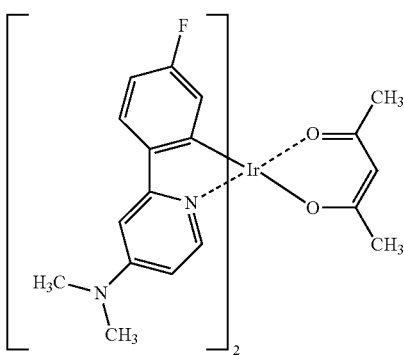

(K-9) 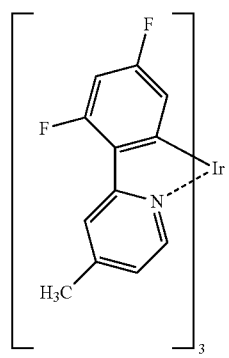
(K-10) 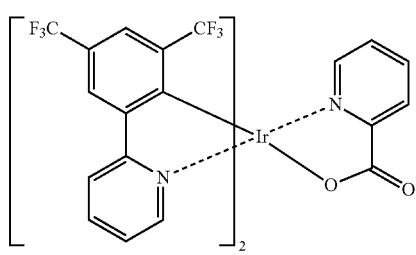
(K-11) 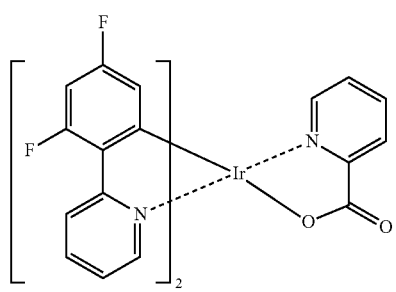
(K-12) 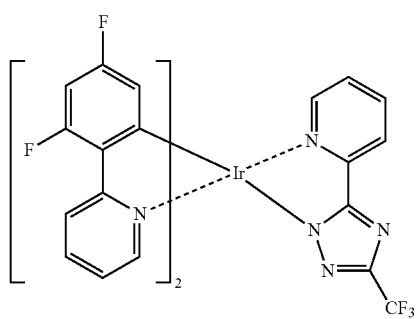
(K-13) 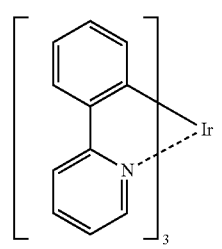
(K-14) 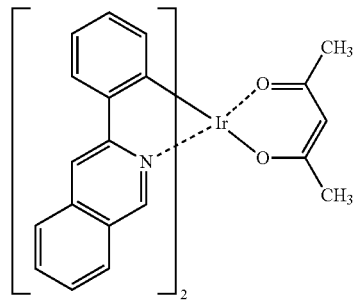
(K-15) 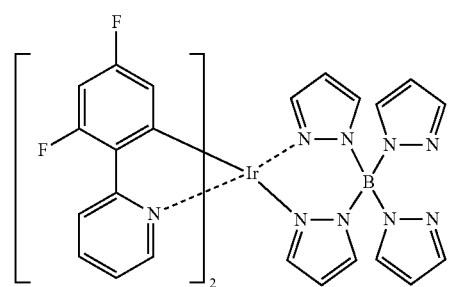
(K-16) 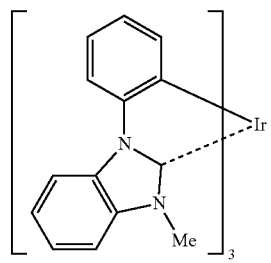
(K-17) 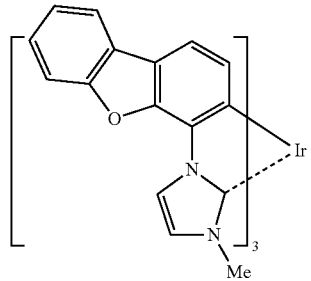
(K-18) 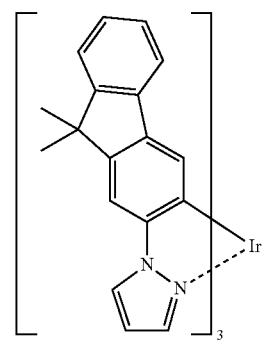

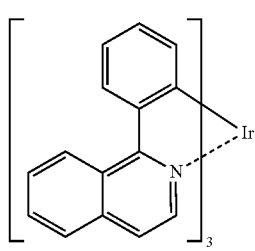
(K-19)

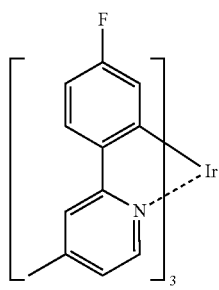
(K-20)

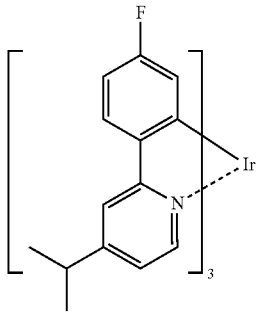
(K-21)

In another preferred embodiment of the organic EL devices, the light emitting layer contains the host material and a phosphorescent light emitting material, for example, a blue-light emitting metal complex having a maximum emitting wavelength of 500 nm or less. Examples of the blue-light emitting metal complex include K-1, K-2, K-3, K-10, K-11, K-12, K-15, K-16, K-17, K-20, and K-21 described above.

Still another preferred organic EL device includes a hole transport layer (hole injection layer) which contains the material for organic EL devices of the invention. Still another preferred organic EL device includes an electron transport layer and/or hole barrier layer, wherein either or both layers contain the material for organic EL devices of the invention.

In the organic EL devices of the invention, a reducing dopant is preferably added to the interfacial region between the cathode and the organic thin film layer. Examples of the reducing dopant include at least one compound selected from alkali metals, alkali metal complexes, alkali metal compounds, alkaline earth metals, alkaline earth metal complexes, alkaline earth metal compounds, rare earth metals, rare earth metal complexes, and rare earth metal compounds.

Examples of the alkali metals include Na (work function: 2.36 eV), K (work function: 2.28 eV), Rb (work function: 2.16 eV), and Cs (work function: 1.95 eV), with those having a work function of 2.9 eV or less being particularly preferred. Preferred is K, Rb or Cs, more preferred is Rb or Cs, and most preferred is Cs.

Examples of the alkaline earth metals include Ca (work function: 2.9 eV), Sr (work function: 2.0 to 2.5 eV), and Ba (work function: 2.52 eV), with those having a work function of 2.9 eV or less being particularly preferred.

Examples of the rare earth metals include Sc, Y, Ce, Tb and Yb, with those having a work function of 2.9 eV or less being particularly preferred.

Particularly, the preferred metals mentioned above have a high reducing ability. Therefore, a relatively small amount of addition thereof to the electron injection zone improves the luminance of emission and prolongs the lifetime.

Examples of the alkali metal compounds include alkali oxides such as $Li_2O$, $Cs_2O$ and $K_2O$ and alkali halides such as LiF, NaF, CsF and KF, with LiF, $Li_2O$ and NaF being preferred.

Examples of the alkaline earth metal compounds include BaO, SrO, CaO and mixtures thereof such as $Ba_xSr_{1-x}O$ (0<x<1) and $Ba_xCa_{1-x}O$ (0<x<1), with BaO, SrO and CaO being preferred.

Examples of the rare earth metal compounds include $YbF_3$, $ScF_3$, $ScO_3$, $Y_2O_3$, $Ce_2O_3$, $GdF_3$ and $TbF_3$, with $YbF_3$, $ScF_3$ and $TbF_3$ being preferred.

The alkali metal complexes, alkaline earth metal complexes and rare earth metal complexes are not particularly limited as long as containing at lease one metal ions selected from alkali metal ions, alkaline earth metal ions and rare earth metal ions. Examples of the lingand preferably include, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridine, phenanthroline, phthalocyanine, porphyrin, cyclopentadiene, β-diketones, azomethines, and derivatives thereof.

The reducing dopant is added to the interfacial region preferably in the form of layers or islands by a resistance-heating vapor deposition in which the reducing dopant is vapor-deposited while vapor-depositing an organic material (a light emitting material or an electron injection material for forming the interfacial region) at the same time, thereby dispersing the reducing dopant in the organic material. The dispersion concentration is 100:1 to 1:100, preferably 5:1 to 1:5 when expressed by a molar ratio of the organic material to the reducing dopant.

When adding the reducing dopant in the form of layer, the reducing dopant is solely vapor-deposited by the resistance-heating vapor deposition into a layer preferably having a thickness of 0.1 to 15 nm after forming an interfacial organic layer from a light emitting material or an electron injection material.

When adding the reducing dopant in the form of islands, the reducing dopant is solely vapor-deposited by the resistance-heating vapor deposition into a form of islands preferably having a thickness of 0.05 to 1 nm after forming an interfacial organic layer from a light emitting material or an electron injection material.

The molar ratio of the main components of the organic EL devices of the invention (light emitting material and electron injection material) and the reducing dopant is preferably 5:1 to 1:5 and more preferably 2:1 to 1:2.

In still another preferred embodiment of the invention, the organic EL device has an electron injection layer between the light emitting layer and the cathode, and the electron injection layer mainly comprises a nitrogen-containing cyclic derivative. The electron transport material for the electron injection layer is preferably an aromatic heterocyclic compound having one or more heteroatoms in its molecule, particularly an aromatic nitrogen-containing cyclic compound.

For example, the aromatic nitrogen-containing cyclic compound is preferably a nitrogen-containing, cyclic metal chelate complex represented by the following formula A:

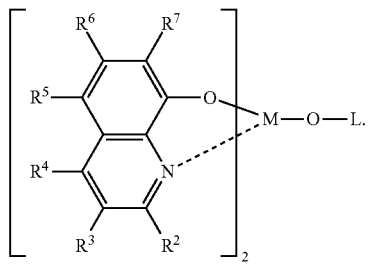
(A)

In the formula A, $R^2$ to $R^7$ are each independently hydrogen atom, halogen atom, oxy group, or amino group or hydrocarbon group having 1 to 40 carbon atoms, each being operationally substituted.

Examples of the halogen atom are the same as mentioned above. Examples of the amino group which is operationally substituted include the same groups which are recited as the alkylamino group, arylamino group, and aralkylamino group mentioned above.

Example of the hydrocarbon group having 1 to 40 carbon atoms include alkyl group, alkenyl group, cycloalkyl group, alkoxy group, aryl group, heterocyclic group, aralkyl group, aryloxy group, and alkoxycarbonyl group, each being optionally substituted. Examples of the alkyl group, alkenyl group, cycloalkyl group, alkoxy group, aryl group, heterocyclic group, aralkyl group, and aryloxy group are the same as those mentioned above. The alkoxycarbonyl group is represented by —COOY' wherein Y' is the same alkyl group as mentioned above.

M in the formula A is aluminum (Al), gallium (Ga) or indium (In), with In being preferred.

L in the formula A is a group represented by the following formula A' or

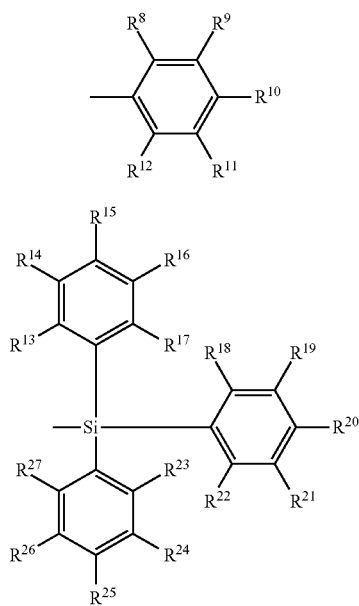
(A')
(A")

wherein $R^8$ to $R^{12}$ are each independently hydrogen atom or hydrocarbon group having 1 to 40 carbon atoms which is optionally substituted, the groups adjacent to each other optionally forming a ring structure. $R^{13}$ to $R^{27}$ are each independently hydrogen atom or hydrocarbon group having 1 to 40 carbon atoms which is optionally substituted, the groups adjacent to each other optionally forming a ring structure.

Examples of the hydrocarbon group having 1 to 40 carbon atoms of the formulae A' and A" are the same groups as those recited for $R^2$ to $R^7$. Examples of the bivalent group which is formed by the adjacent groups of $R^8$ to $R^{12}$ or $R^{13}$ to $R^{27}$ for forming a ring structure include tetramethyle group, pentamethyle group, hexamethyle group, diphenylmethane-2,2'-diyl group, diphenylethane-3,3'-diyl group, and diphenylpropane-4,4'-diyl group.

Specific examples of the nitrogen-containing, cyclic metal chelate complex are shown below, although not limited thereto.

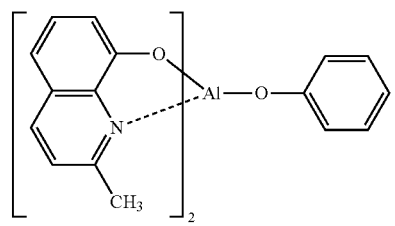
(A-1)

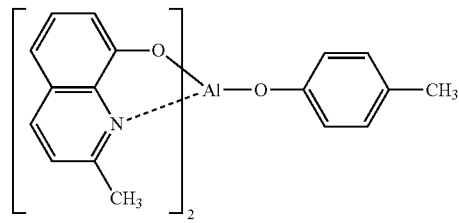
(A-2)

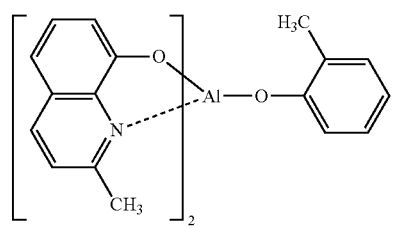
(A-3)

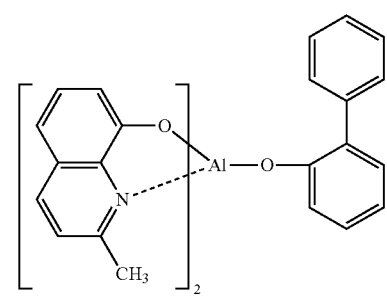
(A-4)

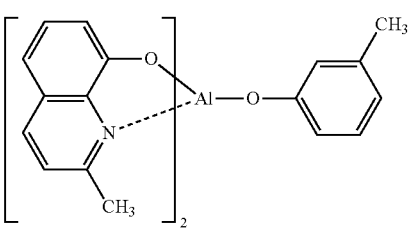
(A-5)

(A-6) 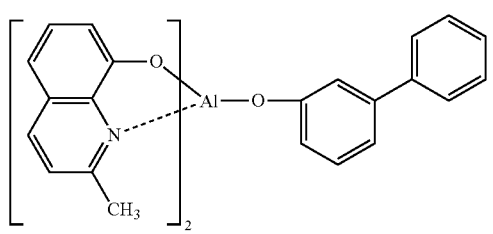
(A-7) 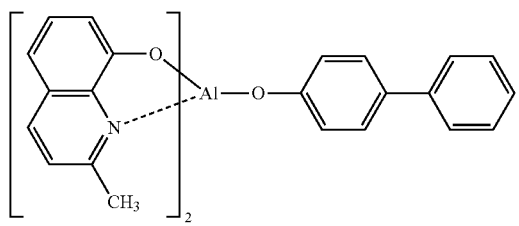
(A-8) 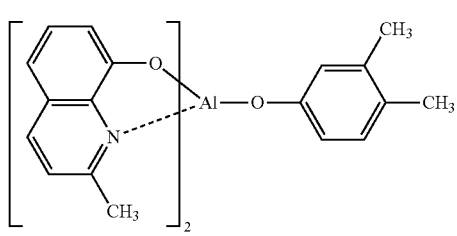
(A-9) 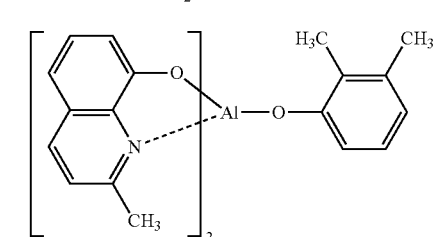
(A-10) 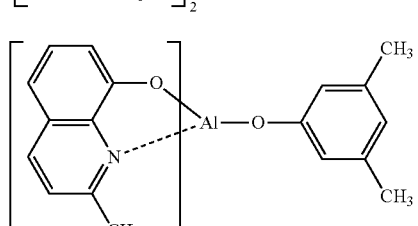
(A-11) 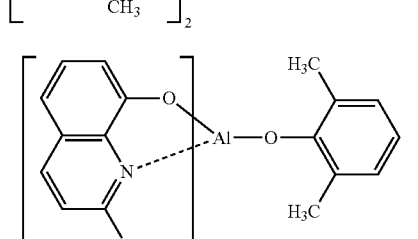
(A-12) 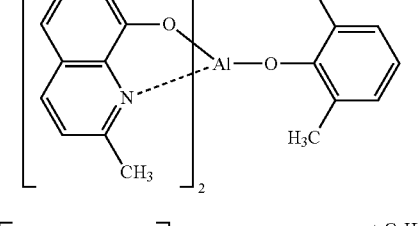
(A-13) 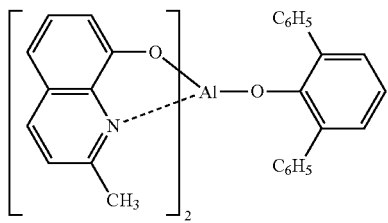
(A-14) 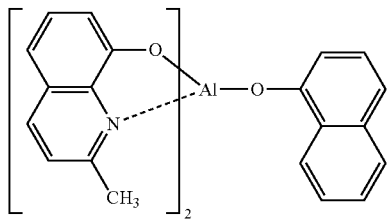
(A-15) 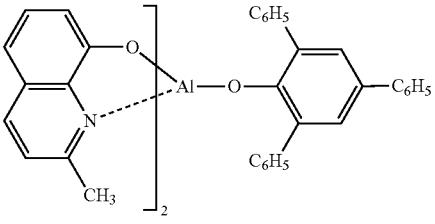
(A-16) 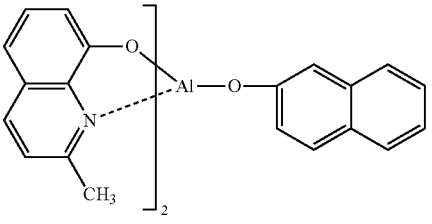
(A-17) 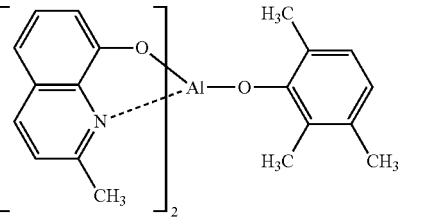
(A-18) 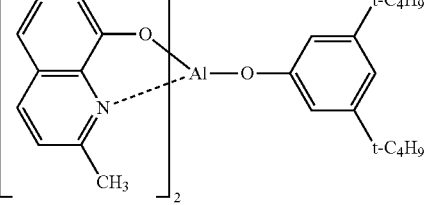

(A-19)
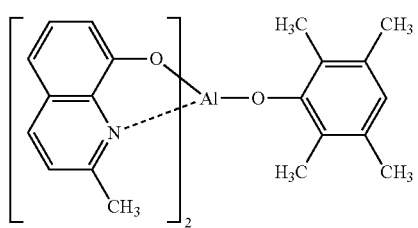
(A-20)
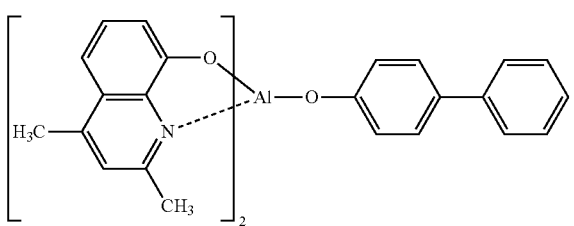
(A-21)
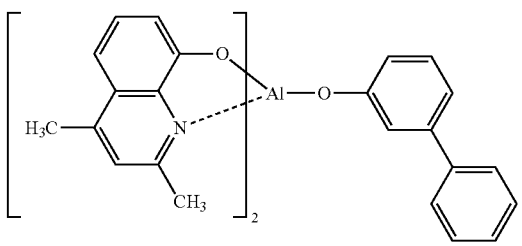
(A-22)
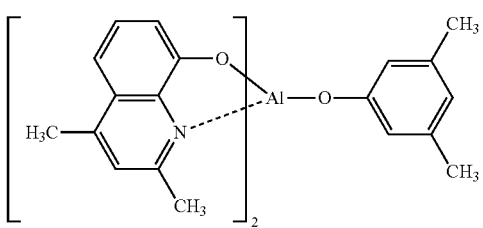
(A-23)
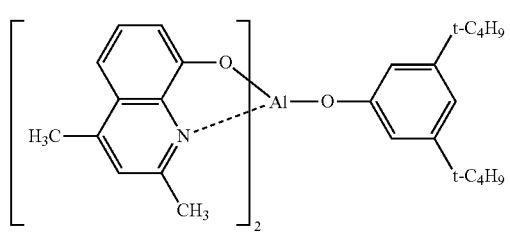
(A-24)
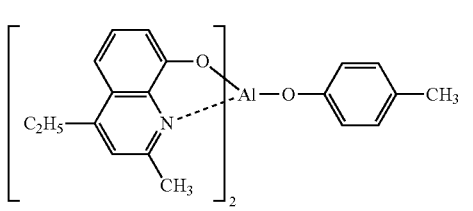
(A-25)
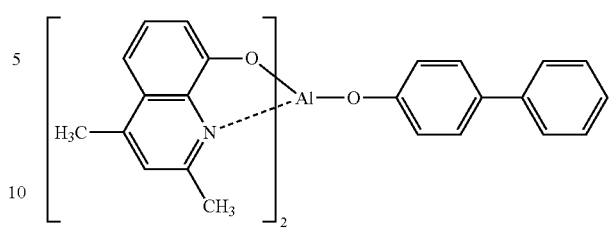
(A-26)
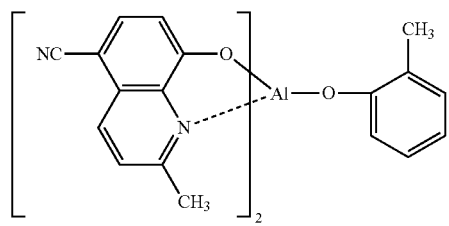
(A-27)
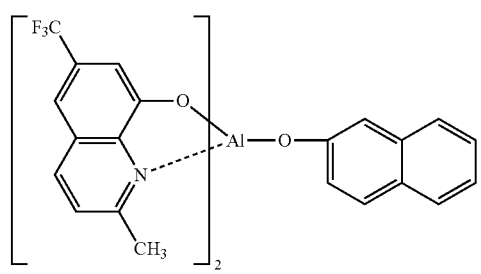
(A-28)
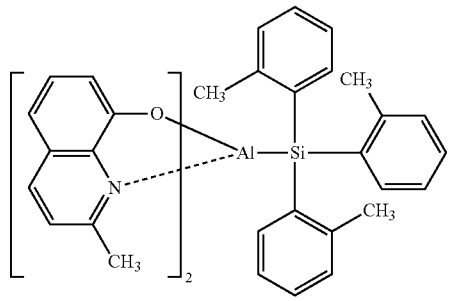
(A-29)
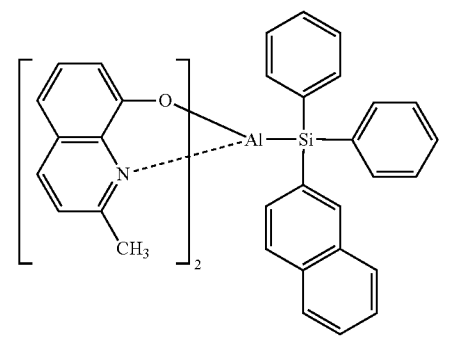

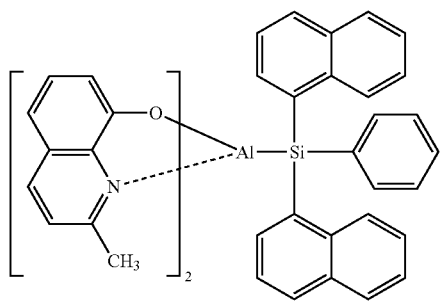

(A-30)

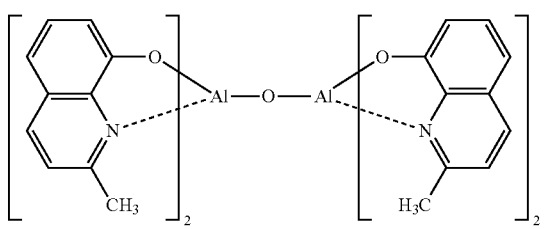

(A-31)

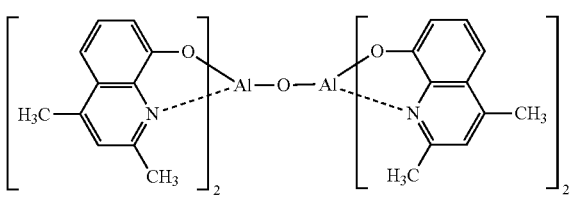

(A-32)

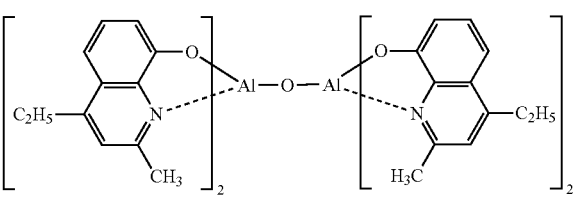

(A-33)

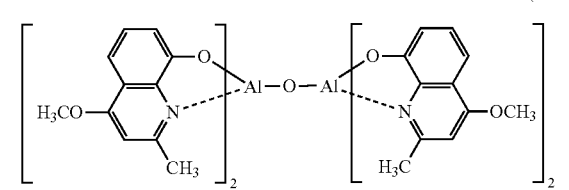

(A-34)

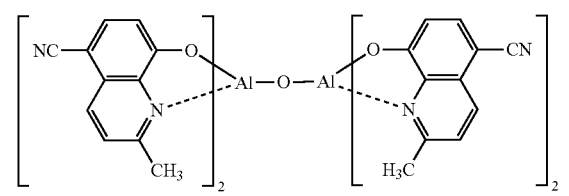

(A-35)

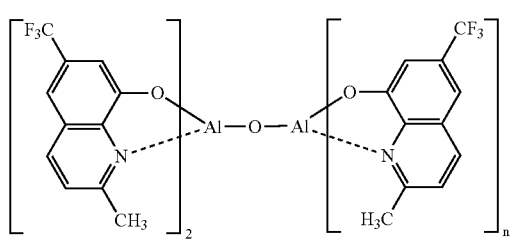

(A-36)

Another preferred example of the aromatic, nitrogen-containing cyclic compound includes a nitrogen-containing, five-membered cyclic compound. The nitrogen-containing, five-membered ring may include imidazole ring, triazole ring, tetrazole ring, oxadiazole ring, thiadiazole ring, oxatriazole ring, and thiatriazole ring. The nitrogen-containing, five-membered cyclic compound has a skeletal structure such as benzimidazole ring, benzotriazole ring, pyridinoimidazole ring, pyrimidinoimidazole ring, and pyridazinoimidazole ring, and is preferably represented by the following formula B:

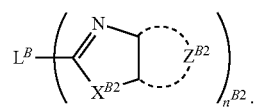

(B)

In the formula B, $L^B$ is a mono- to tetravalent bonding group such as carbon atom, silicon atom, nitrogen atom, boron atom, oxygen atom, sulfur atom, metal (barium, beryllium, etc.), aromatic hydrocarbon ring, and heteroaromatic ring, with carbon atom, nitrogen atom, silicon atom, boron atom, oxygen atom, sulfur atom, aryl group and heteroaromatic group being preferred, and carbon atom, silicon atom, aryl group and heteroaromatic group being more preferred.

The aryl group or heteroaromatic group for $L^B$ may be substituted. The substituent group is preferably alkyl group, alkenyl group, alkynyl group, aryl group, amino group, alkoxy group, aryloxy group, acyl group, alkoxycarbonyl group, aryloxycarbonyl group, acyloxy group, acylamino group, alkoxycarbonylamino group, aryloxycarbonylamino group, sulfonylamino group, sulfamoyl group, carbamoyl group, alkylthio group, arylthio group, sulfonyl group, halogen atom, cyano group, or heteroaromatic group; more preferably alkyl group, aryl group, alkoxy group, aryloxy group, halogen atom, cyano group, or heteroaromatic group; still more preferably alkyl group, aryl group, alkoxy group, aryloxy group, or heteroaromatic group; and particularly preferably alkyl group, aryl group, alkoxy group, or heteroaromatic group.

Preferred examples of $L^B$ are shown below.

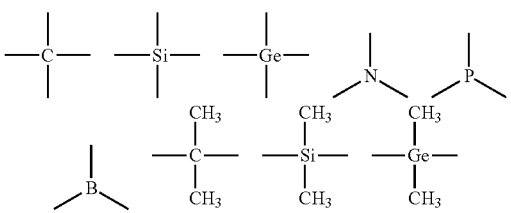

-continued

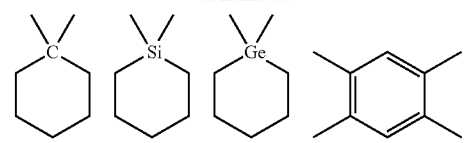
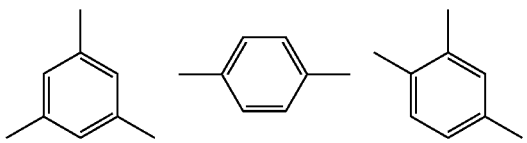
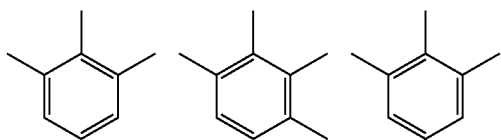
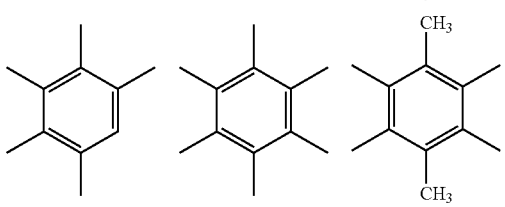
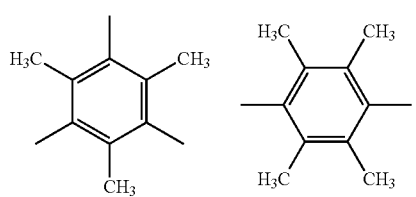
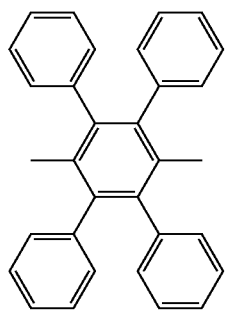
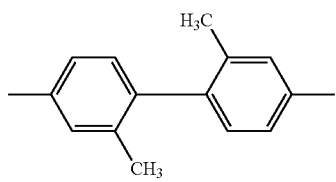
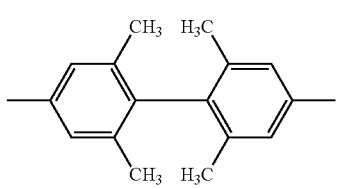

-continued

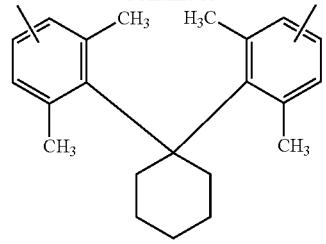

$X^{B2}$ in the formula B is —O—, —S— or =N—$R^{B2}$, preferably —O— or =N—$R^{B2}$, and more preferably =N—$R^{B2}$. $R^{B2}$ is hydrogen atom, aliphatic hydrocarbon group, aryl group or heterocyclic group.

The aliphatic hydrocarbon group for $R^{B2}$ may be linear, branched or cyclic and includes alkyl groups having preferably 1 to 20 carbon atoms, more preferably 1 to 12 carbon atoms and particularly preferably 1 to 8 carbon atoms such as methyl, ethyl, isopropyl, t-butyl, n-octyl, n-decyl, n-hexadecyl, cyclopropyl, cyclopentyl, and cyclohexyl; alkenyl groups having preferably 2 to 20 carbon atoms, more preferably 2 to 12 carbon atoms and particularly preferably 2 to 8 carbon atoms such as vinyl, allyl, 2-butenyl, and 3-pentenyl; and alkynyl groups having preferably 2 to 20 carbon atoms, more preferably 2 to 12 carbon atoms and particularly preferably 2 to 8 carbon atoms such as propargyl and 3-pentynyl, with alkyl groups being preferred.

The aryl group for $R^{B2}$ is a non-condensed or condensed aryl group and has preferably 6 to 30 carbon atoms, more preferably 6 to 20 carbon atoms and still more preferably 6 to 12 carbon atoms. Examples thereof include phenyl, 2-methylphenyl, 3-methylphenyl, 4-methylphenyl, 2-methoxyphenyl, 3-trifluoromethylphenyl, pentafluorophenyl, 1-naphthyl, and 2-naphthyl.

The heterocyclic group for $R^{B2}$ is a non-condensed or condensed heterocyclic group, preferably a heteroaromatic group having at least one atom selected from nitrogen atom, oxygen atom, sulfur atom and selenium atom, and has preferably 1 to 20 carbon atoms, more preferably 1 to 12 carbon atoms and still more preferably 2 to 10 carbon atoms. Examples of the basic structure of the heterocyclic group include pyrrolidine, piperidine, piperazine, morpholine, thiophene, selenophene, furan, pyrrole, imidazole, pyrazole, pyridine, pyrazine, pyridazine, pyrimidine, triazole, triazine, indole, indazole, purine, thiazoline, thiazole, thiadiazole, oxazoline, oxazole, oxadiazole, quinoline, isoquinoline, phthalazine, naphthyridine, quinoxaline, quinazoline, cinnoline, pteridine, acridine, phenanthroline, phenazine, tetrazole, benzimidazole, benzoxazole, benzothiazole, benzotriazole, tetraazaindene, carbazole, and azepine, with furan, thiophene, pyridine, pyrazine, pyrimidine, pyridazine, triazine, quinoline, phthalazine, naphthyridine, quinoxaline, and quinazoline being preferred, furan, thiophene, pyridine, and quinoline being more preferred, and quinoline being still more preferred.

The aliphatic hydrocarbon group, aryl group and heterocyclic group for $R^{B2}$ may be substituted. The substituent groups and preferred substituent groups are the same as the substituent groups for $L^B$ mentioned above.

$R^{B2}$ is preferably aliphatic hydrocarbon group, aryl group or heterocyclic group, more preferably aliphatic hydrocarbon group or aryl group (having preferably 6 to 30 carbon atoms, more preferably 6 to 20 carbon atoms, and still more preferably 6 to 12 carbon atoms), and still more preferably aliphatic hydrocarbon group (having preferably 1 to 20 carbon atoms, more preferably 1 to 12 carbon atoms, and still more preferably 2 to 10 carbon atoms).

$Z^{B2}$ is a group of atoms to form an aromatic ring. The aromatic ring formed by $Z^{B2}$ is either of an aromatic hydrocarbon ring or a heteroaromatic ring. Examples there of include benzene ring, pyridine ring, pyrazine ring, pyrimidine ring, pyridazine ring, triazine ring, pyrrole ring, furan ring, thiophene ring, selenophene ring, tellurophene ring, imidazole ring, thiazole ring, selenazole ring, tellurazole ring, thiadiazole ring, oxadiazole ring, and pyrazole ring, with benzene ring, pyridine ring, pyrazine ring, pyrimidine ring, and pyridazine ring being preferred, benzene ring, pyridine ring, and pyrazine ring being more preferred, benzene ring and pyridine ring being still more preferred, and pyridine ring being particularly preferred.

The aromatic ring formed by $Z^{B2}$ may be fused with another ring to form a condensed ring and may be substituted. Examples of the substituent group are the same as the substituent groups for $L^B$ and preferably alkyl group, alkenyl group, alkynyl group, aryl group, amino group, alkoxy group, aryloxy group, acyl group, alkoxycarbonyl group, aryloxycarbonyl group, acyloxy group, acylamino group, alkoxycarbonylamino group, aryloxycarbonylamino group, sulfonylamino group, sulfamoyl group, carbamoyl group, alkylthio group, arylthio group, sulfonyl group, halogen atom, cyano group, and heterocyclic group; more preferably alkyl group, aryl group, alkoxy group, aryloxy group, halogen atom, cyano group, and heterocyclic group; still more preferably alkyl group, aryl group, alkoxy group, aryloxy group, and heteroaromatic group; and particularly preferably alkyl group, aryl group, alkoxy group, and heteroaromatic group.

$n^{B2}$ is an integer of 1 to 6, preferably an integer of 1 to 4, and still more preferably 2 or 3.

The nitrogen-containing five-membered cyclic compound of the formula B is preferably represented by the following formula B':

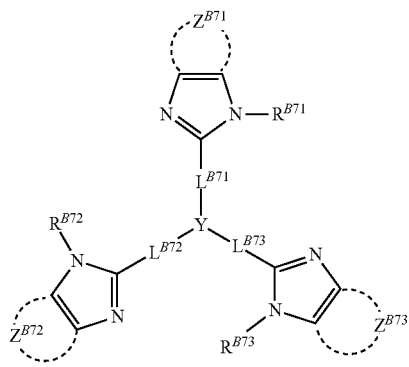

(B')

In the formula B', $R^{B71}$, $R^{B72}$, $R^{B73}$ and their preferred examples are each independently the same as defined in $R^{B2}$ of the formula B.

$Z^{B71}$, $Z^{B72}$, $Z^{B73}$ and their preferred examples are each independently the same as defined in $Z^{B2}$ of the formula B.

$L^{B71}$, $L^{B72}$ and $L^{B73}$ are each independently single bond or bivalent group as defined in $L^B$ of the formula B, preferably single bond, bivalent aromatic hydrocarbon group, bivalent heteroaromatic group or bivalent bonding group composed of a combination thereof, with single bond being preferred.

$L^{B71}$, $L^{B72}$ and $L^{B73}$ may be substituted. The substituent groups and preferred substituent groups are the same as the substituent groups for $L^B$ of the formula B.

Y is nitrogen atom, 1,3,5-benzenetriyl group or 2,4,6-triazinetriyl group. The 1,3,5-benzenetriyl group may be substituted at 2,4,6-position, for example, by alkyl group, aromatic hydrocarbon group or halogen atom.

Specific examples of the nitrogen-containing five-membered cyclic compound of the formula B or B' are shown below, although not limited thereto.

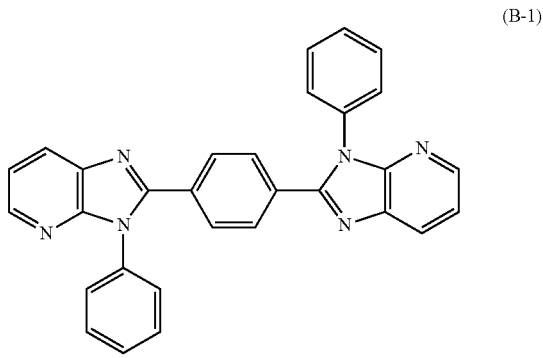

(B-1)

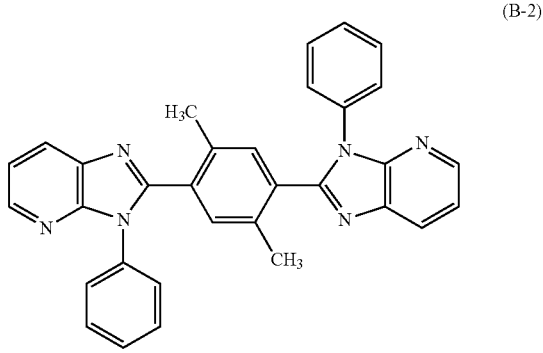

(B-2)

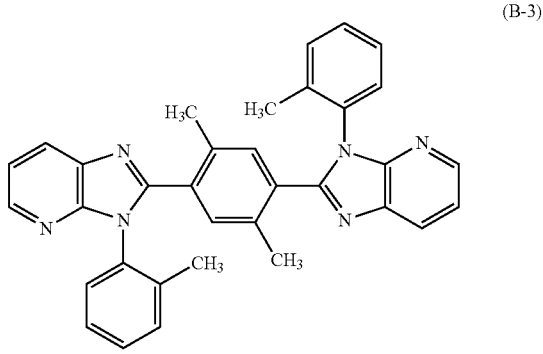

(B-3)

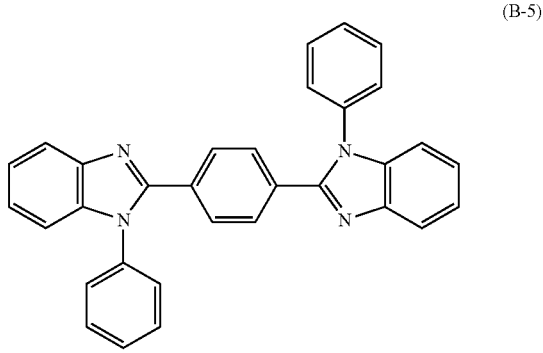

(B-5)

(B-6)
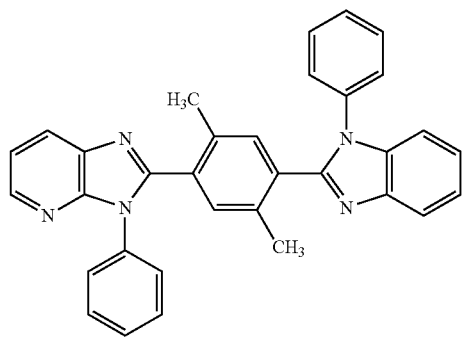
(B-10)
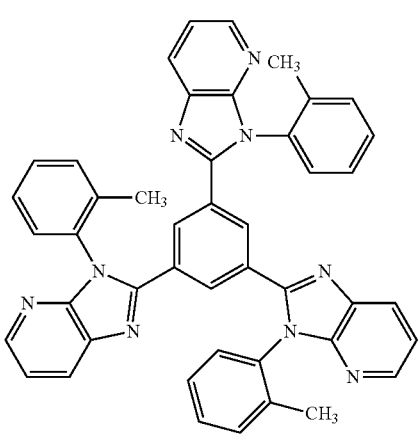
(B-7)
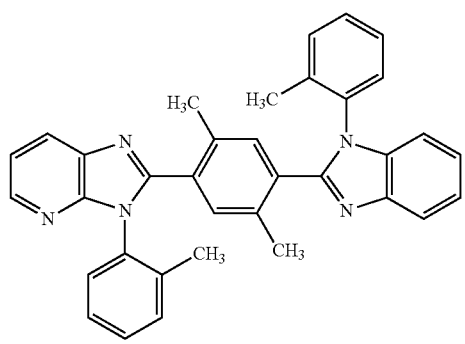
(B-4)
(B-11)
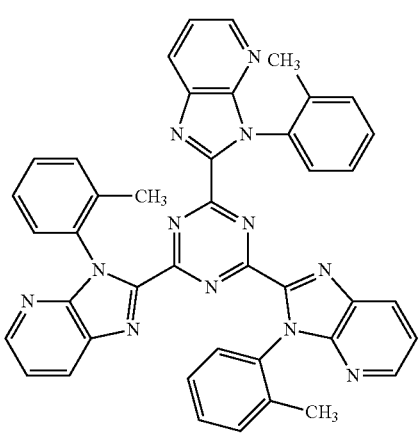
(B-9)
(B-8)
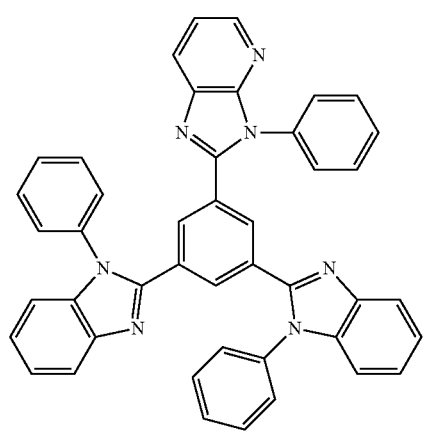

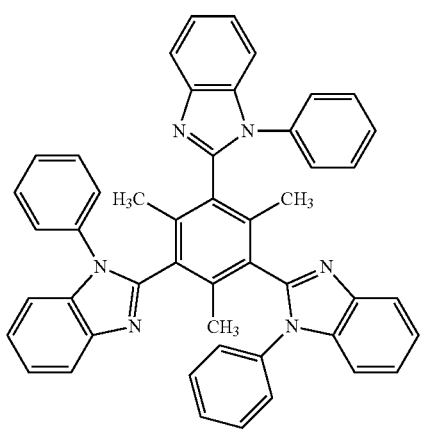
(B-13)

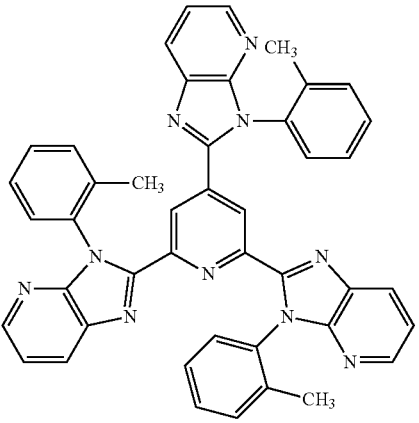
(B-12)

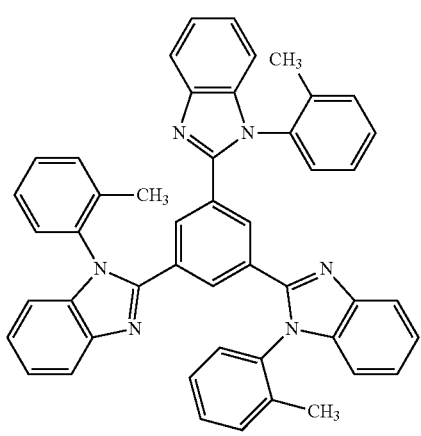
(B-14)

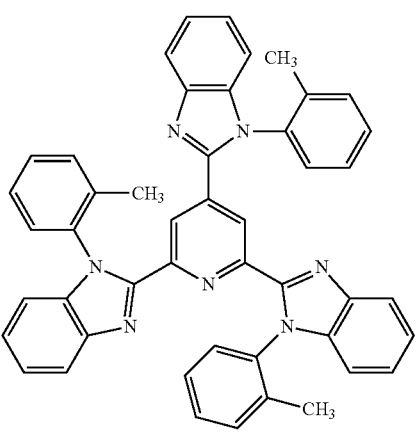
(B-13)

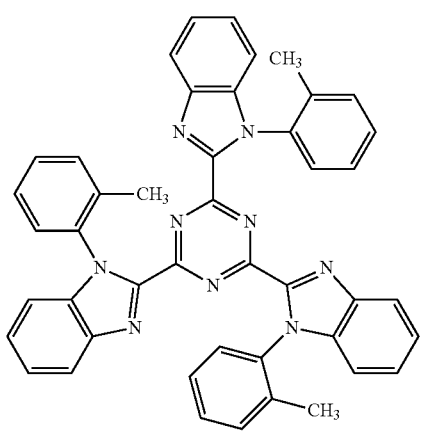
(B-15)

In addition to the material for organic EL devices of the invention and the aromatic, nitrogen-containing cyclic compound mentioned above, the compounds for forming the electron injection layer and electron transport layer may further include an electron-deficient, nitrogen-containing cyclic compound which has a structure combining an electron-deficient, nitrogen-containing 5- or 6-membered cyclic skeleton with a substituted or non-substituted indole skeleton, substituted or non-substituted carbazole skeleton, or substituted or non-substituted azacarbazole skeleton. Preferred electron-deficient, nitrogen-containing 5- or 6-membered cyclic skeleton includes each skeleton of pyridine, pyrimidine, pyrazine, triazine, triazole, oxadiazole, pyrazole, imidazole, quinoxaline, pyrrole, and a condensed skeleton thereof such as benzimidazole and imidazopyridine. The combination between the pyridine, pyrimidine, pyrazine or triazine skeleton with the carbazole, indole, azacarbazole or quinoxaline skeleton is preferred. Each skeleton may be either substituted or not substituted.

Examples of the electron-deficient, nitrogen-containing cyclic compound are shown below.
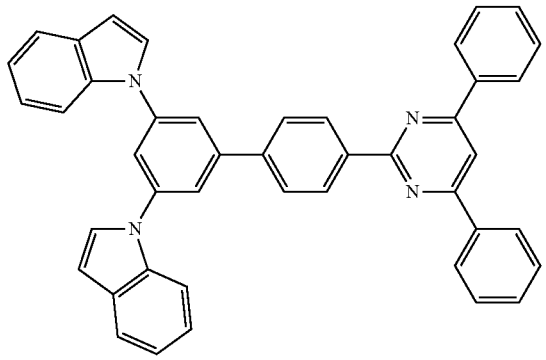
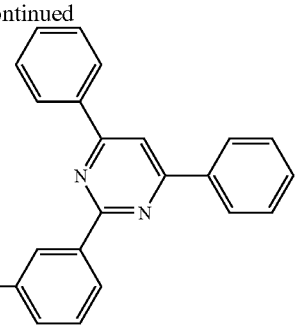
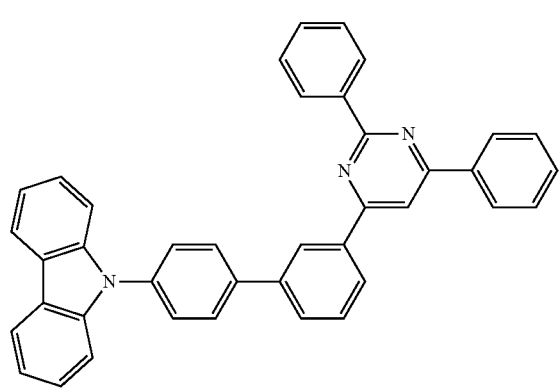
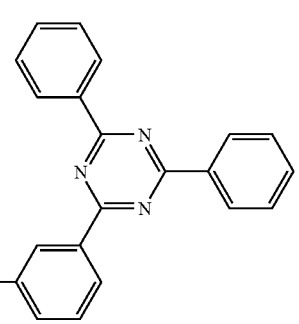
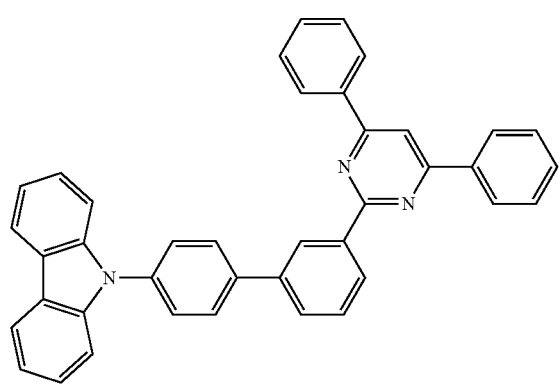
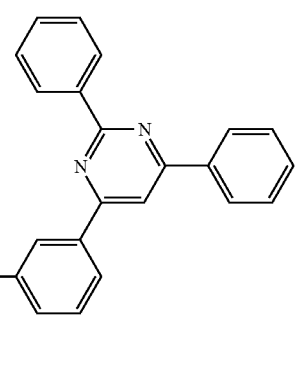
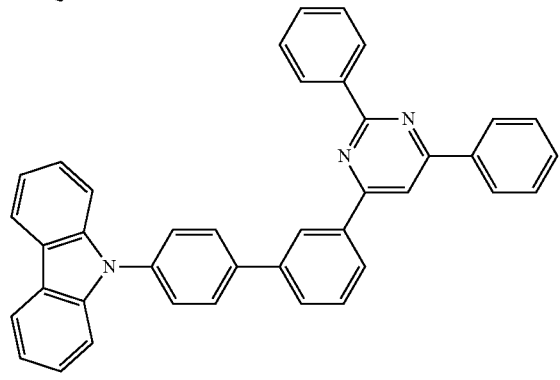
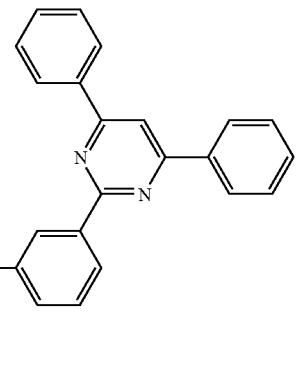

69
-continued
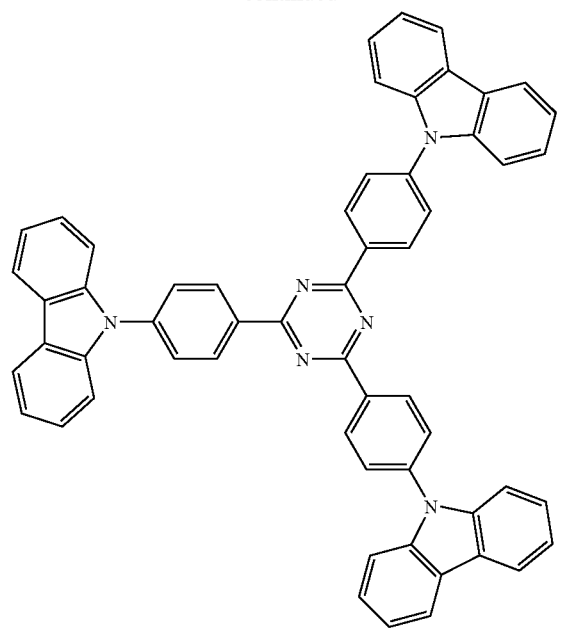
70
-continued
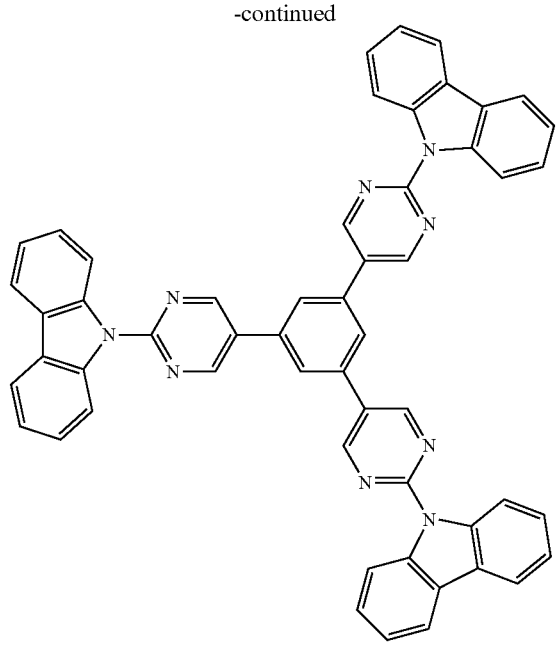
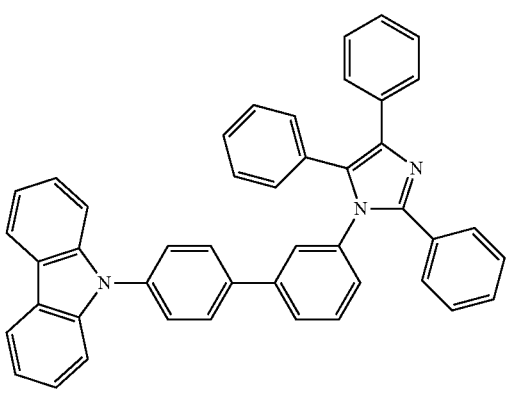
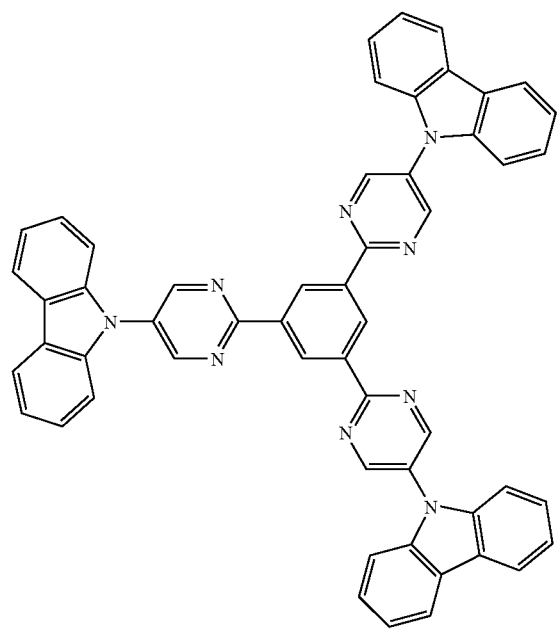
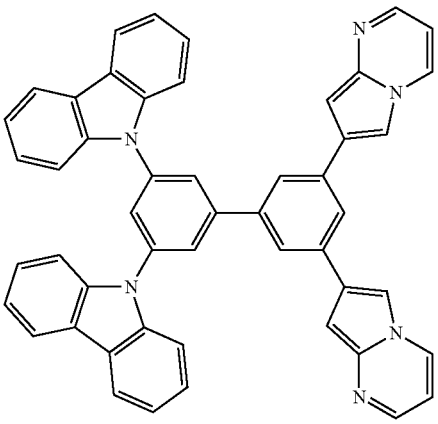

-continued

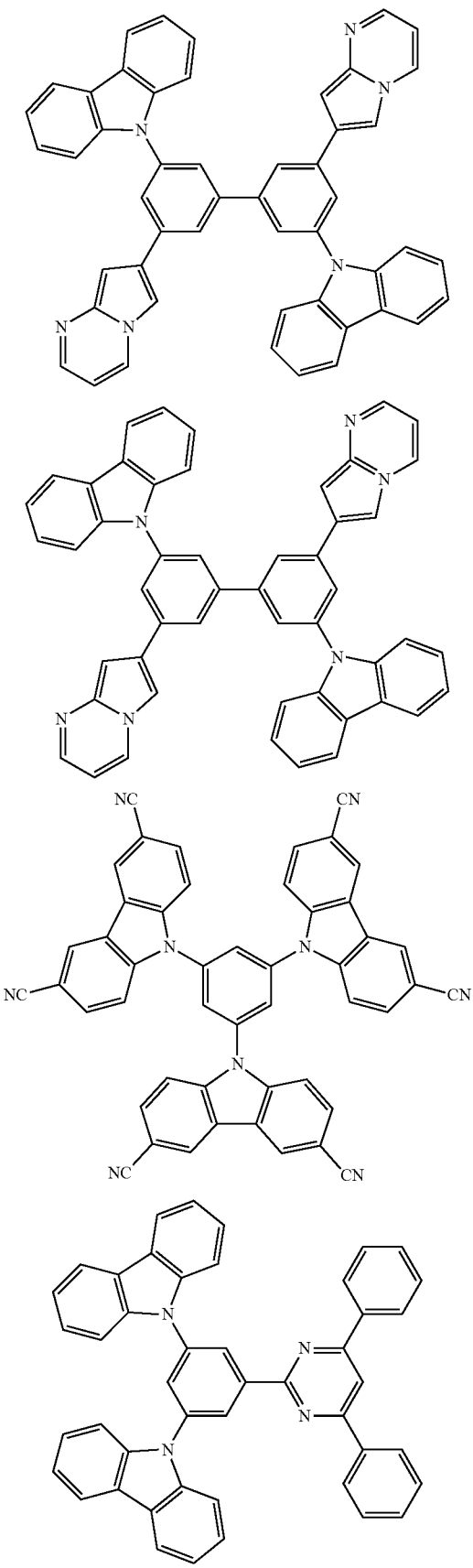

-continued

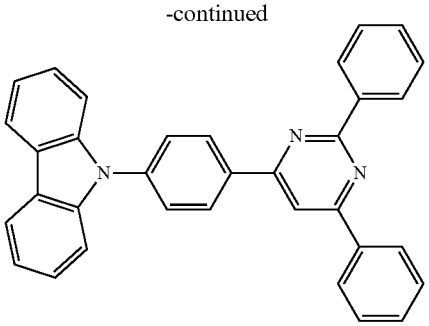

The electron injection layer and electron transport layer may be a single-layered structure or multi-layered structure of layers having the same composition or different compositions, each layer being made of one or more kinds of the materials mentioned above, preferably a compound having a nitrogen-containing heterocyclic group with a low π-electron density.

In addition to the material for organic EL devices of the invention, the nitrogen-containing cyclic compound and the electron-deficient, nitrogen-containing cyclic compound, the electron injection layer is preferably incorporated with an inorganic compound such as insulating material and semiconductor. The insulating material or semiconductor incorporated into the electron injection layer effectively prevents the leak of electric current to enhance the electron injection properties.

The insulating material is preferably at least one metal compound selected from the group consisting of alkali metal chalcogenides, alkaline earth metal chalcogenides, alkali metal halides and alkaline earth metal halides. The metal compound incorporated into the electron injection layer further enhances the electron injection properties. Preferred examples of the alkali metal chalcogenides include $Li_2O$, $K_2O$, $Na_2S$, $Na_2Se$ and $Na_2O$, and preferred examples of the alkaline earth metal chalcogenides include CaO, BaO, SrO, BeO, BaS and CaSe. Preferred examples of the alkali metal halides include LiF, NaF, KF, LiCl, KCl and NaCl. Examples of the alkaline earth metal halides include fluorides such as $CaF_2$, $BaF_2$, $SrF_2$, $MgF_2$ and $BeF_2$ and halides other than fluorides.

Examples of the semiconductor may include oxide, nitride or oxynitride each containing at least one element selected from the group consisting of Ba, Ca, Sr, Yb, Al, Ga, In, Li, Na, Cd, Mg, Si, Ta, Sb and Zn. The semiconductor may be used singly or in combination of two or more. The inorganic compound included in the electron injection layer preferably forms a microcrystalline or amorphous insulating thin film. When the electron injection layer is formed from such an insulating thin film, the thin film is made more uniform to decrease the pixel defects such as dark spots. Examples of such inorganic compound include alkali metal chalcogenides, alkaline earth metal chalcogenides, alkali metalhalides and alkaline earth metalhalide, each being described above.

The electron injection layer may be included with the reducing dopant described above.

Since the anode of the organic EL devices has a function of injecting holes into the hole transport layer or light emitting layer, the anode preferably has a work function of 4.5 eV or more. Examples of the material for the anode include indium tin oxide (ITO), tin oxide (NESA), gold, silver, platinum and copper. Since the cathode has a function of injecting electrons into the electron injection layer or light emitting layer, the material for the cathode preferably has a small work function.

Examples of the material for the cathode include, but not limited to, indium, aluminum, magnesium, magnesium-indium alloy, magnesium-aluminum alloy, aluminum-lithium alloy, aluminum-scandium-lithium alloy, and magnesium-silver alloy.

The method of forming each layer of the organic EL devices is not critical, and a known method such as a vacuum vapor deposition method and a spin coating method may be employed. The organic thin film layer containing the material for organic EL devices of the invention can be formed by a known method such as a vacuum vapor deposition method, molecular beam epitaxy method (MBE method) and a solution coating method, for example, a dipping method, spin coating method, a casting method, a bar coating method and a roll coating method.

The thickness of each organic layer of the organic EL devices is not particularly limited. Generally, an excessively thin layer likely causes defects such as pin holes, and an excessively thick layer requires a high applied voltage to decrease the efficiency. The thickness is preferably from several nanometers to 1 μm.

The hole injection/transport layer is formed from an aromatic amine compound, preferably the aromatic amine derivative represented by the following formula I:

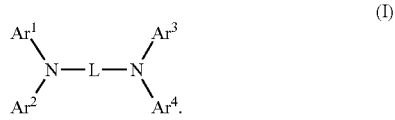

In the formula I, $Ar^1$ to $Ar^4$ are each independently aryl group (inclusive of heteroaryl group) having 5 to 50 ring atoms.

Examples of the aryl group having 5 to 50 ring atoms include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group, 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline 8-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group, with phenyl group, naphthyl group, biphenyl group, anthranyl group, phenanthryl group, pyrenyl group, chrysenyl group, fluoranthenyl group, and fluorenyl group being preferred.

L is a bonding group such as arylene group (inclusive of heteroarylene group) having 5 to 50 ring atoms which is optionally substituted or a bivalent group composed of two or more arylene groups which are bonded to each other via a single bond, ether linkage, thioether linkage, alkylene group having 1 to 20 carbon atoms, alkenylene group having 2 to 20 carbon atoms or amino linkage. Examples of the arylene group having 5 to 50 ring atoms include 1,4-phenylene group, 1,2-phenylene group, 1,3-phenylene group, 1,4-naphthylene group, 2,6-naphthylene group, 1,5-naphthylene group, 9,10-anthranylene group, 9,10-phenanthrenylene group, 3,6-phenanthrenylene group, 1,6-pyrenylene group, 2,7-pyrenylene group, 6,12-chrysenylene group, 4,4'-biphenylene group, 3,3'-biphenylene group, 2,2'-biphenylene group, 2,7-fluorenylene group, 2,5-thiophenylene group, 2,5-silolylene group, and 2,5-oxadiazolylene group, with 1,4-phenylene group, 1,2-phenylene group, 1,3-phenylene group, 1,4-naphthylene group, 9,10-anthranylene group, 6,12-chrysenylene group, 4,4'-biphenylene group, 3,3'-biphenylene group, 2,2'-biphenylene group, and 2,7-fluorenylene group being preferred.

When L is a bonding group composed of two or more arylene groups, the adjacent couple of arylene groups may be bonded via a bivalent group to form a new ring. The bivalent group for forming such ring may include tetramethylene group, pentamethylene group, hexamethylene group, diphenylmethane-2,2'-diyl group, diphenylethane 3,3'-diyl group, and diphenylpropane-4,4'-diyl group.

Examples of the substituent group for $Ar^1$ to $Ar^4$ and L include aryl group (inclusive of heteroaryl group) having 5 to 50 ring atoms which is optionally substituted, alkyl group having 1 to 50 carbon atoms which is optionally substituted, alkoxy group having 1 to 50 carbon atoms which is optionally substituted, aralkyl group having 7 to 50 carbon atoms which is optionally substituted, aryloxy group (inclusive of heteroaryloxy group) having 5 to 50 ring atoms which is optionally substituted, arylthio group (inclusive of heteroarylthio group) having 5 to 50 ring atoms which is optionally substituted, alkoxycarbonyl group having 2 to 50 carbon atoms which is optionally substituted, amino group substituted with aryl group inclusive of heteroaryl group) having 5 to 50 ring atoms which is optionally substituted, halogen group, cyano group, nitro group, and hydroxyl group.

Examples of the aryl group having 5 to 50 ring atoms which is optionally substituted include phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, fluoranthenyl group, fluorenyl group, 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Examples of the alkyl group having 1 to 50 carbon atoms which is optionally substituted include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-c-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, 1,2,3-trinitropropyl group, cyclopropyl group, cyclobutyl group, cyclopentyl group, cyclohexyl group, 4-methylcyclohexyl group, 1-adamantyl group, 2-adamantyl group, 1-norbornyl group, and 2-norbornyl group.

The alkoxy group having 1 to 50 carbon atoms which is optionally substituted is represented by —OY, wherein Y is methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, or 1,2,3-trinitropropyl group.

Examples of the aralkyl group having 7 to 50 carbon atoms which is optionally substituted include benzyl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, 2-β-naphthylisopropyl group, 1-pyrrolylmethyl group, 2-(1-pyrrolyl)ethyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group.

The aryloxy group having 5 to 50 ring atoms which is optionally substituted is represented by —OY', wherein Y' is phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline 1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 6-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, or 4-t-butyl-3-indolyl group.

The arylthio group having 5 to 50 ring atoms which is optionally substituted is represented by —SY'', wherein Y'' is phenyl group, 1-naphthyl group, 2-naphthyl group, 1-anthryl group, 2-anthryl group, 9-anthryl group, 1-phenanthryl group, 2-phenanthryl group, 8-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p'-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4''-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, or 4-t-butyl-3-indolyl group.

The alkoxycarbonyl group having 2 to 50 carbon atoms which is optionally substituted is represented by —COOZ, wherein Z is methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-trihydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromoisopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triaminopropyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group, or 1,2,3-trinitropropyl group.

The amino group substituted with aryl group having 5 to 50 ring atoms which is optionally substituted is represented by —NPQ, wherein P and Q are each phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl-4-yl group, 2-pyrrolyl group, 3-pyrrolyl group, pyrazinyl group, 2-pyridinyl group, 3-pyridinyl group, 4-pyridinyl group, 2-indolyl group, 3-indolyl group, 4-indolyl group, 5-indolyl group, 6-indolyl group, 7-indolyl group, 1-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3-yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 1-phenoxazinyl group, 2-phenoxazinyl group, 3-phenoxazinyl group, 4-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, or 4-t-butyl-3-indolyl group.

Examples of the compound of the formula I are shown below, although not limited thereto.

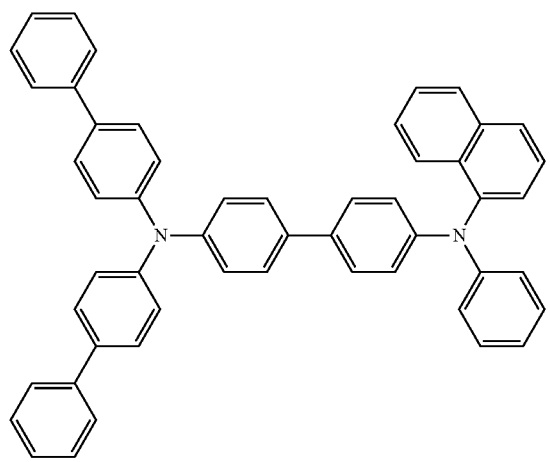

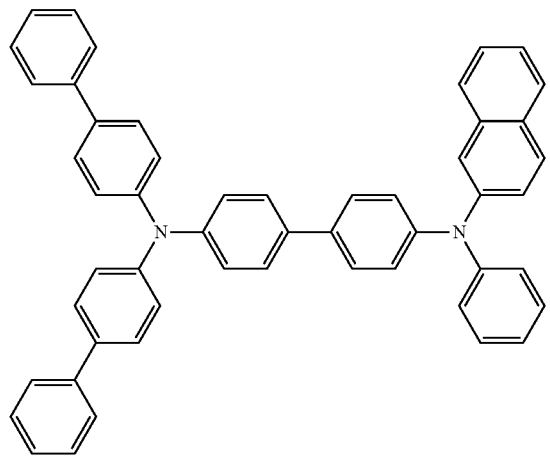

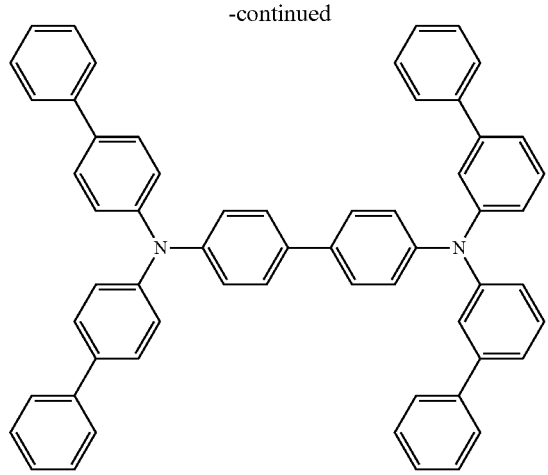
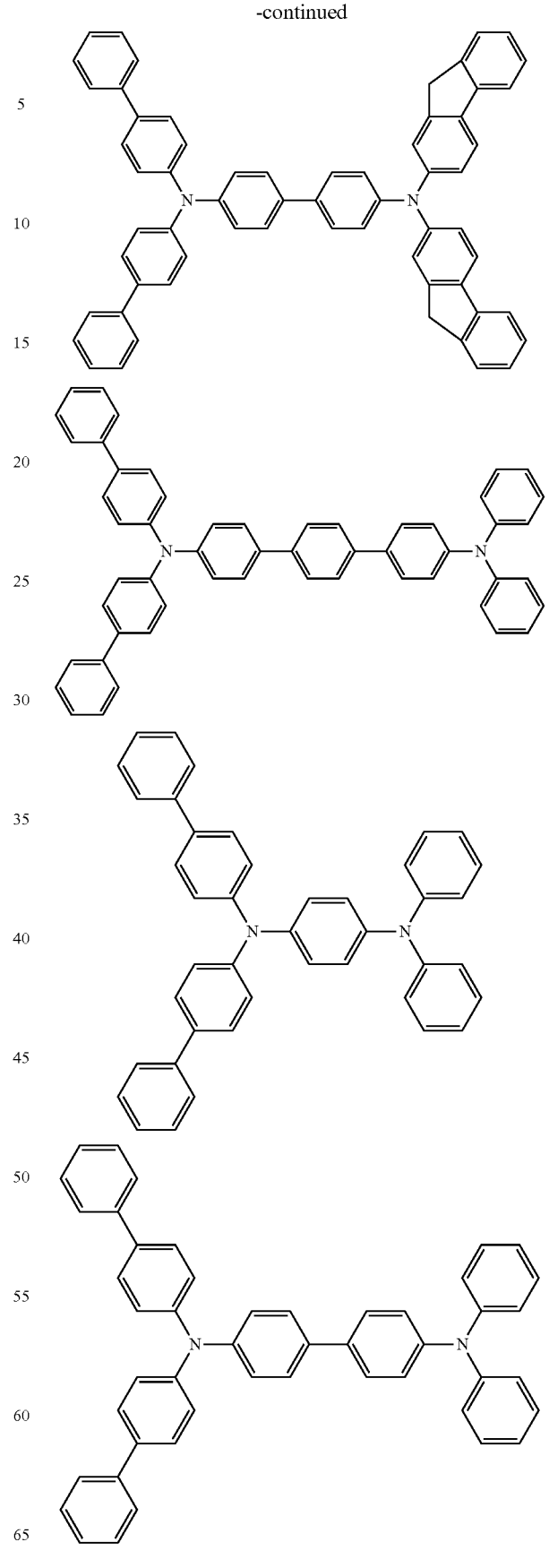

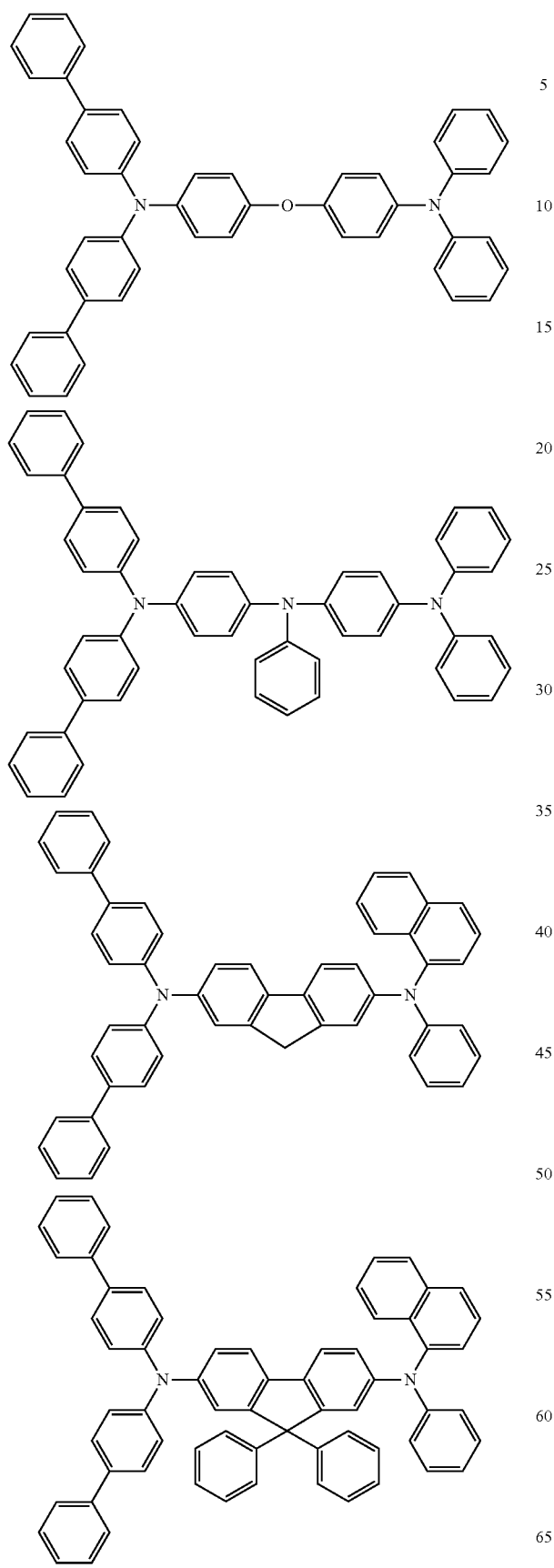
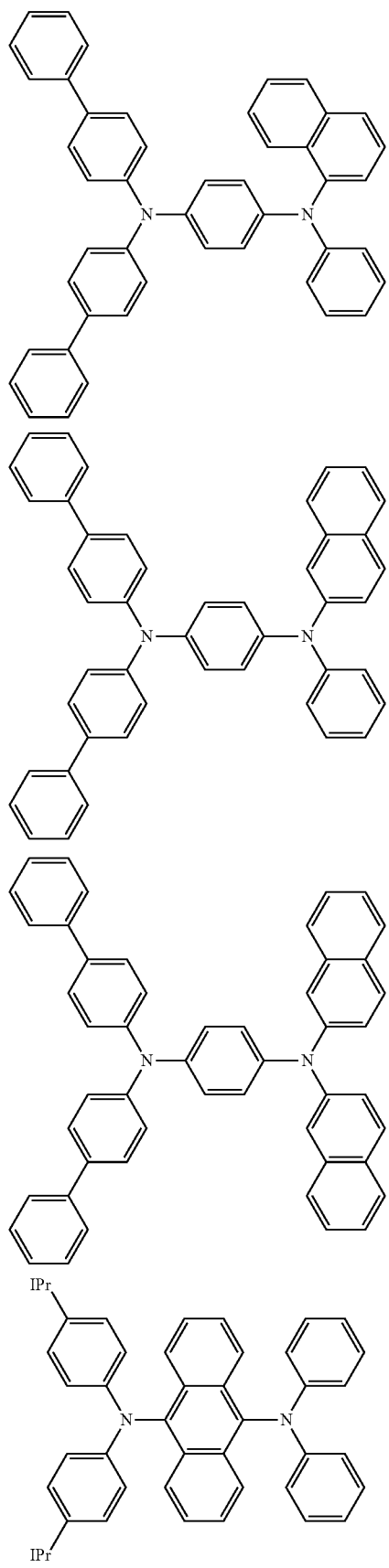

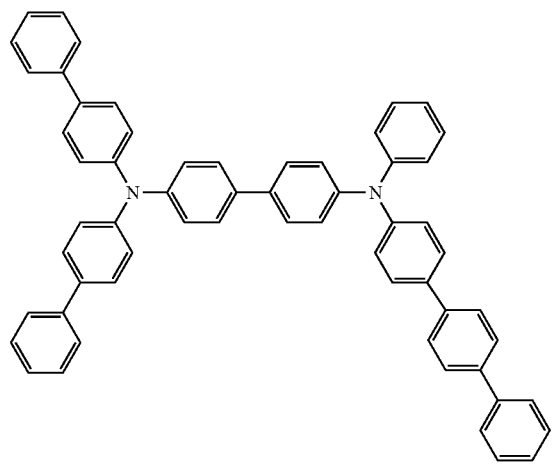
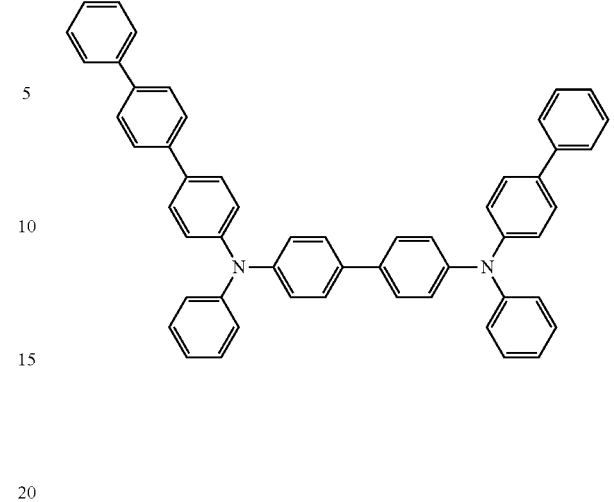
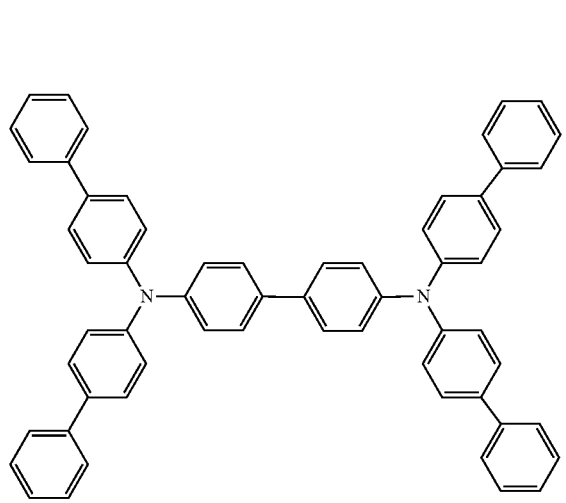
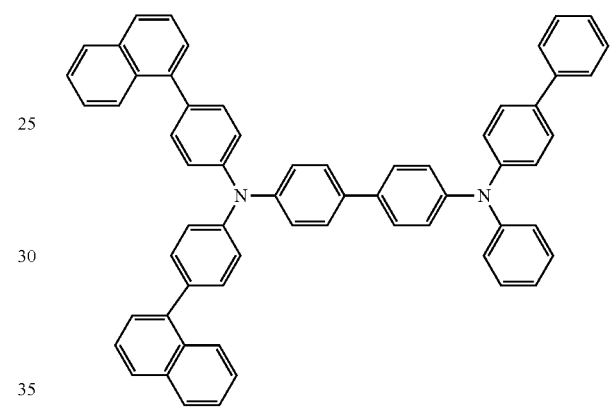
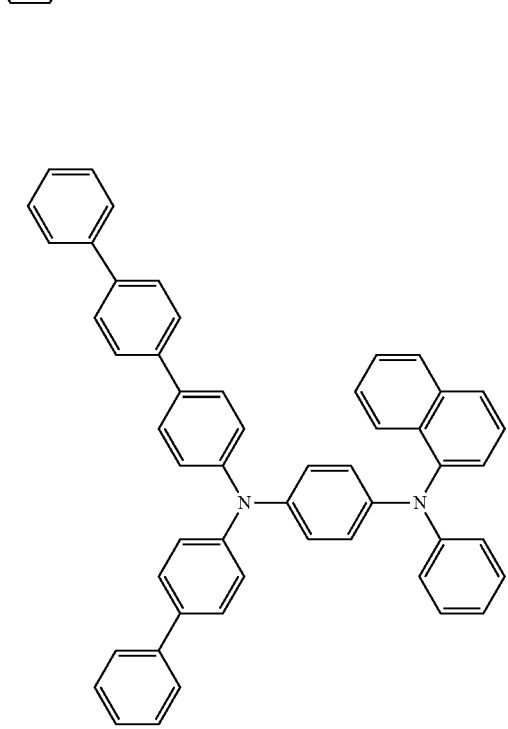
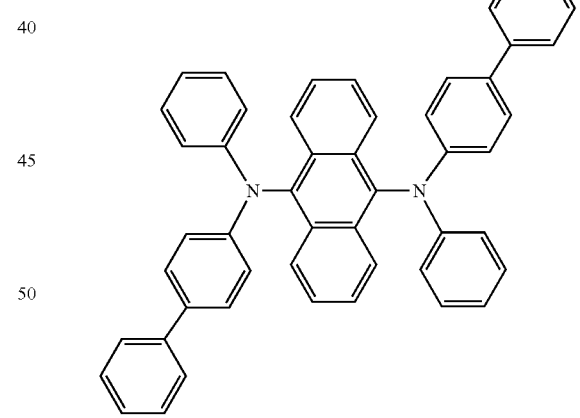
In addition, the aromatic amine of the following formula II is suitable as the material for the hole injection/transport layer.
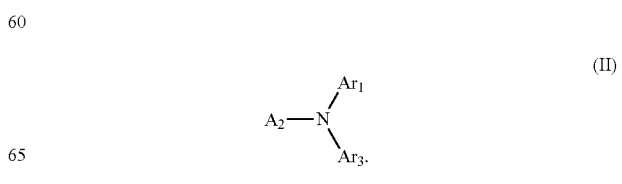

In the formula II, the definition of each of $Ar_1$ to $Ar_3$ is the same as those of the $Ar^1$ to $Ar^4$ in the formula I. Examples of the compound of the formula II are shown below, although not limited thereto.
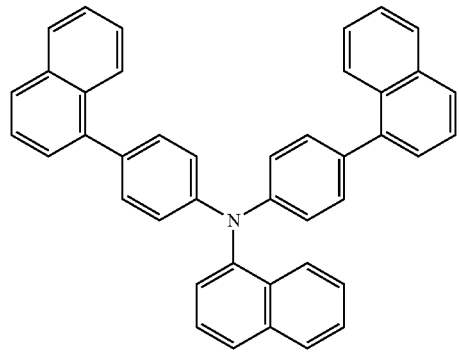
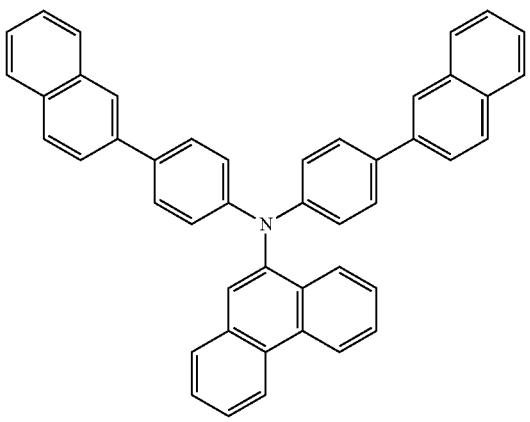
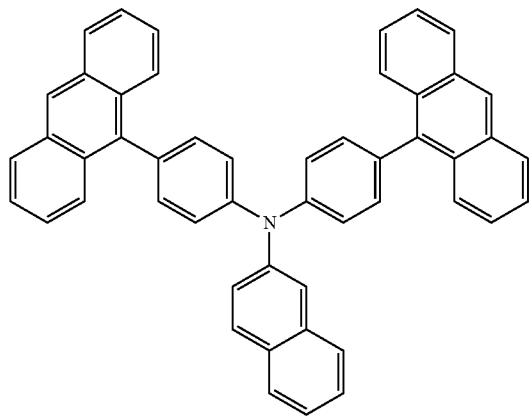
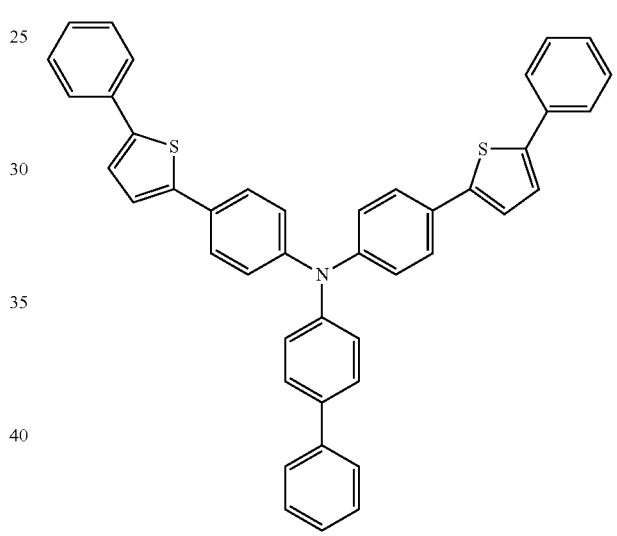
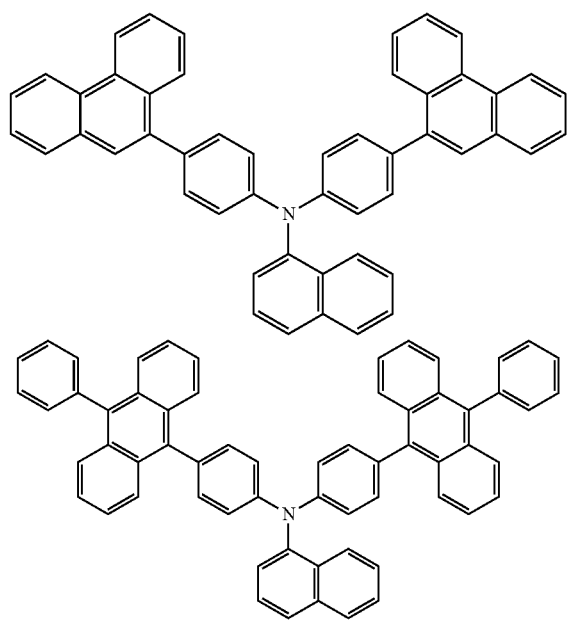
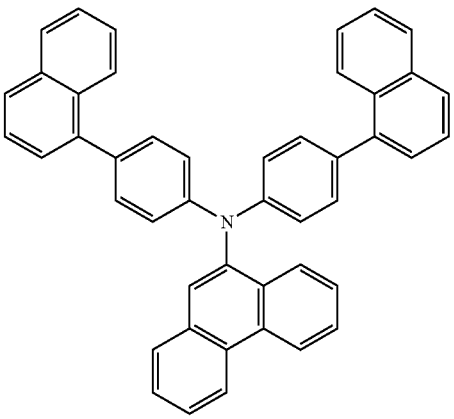

91
-continued
92
-continued
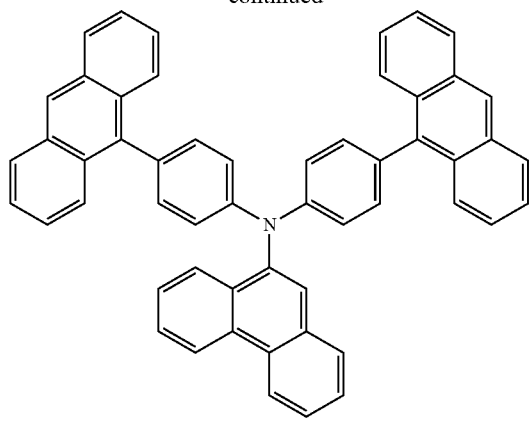
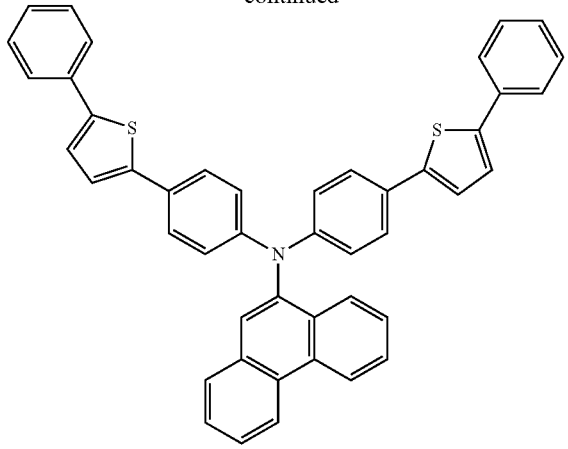
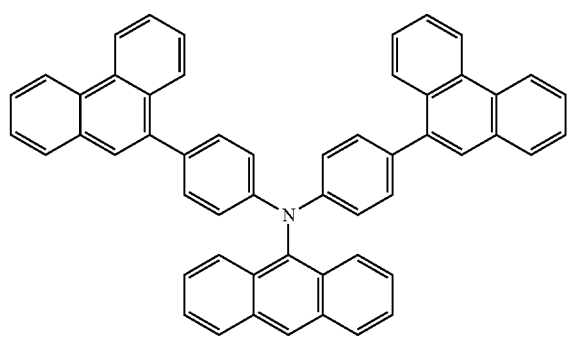
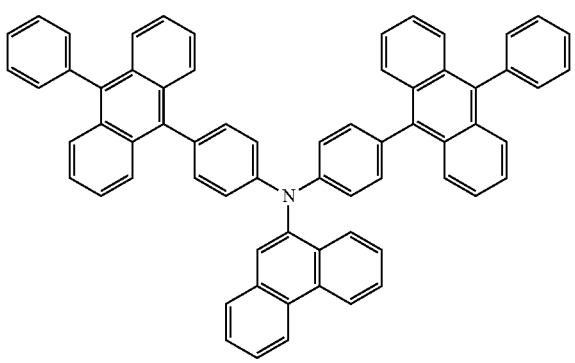
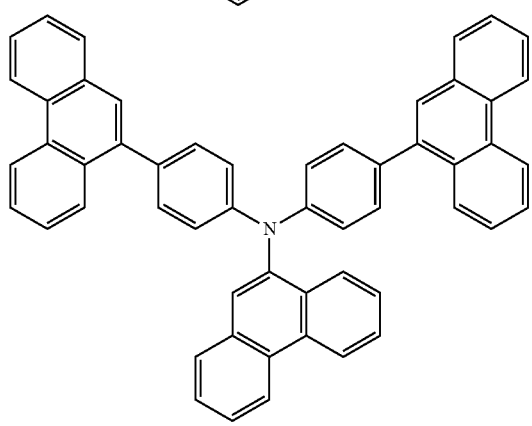
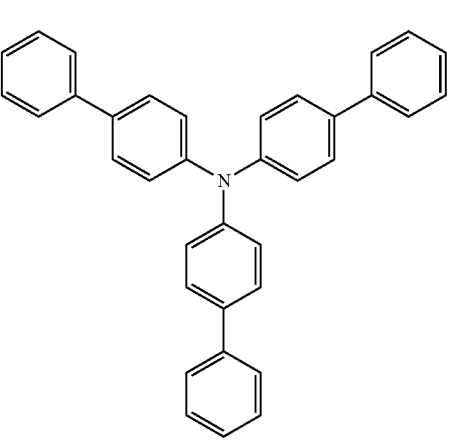

Synthesis Example 1

Synthesis of Compound No. 6

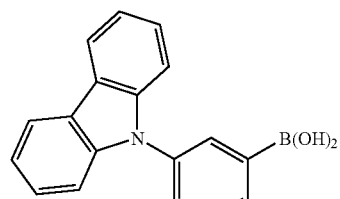

1

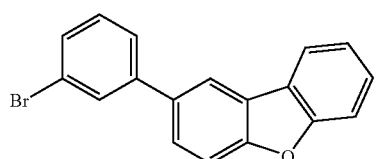 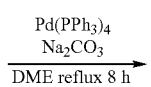 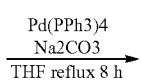

2

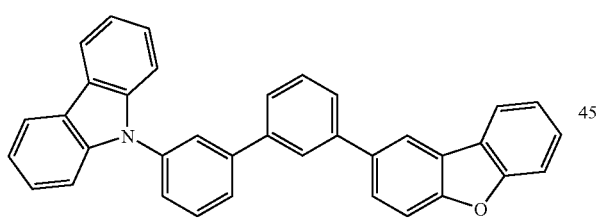

No. 6

A three-necked flask was charged with 3.4 g (1.2 eq., 12 mmol) of compound 1, 3.2 g (1 eq., 10 mmol) of compound 2, 10 ml of 2M $Na_2CO_3$ aqueos solution (20 mmol), 50 ml of DME, and 0.58 g of 5 mol % $Pd[PPh_3]_4$ (0.5 mmol). The contents were refluxed for 8 hrs in an argon atmosphere.

After the reaction, the reaction product mixture was cooled to room temperature and poured into a separatory funnel. After adding 50 ml of water, the reaction product mixture was extracted with $CH_2Cl_2$. The extract was dried over $MgSO_4$, filtrated and condensed. The condensate was dissolved in 300 ml toluene and purified by a column chromatography. The purified product was condensed, evaporated to dryness and washed with ethyl acetate (30 ml) three times, to obtain a white powder (No. 6) which was then purified by sublimation to obtain 3.5 g of white solid.

FD Mass Spectroscopy Analysis $C_{36}H_{23}NO$: calculated 485. found 485

Synthesis Example 2

Synthesis of Compound No. 1

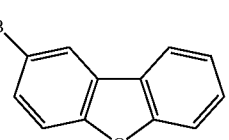

3

4

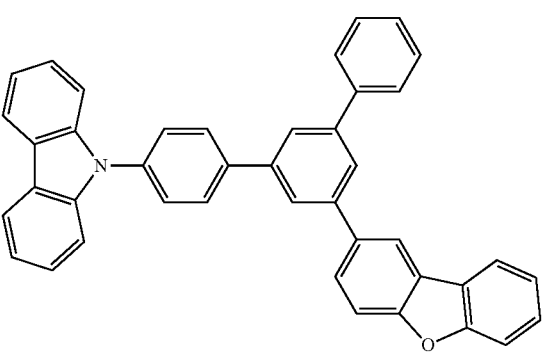

No. 1

A three-necked flask was charged with 7.1 g (1 eq., 15 mmol) of compound 3, 3.8 g (1.2 eq., 18 mmol) of compound 4, 15 ml of 2M $Na_2CO_3$ aqueous solution (30 mmol), 50 ml of THF, and 0.87 g of 5 mol % $Pd[PPh_3]_4$ (0.75 mmol). The contents were refluxed for 8 hrs in an argon atmosphere.

After the reaction, the reaction product mixture was cooled to room temperature and poured into 100 ml of methanol. The precipitated solid was filtrated with suction and purified by a column chromatography. The purified product was condensed, evaporated to dryness and recrystallized twice, to obtain a white powder (No. 1) which was then purified by sublimation to obtain 2.6 g of white solid.

FD Mass Spectroscopy Analysis $C_{42}H_{27}NO$: calculated 561. found 561

Synthesis Example 3

Synthesis of Compound No. 12

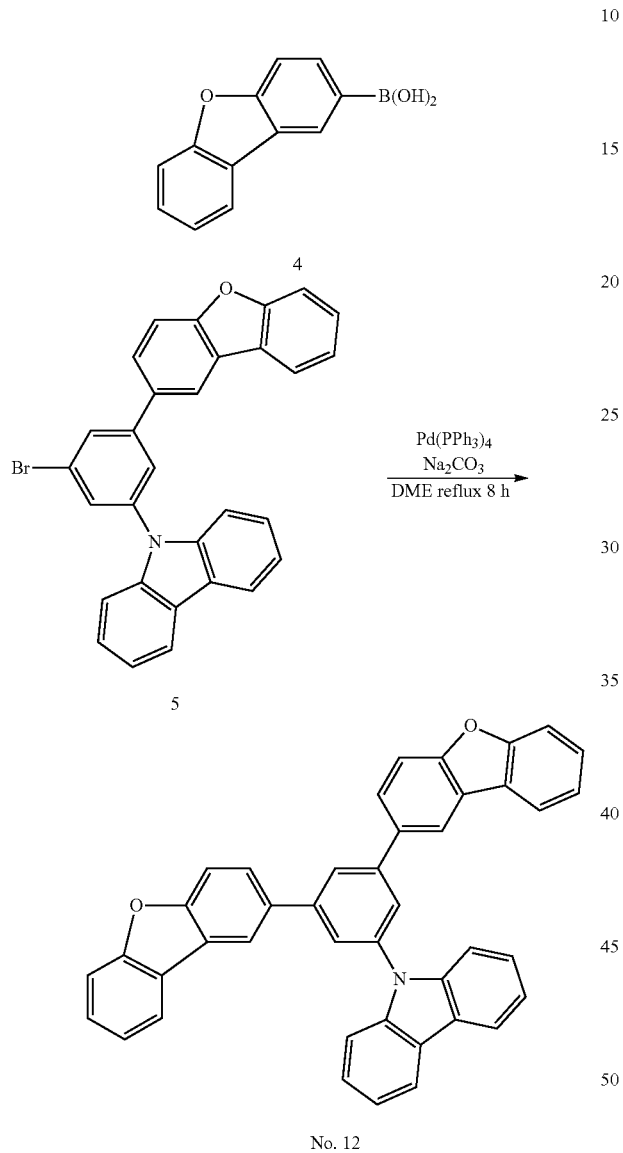

No. 12

A three-necked flask was charged with 3.4 g (1.2 eq., 16 mmol) of compound 4, 6.5 g (1 eq., 13 mmol) of compound 5, 13 ml of 2M $Na_2CO_3$ aqueous solution (26 mmol), 40 ml of DME, and 0.75 g of 5 mol % $Pd[PPh_3]_4$ (0.65 mmol). The contents were refluxed for 8 hrs in an argon atmosphere.

After the reaction, the reaction product mixture was cooled to room temperature and poured into a separatory funnel. After adding 50 ml of water, the reaction product mixture was extracted with $CH_2Cl_2$. The extract was purified by a column chromatography. The purified product was condensed, evaporated to dryness and recrystallized twice, to obtain a white powder (No. 12) which was then purified by sublimation to obtain 3.2 g of white solid.

FD Mass Spectroscopy Analysis $C_{42}H_{25}NO_2$: calculated 575. found 575

Synthesis Example 4

Synthesis of Compound No. 18

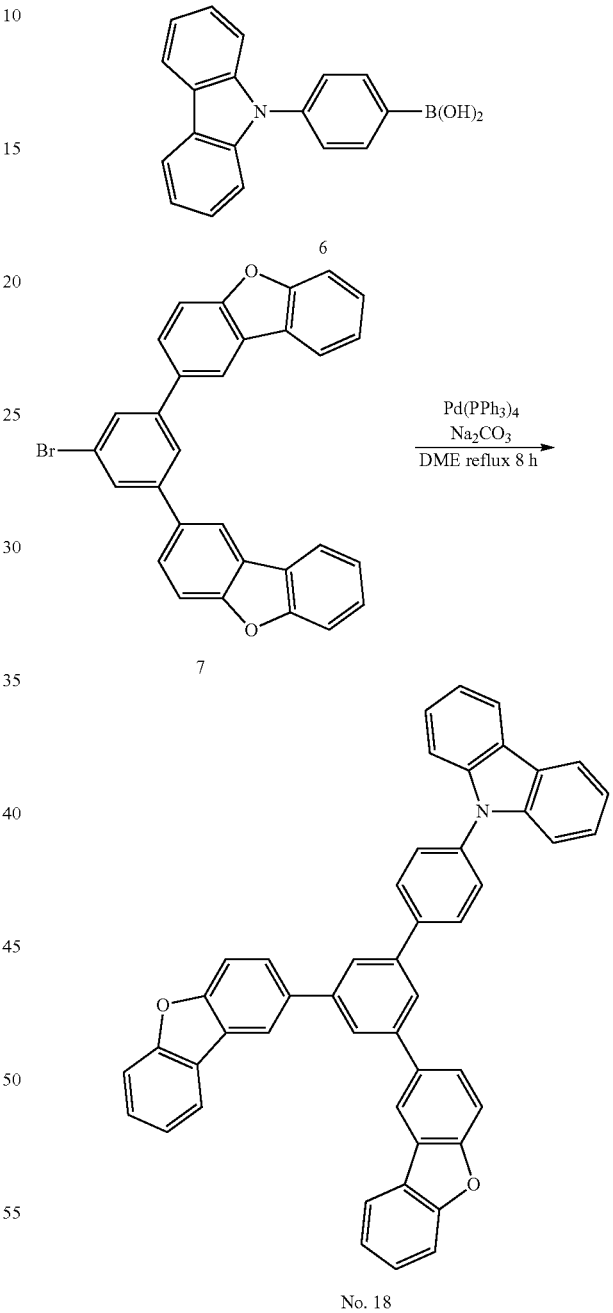

No. 18

A three-necked flask was charged with 3.0 g (1.2 eq., 10 mmol) of compound 6, 4.3 g (1 eq., 8.7 mmol) of compound 7, 9 ml of 2M $Na_2CO_3$ aqueous solution (18 mmol), 40 ml of DME, and 0.51 g of 5 mol % $Pd[PPh_3]_4$ (0.44 mmol). The contents were refluxed for 8 hrs in an argon atmosphere.

After the reaction, the reaction product mixture was cooled to room temperature and poured into a separatory funnel.

After adding 50 ml of water, the reaction product mixture was extracted with $CH_2Cl_2$. The extract was purified by a column chromatography. The purified product was condensed, evaporated to dryness and recrystallized twice, to obtain a white powder (No. 18) which was then purified by sublimation to obtain 3.2 g of white solid.

FD Mass Spectroscopy Analysis $C_{48}H_{29}NO_2$: calculated 651. found 651

Synthesis Example 5

Synthesis of Compound No. 72

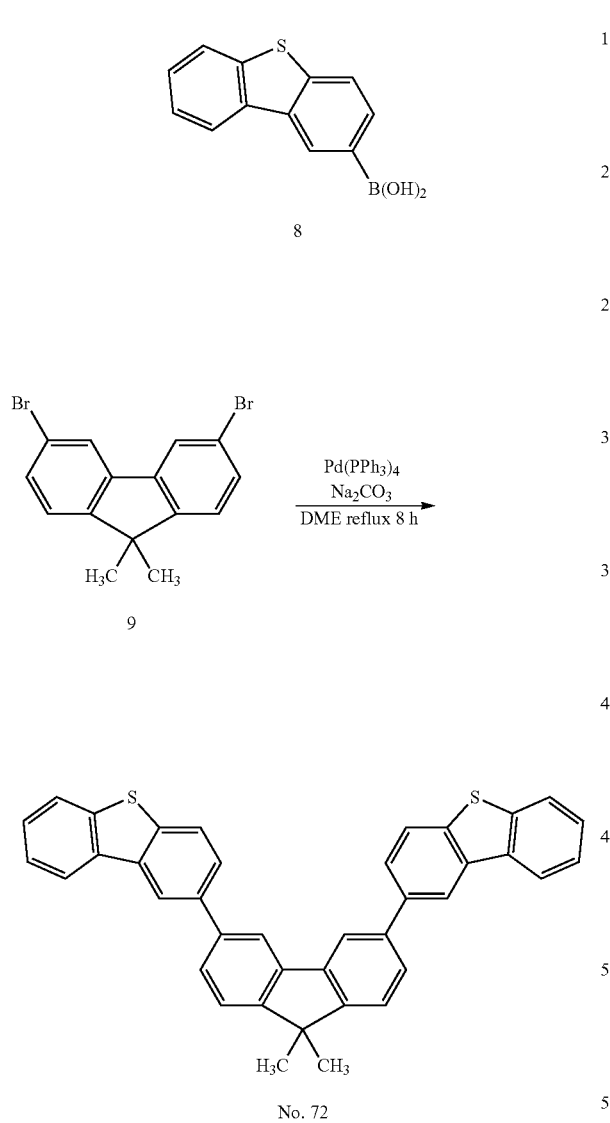

A three-necked flask was charged with 4.0 g (1.2 eq., 17 mmol) of compound 8, 5.1 g (1 eq., 15 mmol) of compound 9, 16 ml of 2M $Na_2CO_3$ aqueous solution (30 mmol), 70 ml of DME, and 0.87 g of 5 mol % $Pd[PPh_3]_4$ (0.75 mmol). The contents were refluxed for 8 hrs in an argon atmosphere.

After the reaction, the reaction product mixture was cooled to room temperature and poured into a separatory funnel. After adding 50 ml of water, the reaction product mixture was extracted with $CH_2Cl_2$. The extract was purified by a column chromatography. The purified product was condensed, evaporated to dryness and recrystallized twice, to obtain a white powder (No. 72) which was then purified by sublimation to obtain 2.8 g of white solid.

FD Mass Spectroscopy Analysis $C_{39}H_{26}S_2$: calculated 558. found 568

Synthesis Example 6

Synthesis of Compound No. 66

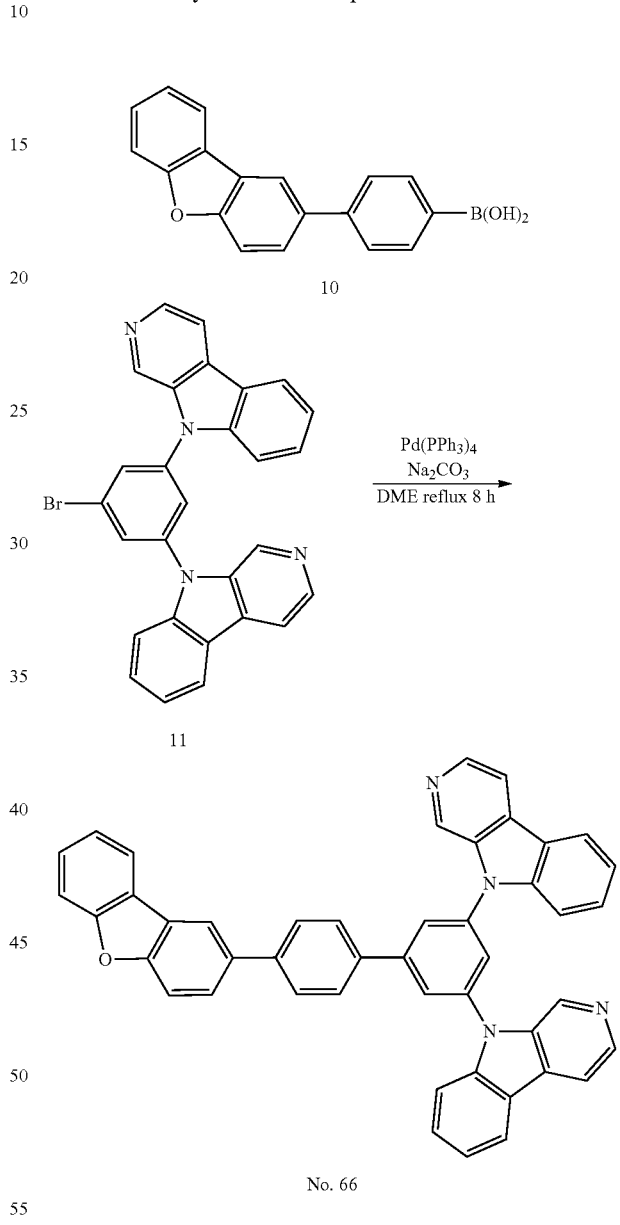

A three-necked flask was charged with 6.1 g (1.2 eq., 21 mmol) of compound 10, 8.6 g (1 eq., 18 mmol) of compound 11, 18 ml of 2M $Na_2CO_3$ aqueous solution (36 mmol), 80 ml of DME, and 1.04 g of 5 mol % $Pd[PPh_3]_4$ (0.9 mmol). The contents were refluxed for 8 hrs in an argon atmosphere.

After the reaction, the reaction product mixture was cooled to room temperature and poured into a separatory funnel. After adding 70 ml of water, the reaction product mixture was extracted with $CH_2Cl_2$. The extract was purified by a column chromatography. The purified product was condensed, evaporated to dryness and recrystallized three times, to obtain a white powder (No. 66) which was then purified by sublimation to obtain 4.0 g of white solid.

FD Mass Spectroscopy Analysis $C_{46}H_{28}N_4O$: calculated 652. found 652

Synthesis Example 7

Synthesis of Compound No. 5

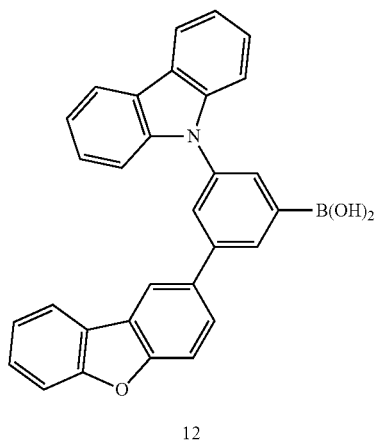

12

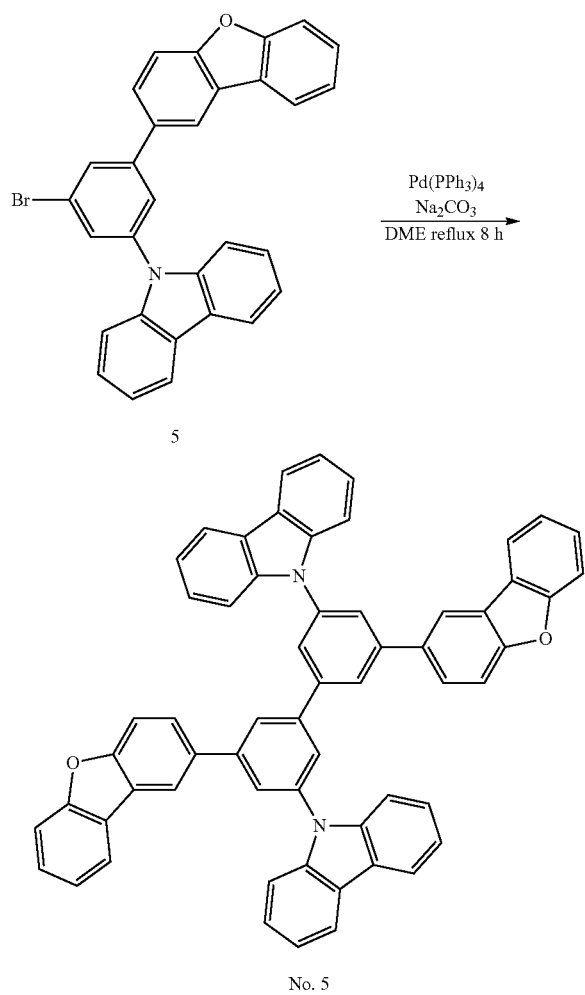

No. 5

A three-necked flask was charged with 3.5 g (1.2 eq., 7.7 mmol) of compound 12, 3.1 g (1 eq., 6.4 mmol) of compound 5, 7 ml of 2M $Na_2CO_3$ aqueous solution (14 mmol), 50 ml of DME, 0.34 g of 5 mol % $Pd[PPh_3]_4$ (0.32 mmol). The contents were refluxed for 8 hrs in an argon atmosphere.

After the reaction, the reaction product mixture was cooled to room temperature and poured into a separatory funnel. After adding 50 ml of water, the reaction product mixture was extracted with $CH_2Cl_2$. The extract was purified by a column chromatography. The purified product was condensed, evaporated to dryness and recrystallized three times, to obtain a white powder (No. 5) which was then purified by sublimation to obtain 2.2 g of white solid.

FD Mass Spectroscopy Analysis $C_{60}H_{36}N_2O_2$: calculated 816. found 816

The measuring conditions of FD-MS (field desorption mass spectrometry) used in Synthesis Examples 1 to 7 are shown below.

Apparatus: HX110 manufactured by JEOL, Ltd.

Acceralation Voltage: 8 kV

Scan range: m/z=50 to 1500

Emitter material: carbon

Emitter current: 0 mA→2 mA/min→40 mA (maintained for 10 min)

Example 1

Preparation of Organic EL Device

A glass substrate of 25 mm×75 mm×1.1 mm thickness having ITO transparent electrode (manufactured by Asahi Glass Company Ltd.) was ultrasonically cleaned in isopropyl alcohol for 5 min and then UV ozone-cleaned for 30 min. The cleaned glass substrate having the transparent electrode lines was mounted to a substrate holder of a vacuum vapor deposition apparatus. On the surface having the transparent electrode lines, a film of HTM1 (see the formula below) having a thickness of 80 nm was first deposited by resistance heating so as to cover the transparent electrode. The HTM1 film functioned as the hole transport/hole injection layer. Then, Compound No. 6 as the host material and Complex K-21 as the dopanat material were vapor co-deposited by resistance heating to successively form a film having a thickness of 30 nm on the HTM1 film. The concentration of Complex K-21 was 7.5% by weight. The co-deposited film functions as the light emitting layer. Then, an ETM1 film having a thickness of 10 nm on the light emitting layer and an ETM2 film having a thickness of 20 nm on the ETM1 film were successively deposited in layers. The ETM1 film and ETM2 film functioned as the first and second electron transport layer, respectively. Then, a LiF electron injecting electrode (cathode) having a thickness of 0.5 nm was deposited at a film-depositing speed of 0.1 Å/min. Finally, a metallic Al was deposited on the LiF film to form a metal cathode having a thickness of 150 nm, thereby obtaining an organic EL device.

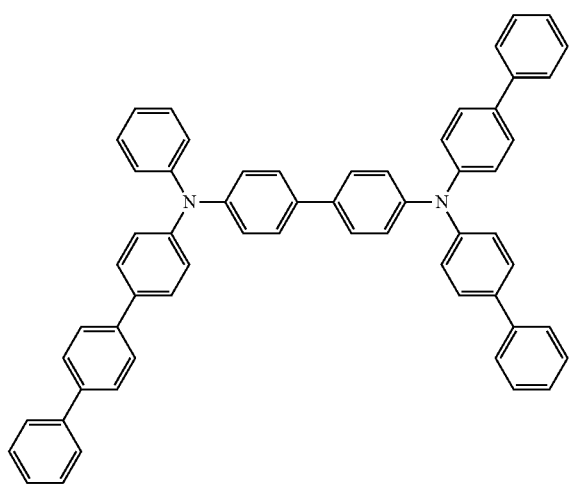

HTM1

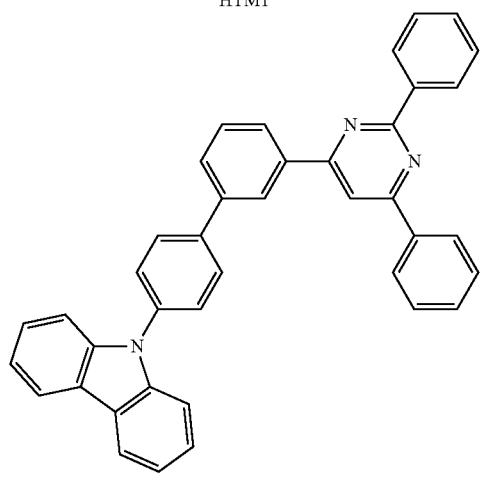

ETM1

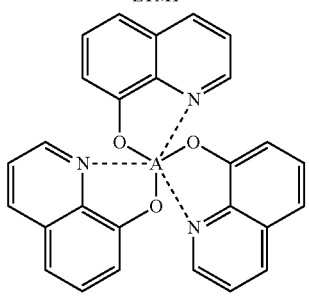

ETM2

Evaluation of Light Emitting Property of Organic EL Device

The organic EL device thus prepared was driven under a direct current to emit light and measured for the wave length (λ), the luminance (L) and the current density to determine the current efficiency (L/J). The results at a current density of 1 mA/cm² are shown in Table 1.

Examples 2-15

Each organic EL device was prepared in the same manner as in Example 1 except for using a host material listed in Table 1 in place of the host Compound No. 5 used in Example 1. The results are shown in Table 1.

Comparative Example 1

An organic EL device was prepared in the same manner as in Example 1 except for using CBP as the host material in place of the host Compound No. 5 used in Example 1. The results are shown in Table 1.

Comparative Example 2

An organic EL device was prepared in the same manner as in Example 1 except for using the following compound X-1 described in WO 2005/113531 in place of the host Compound No. 5 used in Example 1. The results are shown in Table 1.

TABLE 1

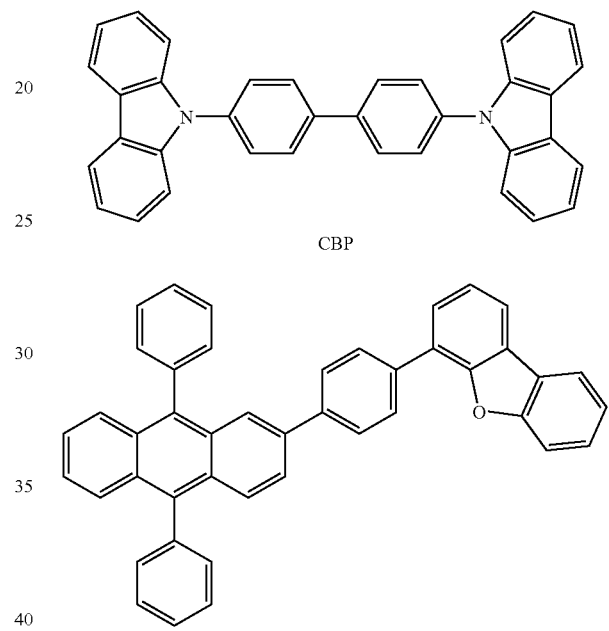

| | Host Compound | Voltage (V) | Luminance (cd/m²) | L/J (cd/A) | EQE (%) | Wave length (nm) |
|---|---|---|---|---|---|---|
| Examples | | | | | | |
| 1 | No. 5 | 5.7 | 178 | 17.8 | 8.1 | 479 |
| 2 | No. 1 | 5.5 | 147 | 14.7 | 6.3 | 481 |
| 3 | No. 6 | 5.9 | 168 | 16.8 | 7.4 | 479 |
| 4 | No. 12 | 5.9 | 140 | 14.0 | 5.9 | 481 |
| 5 | No. 18 | 5.8 | 130 | 13.8 | 5.7 | 479 |
| 6 | No. 35 | 5.6 | 138 | 13.2 | 5.6 | 481 |
| 7 | No. 72 | 5.5 | 148 | 13.5 | 5.6 | 481 |
| 8 | No. 8 | 5.9 | 145 | 14.5 | 6.3 | 479 |
| 9 | No. 26 | 5.9 | 152 | 15.2 | 6.4 | 479 |
| 10 | No. 38 | 5.8 | 146 | 14.6 | 6.1 | 479 |
| 11 | No. 55 | 5.6 | 157 | 15.7 | 6.4 | 481 |
| 12 | No. 69 | 5.9 | 148 | 14.8 | 6.2 | 480 |
| 13 | No. 84 | 5.5 | 154 | 15.4 | 6.3 | 481 |
| 14 | No. 96 | 5.9 | 138 | 13.8 | 5.8 | 481 |
| 15 | No. 99 | 5.6 | 155 | 15.5 | 6.4 | 479 |
| Comparative Examples | | | | | | |
| 1 | CBP | 6.0 | 125 | 8.2 | 3.7 | 480 |
| 2 | X-1 | | no emission of light | | | |

As compared with the compounds used in examples, both the compounds used in comparative examples were poor in the current efficiency, needed a high driving voltage, and showed a short lifetime.

As described above, by using the material for organic EL devices of the invention which is represented by the formulae 1 to 8, organic EL devices having a high emitting efficiency, causing little pixel defects, being excellent in the heat resistance, and having a long lifetime are obtained. Therefore, such organic EL devices are very useful as the display and light source for various electronic instruments.

The invention claimed is:

1. A material for organic electroluminescence devices, which comprises a compound represented by the following formula 2:

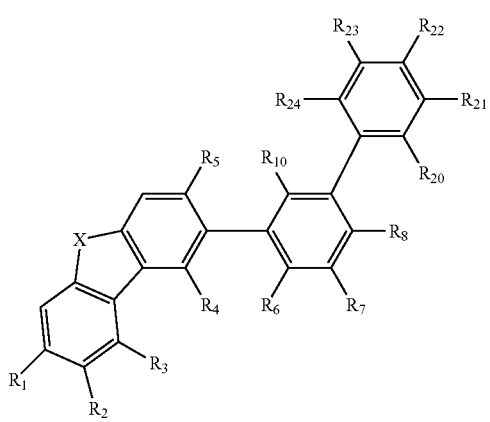

(2)

wherein $R_1$ to $R_8$, $R_{10}$ and $R_{20}$ to $R_{24}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group, and each of $R_1$ to $R_8$, $R_{10}$ and $R_{20}$ to $R_{24}$ having no polymerizable functional group at its terminal end; and X is sulfur atom or oxygen atom, with the proviso that $R_6$ to $R_8$, $R_{10}$ and $R_{20}$ to $R_{24}$ do not form a ring, $R_2$ is not a non-condensed aryl group, and $R_{22}$ is not a methoxy group.

2. A material for organic electroluminescence devices, which comprises a compound represented by the following formula 3:

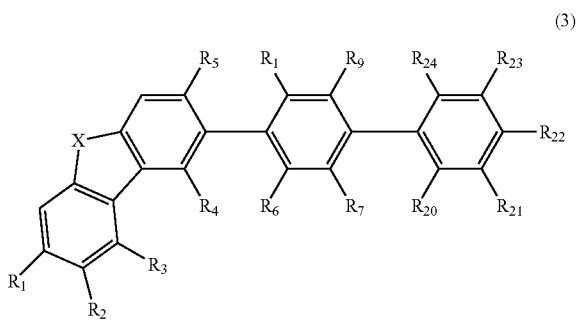

(3)

wherein $R_1$ to $R_7$, $R_9$, $R_{10}$ and $R_{20}$ to $R_{24}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group, each of $R_1$ to $R_7$, $R_9$, $R_{10}$ and $R_{20}$ to $R_{24}$ having no polymerizable functional group at its terminal end; and X is sulfur atom or oxygen atom, with the proviso that $R_6$, $R_7$, $R_9$, $R_{10}$ and $R_{20}$ to $R_{24}$ do not form a ring.

3. A material for organic electroluminescence devices, which comprises a compound represented by the following formula 5:

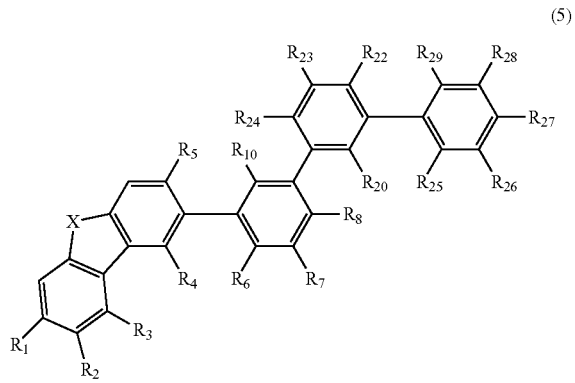

(5)

wherein $R_1$ to $R_8$, $R_{10}$, $R_{20}$, and $R_{22}$ to $R_{29}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group, and each of $R_1$ to $R_8$, $R_{10}$, $R_{20}$, and $R_{22}$ to $R_{24}$ having no polymerizable functional group at its terminal end; and X is sulfur atom or oxygen atom, with the proviso that $R_6$ to $R_8$, $R_{10}$, $R_{20}$, and $R_{22}$ to $R_{24}$ do not form a ring.

4. The material for organic electroluminescence devices according to claim 1, which is represented by the following formula 6:

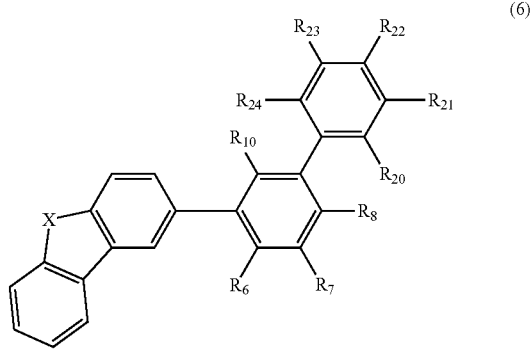

(6)

wherein $R_6$ to $R_8$, $R_{10}$, $R_{20}$ to $R_{24}$, and X are as defined above.

5. The material for organic electroluminescence devices according to claim 2, which is represented by the following formula 7:

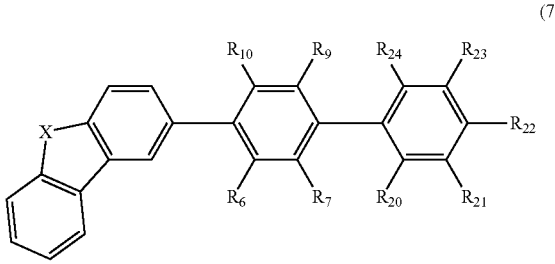

(7)

wherein $R_6$, $R_7$, $R_9$, $R_{10}$, $R_{20}$ to $R_{24}$, and X are as defined above.

6. The material for organic electroluminescence devices according to claim 1, which is represented by the following formula 9:

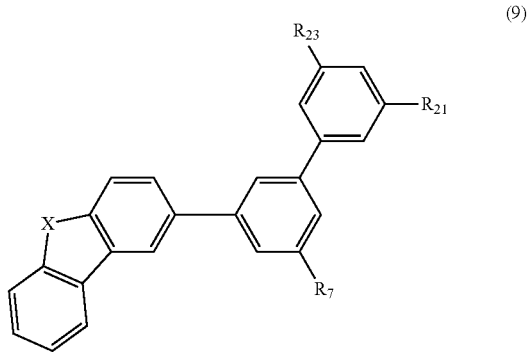

(9)

wherein $R_7$, $R_{21}$, $R_{23}$, and X are as defined above.

7. A material for organic electroluminescence devices, which comprises a compound represented by the following formula 2:

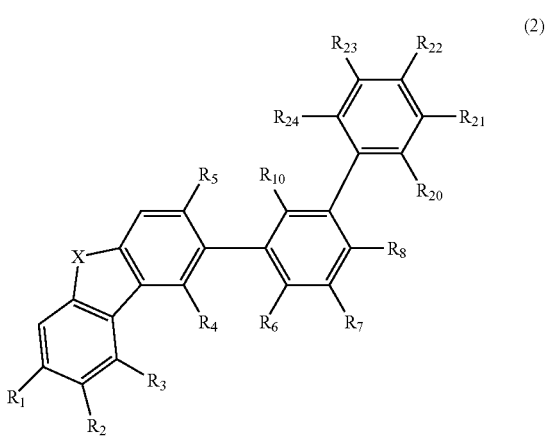

(2)

wherein $R_1$ to $R_8$, $R_{10}$ and $R_{20}$ to $R_{24}$ are each independently hydrogen atom, halogen atom, alkyl group having 1 to 40 carbon atoms which is optionally substituted, cycloalkyl group having 3 to 15 carbon atoms which is optionally substituted, heterocyclic group having 3 to 20 carbon atoms which is optionally substituted, alkoxy group having 1 to 40 carbon atoms which is optionally substituted, non-condensed aryl group having 6 to 40 carbon atoms which is optionally substituted, condensed aryl group having 10 to 18 carbon atoms which is optionally substituted, aryloxy group having 6 to 20 carbon atoms which is optionally substituted, aralkyl group having 7 to 20 carbon atoms which is optionally substituted, arylamino group having 6 to 40 carbon atoms which is optionally substituted, alkylamino group having 1 to 40 carbon atoms which is optionally substituted, aralkylamino group having 7 to 60 carbon atoms which is optionally substituted, arylcarbonyl group having 7 to 40 carbon atoms which is optionally substituted, alkyl halide group having 1 to 40 carbon atoms which is optionally substituted, or cyano group, and each of $R_1$ to $R_8$, $R_{10}$ and $R_{20}$ to $R_{24}$ having no polymerizable functional group at its terminal end; and X is sulfur atom or oxygen atom, with the proviso that $R_6$ to $R_8$, $R_{10}$ and $R_{20}$ to $R_{24}$ do not form a ring, and at least one of $R_6$ to $R_8$, $R_{10}$, and $R_{20}$ to $R_{24}$ is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

8. The material for organic electroluminescence devices according to claim 3, wherein at least one of $R_6$ to $R_8$, $R_{10}$, $R_{20}$, $R_{22}$ to $R_{24}$, and $R_{25}$ to $R_{29}$ of formula 5 is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

9. The material for organic electroluminescence devices according to claim 7, which comprises a compound represented by the following formula 6:

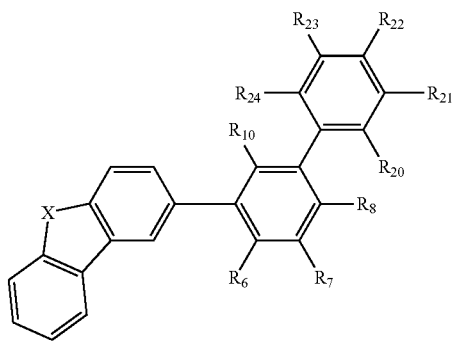

(6)

wherein $R_6$ to $R_8$, $R_{10}$, $R_{20}$ to $R_{24}$, and X are as defined above, and at least one of $R_6$ to $R_8$, $R_{10}$, and $R_{20}$ to $R_{24}$ is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

10. The material for organic electroluminescence devices according to claim 7, which comprises a compound represented by the following formula 9:

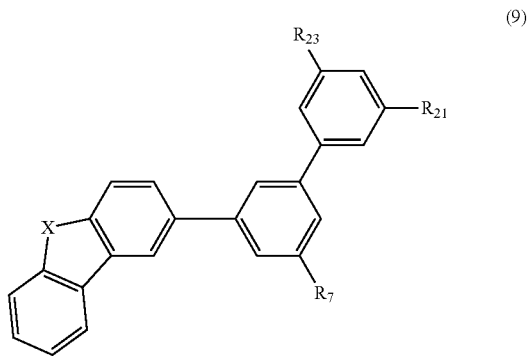

(9)

wherein $R_7$, $R_{21}$, $R_{23}$, and X are as defined above, and at least one of $R_7$, $R_{21}$ and $R_{23}$ is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

11. The material for organic electroluminescence devices according to claim 2, wherein at least one of $R_6$, $R_7$, $R_9$, $R_{10}$, and $R_{20}$ to $R_{24}$ of the formula 3 is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

12. The material for organic electroluminescence devices according to claim 5, wherein at least one of $R_6$, $R_7$, $R_9$, $R_{10}$, and $R_{20}$ to $R_{24}$ of the formula 7 is selected from the group consisting of a substituted or non-substituted carbazolyl group, a substituted or non-substituted dibenzofuranyl group, a substituted or non-substituted azacarbazolyl group and a substituted or non-substituted dibenzothiophenyl group.

13. The material according to claim 1, which is suitable for an organic electroluminescence device.

* * * * *